US012680133B2

(12) United States Patent
Glezer et al.

(10) Patent No.: US 12,680,133 B2
(45) Date of Patent: Jul. 14, 2026

(54) METHODS, COMPOSITIONS, AND SOLID SUPPORTS FOR MULTI-DIMENSIONAL SEQUENCING

(71) Applicant: Singular Genomics Systems, Inc., San Diego, CA (US)

(72) Inventors: Eli N. Glezer, Del Mar, CA (US); Daan Witters, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 592 days.

(21) Appl. No.: 18/303,464

(22) Filed: Apr. 19, 2023

(65) Prior Publication Data

US 2023/0340591 A1 Oct. 26, 2023

Related U.S. Application Data

(60) Provisional application No. 63/480,409, filed on Jan. 18, 2023, provisional application No. 63/334,067, filed on Apr. 22, 2022.

(51) Int. Cl.
*C12P 19/34* (2006.01)
*C12Q 1/6874* (2018.01)

(52) U.S. Cl.
CPC .................................. *C12Q 1/6874* (2013.01)

(58) Field of Classification Search
CPC .................................................... C12Q 1/6869
See application file for complete search history.

(56) References Cited

U.S. PATENT DOCUMENTS

| | | | | |
|---|---|---|---|---|
| 5,686,243 | A | 11/1997 | Royer et al. | |
| 5,830,711 | A | 11/1998 | Barany et al. | |
| 6,027,889 | A | 2/2000 | Barany et al. | |
| 6,027,998 | A | 2/2000 | Pham et al. | |
| 6,605,451 | B1 | 8/2003 | Marmaro et al. | |
| 7,057,026 | B2 | 6/2006 | Barnes et al. | |
| 7,541,444 | B2 | 6/2009 | Milton et al. | |
| 8,003,354 | B2 | 8/2011 | Shen et al. | |
| 8,039,817 | B2 | 10/2011 | Feng et al. | |
| 8,178,360 | B2 | 5/2012 | Barnes et al. | |
| 8,241,573 | B2 | 8/2012 | Banerjee et al. | |
| 8,703,461 | B2 | 4/2014 | Peris et al. | |
| 10,738,072 | B1 | 8/2020 | Graham et al. | |
| 11,236,387 | B2 | 2/2022 | Glezer et al. | |
| 11,434,525 | B2 | 9/2022 | Glezer | |
| 12,060,605 | B2 | 8/2024 | Glezer et al. | |
| 12,227,799 | B2 | 2/2025 | Glezer et al. | |
| 12,460,261 | B2 | 11/2025 | Glezer et al. | |
| 2003/0124594 | A1* | 7/2003 | Church | C07K 1/047 435/6.12 |
| 2004/0096960 | A1 | 5/2004 | Mehta et al. | |
| 2005/0013372 | A1 | 1/2005 | Srinivasan | |
| 2005/0154165 | A1 | 7/2005 | Petereit et al. | |
| 2006/0257629 | A1 | 11/2006 | Lendlein et al. | |
| 2007/0087362 | A1 | 4/2007 | Church et al. | |
| 2007/0141340 | A1 | 6/2007 | Song | |
| 2007/0196492 | A1 | 8/2007 | Ito et al. | |
| 2008/0160559 | A1 | 7/2008 | Carre et al. | |
| 2008/0242560 | A1 | 10/2008 | Gunderson et al. | |
| 2009/0253220 | A1 | 10/2009 | Banerjee | |
| 2010/0055733 | A1 | 3/2010 | Lutolf et al. | |
| 2011/0244048 | A1 | 10/2011 | Amiji et al. | |
| 2012/0270305 | A1 | 10/2012 | Reed et al. | |
| 2012/0301926 | A1 | 11/2012 | Chen et al. | |
| 2012/0309651 | A1 | 12/2012 | Pregibon et al. | |
| 2013/0012399 | A1 | 1/2013 | Myers et al. | |
| 2014/0080717 | A1 | 3/2014 | Li et al. | |
| 2014/0255333 | A1 | 9/2014 | Song et al. | |
| 2015/0005200 | A1 | 1/2015 | Hindson et al. | |
| 2017/0022553 | A1 | 1/2017 | Vijayan et al. | |
| 2018/0016634 | A1 | 1/2018 | Hindson et al. | |
| 2018/0119220 | A1 | 5/2018 | Grass et al. | |
| 2019/0048404 | A1 | 2/2019 | Dambacher | |
| 2021/0040555 | A1 | 2/2021 | Glezer et al. | |
| 2021/0139884 | A1 | 5/2021 | Kellinger et al. | |
| 2021/0363579 | A1 | 11/2021 | Daugharthy et al. | |
| 2022/0090191 | A1 | 3/2022 | Glezer et al. | |
| 2022/0154271 | A1 | 5/2022 | Glezer et al. | |
| 2022/0333190 | A1 | 10/2022 | Glezer et al. | |
| 2024/0167087 | A1* | 5/2024 | Glezer | C12Q 1/6874 |
| 2025/0122560 | A1 | 4/2025 | Glezer et al. | |

FOREIGN PATENT DOCUMENTS

| | | | |
|---|---|---|---|
| WO | WO-1996/007669 | A1 | 3/1996 |
| WO | WO-1997/031256 | A2 | 8/1997 |
| WO | WO-1998/003673 | A1 | 1/1998 |
| WO | WO-2000/056927 | A3 | 3/2000 |
| WO | WO 2001/092579 | A2 | 12/2001 |
| WO | WO-2004/018497 | A2 | 3/2004 |
| WO | 2014085603 | A1 | 6/2014 |
| WO | WO-2016/123480 | A1 | 8/2016 |
| WO | 2017079406 | A1 | 5/2017 |
| WO | WO-2018/148723 | A1 | 8/2018 |
| WO | WO-2020/056044 | A1 | 3/2020 |
| WO | 2020163630 | A1 | 8/2020 |

OTHER PUBLICATIONS

Abramson, R. et al. (1993). "Nucleic acid amplification technologies," *Current Opinion in Biotechnology* 4: 41-47.
Barany, F. (1991). "Genetic Disease Detection and DNA Amplification Using Cloned Thermostable Ligase," *Proceedings of the National Academy of Sciences* 88(1): 189-193.
Barany, F. et al. (1991). "Cloning, overexpression and nucleotide sequence of a thermostable DNA ligase-encoding gene," *Gene* 109(1): 1-11.
Bentley, D. R. et al. (2008). "Accurate whole human genome sequencing using reversible terminator chemistry," *Nature* 456(7218): 53-59.
Bi, W. et al. (1997). "CCR: a rapid and simple approach for mutation detection," *Nucleic Acids Research* 25: 2924-2951.

(Continued)

*Primary Examiner* — Kenneth R Horlick
(74) *Attorney, Agent, or Firm* — Mintz, Levin, Cohn, Ferris, Glovsky and Popeo, P.C.; Zachary L. Terranova

(57) ABSTRACT

Disclosed herein, inter alia, are compositions and methods for detecting polynucleotides within a three-dimensional polymer matrix.

20 Claims, 6 Drawing Sheets

Specification includes a Sequence Listing.

(56) References Cited

OTHER PUBLICATIONS

Cohen, S. M. (2012). "Postsynthetic Methods for the Functionalization of Metal-Organic Frameworks," *Chemical Reviews* 112(2): 970-1000.
Cook, N. (2003). "The use of NASBA for the detection of microbial pathogens in food and environmental samples," *Journal of Microbiological Methods* 53(2): 165-174.
Day, D. J. et al. (1995). "Detection of steroid 21-hydroxylase alleles using gene-specific PCR and a multiplexed ligation detection reaction," *Genomics* 29: 152-162.
Dean, F. B. et al. (2002). "Comprehensive human genome amplification using multiple displacement amplification," *PNAS* 99(8): 5261-5266.
Demidov, V. (2002). "Rolling-circle Amplification in DNA Diagnostics: The Power of Simplicity," *Expert Review of Molecular Diagnostics* 2(6): 542-548.
Denk, W. et al. (1990). "Two-photon laser scanning fluorescence microscopy," *Science* 248(4951): 73-76.
Ehrlich, H. et al. (1991). "Recent Advances in the Polymerase Chain Reaction," *Science* 252: 1643-165.
El-Sagheer, A. H. et al. (2012). "Click Nucleic Acid Ligation: Applications in Biology and Nanotechnology," *Accounts of chemical research* 45(8): 1258-1267.
Fan, T. et al. (2018). "Branched rolling circle amplification method for measuring serum circulating microRNA levels for early breast cancer detection," *Cancer Science* 111(1): 297-298.
Favis, R. et al. (2000). "Universal DNA array detection of small insertions and deletions in BRCA1 and BRCA2," *Nature Biotechnology* 18: 561-564.
Furukawa, H. et al. (2013). "The chemistry and applications of metal-organic frameworks," *Science* 341(6149): 1230444.
Gustafsson, M. G. L. et al. (2008). "Three-dimensional resolution doubling in wide-field fluorescence microscopy by structured illumination," *Biophysical Journal* 94(12): 4957-4970.
Heintzmann, R. et al. (2017, e-published Nov. 10, 2017). "Super-Resolution Structured Illumination Microscopy," *Chemical Reviews* 117(23): 13890-13908.
Hsuih, T. C. et al. (1996). "Novel, ligation-dependent PCR assay for detection of hepatitis C in serum," *Journal of Clinical Microbiology* 34(3): 501-507.
Kato, M. et al. (1995). "Polymerization of Methyl Methacrylate with the Carbon Tetrachloride/Dichlorotris-(triphenylphosphine)ruthenium(II)/Methylaluminum Bis(2,6-di-tert-butylphenoxide) Initiating System: Possibility of Living Radical Polymerization," *Macromolecules* 28(5): 1721-1723.
Lage, J. M. et al. (2003). "Whole genome analysis of genetic alterations in small DNA samples using hyperbranched strand displacement amplification and array—CGH," *Genome research* 13(2): 294-307.
Landegren, U. et al. (1988). "A ligase-mediated gene detection technique," *Science* 4869: 1077-80.
Larsson, C. et al. (2010). "In situ detection and genotyping of individual mRNA molecules," *Nature America* 7: 395-397.
Lizardi, P. et al. (1998). "Mutation detection and single-molecule counting using isothermal rolling-circle amplification," *Nature Genetics* 19: 225-232.
Manuguerra I. et al. (2018). "Gene assembly via one-pot chemical ligation of DNA promoted by DNA nanostructure," *Chemical Communications* 54(36): 4529-4532.
Mag, M. et al. (1992). "Synthesis and Selective Cleavage of an Oligodeoxynucleotide Containing a Bridged Non-Chiral Internucleotide 3'-Phosphoramidate Linkage," *Tetrahedron Letters* 33(48): 7319-22.
Moad, G. et al. (2005). "Living Radical Polymerization by the RAFT Process," *Australian Journal of Chemistry* 58(6): 379-410.
Nalawade, A. C. et al. (2015). "Inverse high internal phase emulsion polymerization (i-HIPE) of GMMA, HEMA and GDMA for the preparation of superporous hydrogels as a tissue engineering scaffold," *Journal of Materials Chemistry B* 4(3): 450-460.
Nilsson, M. et al. (1994). "Padlock Probes: Circularizing Oligonucleotides for Localized DNA Detection," *Science* 265: 2085-2088.
Odeh, F. et al. (2019). "Aptamers chemistry: Chemical modifications and conjugation strategies," *Molecules* 25(1): 3.
Otsu, T. et al. (1982). "Role of initiator-transfer agent-terminator (iniferter) in radical polymerizations: Polymer design by organic disulfides as iniferters," *Macromolecular Rapid Communications* 3: 127-132.
Polstra, A. M. et al. (2002). "Development of real-time NASBA assays with molecular beacon detection to quantify mRNA coding for HHV-8 lytic and latent genes," *BMC Infectious Diseases* 2(1): 1-10.
Rabenau, H. F. et al. (2000). "Low correlation of serology with detection of Chlamydia trachomatis by ligase chain reaction and antigen EIA," *Infection* 28: 97-102.
Sapoznik, E. et al. (2020). "A versatile oblique plane microscope for large-scale and high-resolution imaging of subcellular dynamics," *eLife* 9: e57681.
Schweitzer, B. et al. (2001). "Combining nucleic acid amplification and detection," *Current Opinion in Biotechnology* 12(1): 21-27.
Southworth, M. W. et al. (1996). "Cloning of thermostable DNA polymerases from hyperthermophilic marine Archaea with emphasis on *Thermococcus* sp. 9 degrees N-7 and mutations affecting 3'-5' exonuclease activity," *Proceedings of the National Academy of Sciences* 93(11): 5281-5285.
Veregin, R. P. N. et al. (1993). "Free radical polymerizations for narrow polydispersity resins: electron spin resonance studies of the kinetics and mechanism," *Macromolecules* 26(20): 5316-5320.
Walker, G. et al. (1992). "Strand Displacement Amplification—An Isothermal, In Vitro DNA Amplification Technique," *Nucleic Acids Research* 20(7): 1691-1696.
Walker, J.W. et al. (1988). "Photolabile 1-(2-Nitrophenyl)ethyl Phosphate Esters of Adenine Nucleotide Analogues. Synthesis and Mechanism of Photolysis," *Journal of the American Chemical Society* 110(21): 7170-7177.
Wang, J. et al. (1995). "Controlled/"living" radical polymerization. atom transfer radical polymerization in the presence of transition-metal complexes," *Macromolecules* 117(20): 5614- 5615.
Yeole, N. (2010). "Thiocarbonylthio Compounds," *Synlett* 10: 1572-1573.
York, A.G. et al. (2013). "Instant super-resolution imaging in live cells and embryos via analog image processing," *Nature Methods* 10: 1122-1126.
Zhou, H. et al. (2012). "Introduction to Metal—Organic Frameworks," *Chemical Reviews* 112(2): 673-674.
Zirvi, M. et al. (1999). "Ligase-based detection of mononucleotide sequences," *Nucleic Acids Research* 27(24): e40-e47.
International Search Report and Written Opinion for PCT/US2020/017060, mailed Jul. 20, 2020, 16 pages.
Flot, J.F. et al. (2015). "Contact genomics: scaffolding and phasing (meta) genomes using chromosome 3D physical signatures." FEBS letters 589(20): 2966-2974.
Partial European Search Report for EP Application No. 20752608.8, mailed Oct. 6, 2022.

* cited by examiner

METHODS, COMPOSITIONS, AND SOLID SUPPORTS FOR MULTI-DIMENSIONAL SEQUENCING

CROSS-REFERENCES TO RELATED APPLICATIONS

This application claims the benefit of U.S. Provisional Application No. 63/334,067, filed Apr. 22, 2022, and U.S. Provisional Application No. 63/480,409, filed Jan. 18, 2023, each of which is incorporated herein by reference in its entirety and for all purposes.

REFERENCE TO SEQUENCE LISTING SUBMITTED ELECTRONICALLY

The Sequence Listing titled 051385-570001US SEQUENCE LISTING ST26.XML, was created on Apr. 18, 2023 in machine format IBM-PC, MS-Windows operating system, is 86,780 bytes in size, and is hereby incorporated by reference in its entirety for all purposes.

BACKGROUND

Sequencing-by-synthesis (SBS) is often performed by imaging clusters of amplicons having multiple identical copies of a starting molecule. As sequencing capacity has grown, it has pushed the limits of the density of cluster spacing that can be imaged within a two dimensional (2D) plane. The maximum resolving power of imaging systems is limited by factors such as diffraction. Achieving high resolution typically involves using microscope objectives with a high numerical aperture (NA), which can limit the practical size of the field of view (FOV), and hence the total information content in each image. Various methods of super-resolution imaging that have been developed enable optical imaging at resolution beyond diffraction limits. However, these approaches are not well suited to the high imaging rates typically utilized for DNA sequencing.

BRIEF SUMMARY

In view of the foregoing, there is a need for improved methods of nucleic acid sequencing. The present disclosure addresses this need, and provides additional benefits as well.

In an aspect is provided a method of amplifying a polynucleotide, said method comprising: contacting a solid support comprising a multi-layer polymer with a polynucleotide, and amplifying the polynucleotide with a polymerase and a plurality of nucleotides to generate amplification products, wherein said multi-layer polymer comprises: a first layer attached to said solid support, wherein said first layer comprises a first oligonucleotide within a first polymer layer, wherein said first oligonucleotide comprises a first amplification primer binding sequence and a first sequencing primer binding sequence; a second layer, wherein said second layer does not comprise an amplification primer binding sequence within a second polymer layer; and a third layer attached to said second layer, wherein said third layer comprises a second oligonucleotide within a third polymer layer, wherein and said second oligonucleotide comprises a second amplification primer binding sequence and a second sequencing primer binding sequence, wherein said second polymer layer is attached to said first and third polymer layer.

In an aspect is provided a composition including: (i) a first layer including a polymeric gel including a plurality of oligonucleotides attached to the polymeric gel; (ii) a second layer including a polymeric gel, wherein the polymeric gel does not include a plurality of oligonucleotides attached to the polymeric gel; and (iii) a third layer including a polymeric gel including a plurality of oligonucleotides attached to the polymeric gel.

In an aspect is provided a composition including: (i) a first layer including a polymeric gel including a plurality of particles, each particle including a plurality of oligonucleotide moieties covalently attached to the particle via a polymeric bioconjugate linker; (ii) a second layer including a polymeric gel including a plurality of particles, wherein each particle does not include a plurality of oligonucleotide moieties; and (iii) a third layer including a polymeric gel including a plurality of particles, each particle including a plurality of oligonucleotide moieties covalently attached to the particle via a polymeric bioconjugate linker.

In an aspect is provided a composition including: (i) a first layer including a plurality of particles, each particle including a plurality of oligonucleotide moieties covalently attached to the particle via a polymeric bioconjugate linker; (ii) a second layer including a plurality of particles, wherein each particle does not include a plurality of oligonucleotide moieties; and (iii) a third layer including a plurality of particles, each particle including a plurality of oligonucleotide moieties covalently attached to the particle via a polymeric bioconjugate linker.

In an aspect is provided a composition including two or more layers, wherein each of the two or more layers includes a polymeric gel including a plurality of oligonucleotides attached to the polymeric gel, wherein every two layers of the two or more layers is separated by a layer including a passive polymeric gel, wherein the passive polymeric gel does not include a plurality of oligonucleotides attached to the passive polymeric gel.

BRIEF DESCRIPTION OF THE DRAWINGS

FIG. 5A shows a polymer scaffold of particles (e.g., solid core particles) arranged in an array, wherein the inactive polymer layer includes a single layer of particles. FIG. 5B shows a polymer scaffold of particles (e.g., solid core particles) arranged in an array, wherein the inactive polymer layer includes two layers of particles. As described herein, each set of two active layers separated by an inactive polymer layer may be referred to as a contiguous layered unit, as denoted by the brackets on the right-hand side of the particle scaffolds in FIGS. 5A-5B. In this illustration, each particle scaffold has two contiguous layered units, each separated by at least one inactive polymer layer. FIG. 5C shows the polymer scaffold of particles of FIG. 5B, and a process wherein using, e.g., confocal microscopy or multi-photon microscopy, two-dimensional planes of images are collected by scanning along one axis (e.g., the z direction). Note, multiple two-dimensional planes may be acquired for the same particles in the xy plane (e.g., Scan-1 and Scan-2) whereby detection events may be occurring on different z-planes within those particles, or two-dimensional planes may be acquired for the different particles in the xy plane (e.g., Scan-1 and Scan-3). These images, shown in FIG. 5D, may then be further processed to determine the fluorescent event, and thus the sequence of the target polynucleotide.

DETAILED DESCRIPTION

Figure 1:
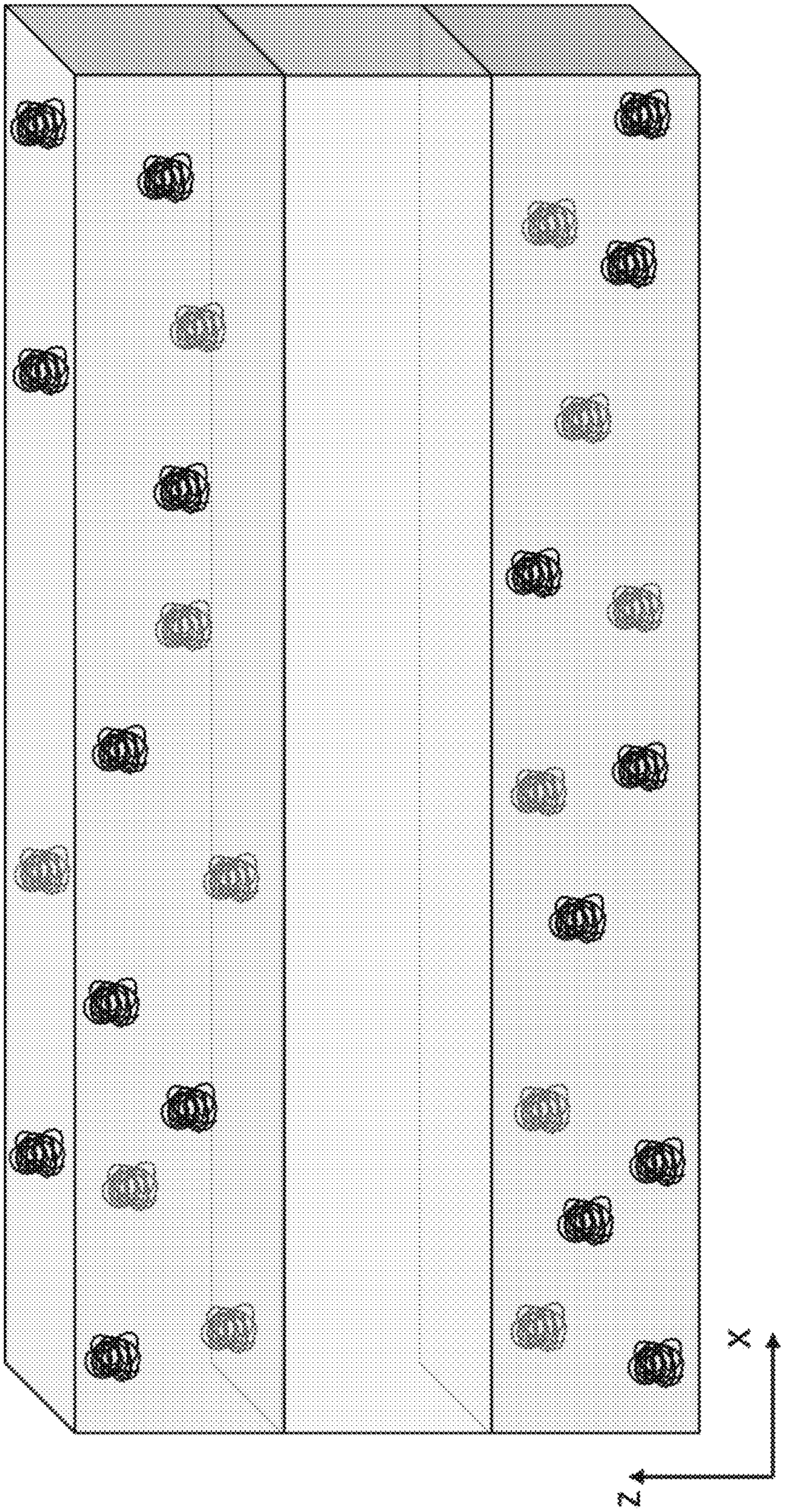
FIG. 1 illustrates one embodiment of a spatially heterogeneous polymer scaffold (e.g., a layered polymeric composition) as described herein. In this embodiment, the polymer scaffold includes alternating active layers (e.g., layers of particles, polymers, or a combination thereof, including covalently-attached oligonucleotide primers and/or amplification products) and inactive, or passive layers (e.g., layers of particles, polymers, or a combination thereof that do not include oligonucleotide primers). As illustrated, the active layers include discrete sites containing amplification products depicted as the black coils. The active layers are separated from one another by an inactive layer (i.e., a polymer that does not include immobilized polynucleotides). The active layers may facilitate amplification reactions at each immobilized oligonucleotide primer to form spatially separated amplicon clusters. The combination of the three layers may also be referred to as a contiguous layered unit.

The aspects and embodiments described herein relate to detecting polynucleotides within a three-dimensional polymer matrix.

I. Definitions

All patents, patent applications, articles and publications mentioned herein, both supra and infra, are hereby expressly incorporated herein by reference in their entireties. The practice of the technology described herein will employ, unless indicated specifically to the contrary, conventional methods of chemistry, biochemistry, organic chemistry, molecular biology, bioinformatics, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, NY 1994); and Sambrook and Green, Molecular Cloning: A Laboratory Manual, 4th Edition (2012). Methods, devices and materials similar or equivalent to those described herein can be used in the practice of this invention.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

In the description, relative terms such as "before," "after," "above," "below," "up," "down," "top" and "bottom" as well as derivative thereof (e.g., "horizontally," "downwardly," "upwardly," etc.) should be construed to refer to the orientation as then described or as shown in the drawing or figure under discussion. These relative terms are for convenience of description and do not require that the system be constructed or operated in a particular orientation.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances two or more associated species are "tethered", "coated", "attached", or "immobilized" to one another or to a common solid or semisolid support (e.g. a receiving substrate). An association may refer to a relationship, or connection, between two entities. Associated may refer to the relationship between a sample and the DNA molecules, RNA molecules, or polynucleotides originating from or derived from that sample. These relationships may be encoded in oligonucleotide barcodes, as described herein. A polynucleotide is associated with a sample if it is an endogenous polynucleotide, i.e., it occurs in the sample at the time the sample is obtained, or is derived from an endogenous polynucleotide. For example, the RNAs endogenous to a cell are associated with that cell. cDNAs resulting from reverse transcription of these RNAs, and DNA amplicons resulting from PCR amplification of the cDNAs, contain the sequences of the RNAs and are also associated with the cell. The polynucleotides associated with a sample need not be located or synthesized in the sample, and are considered associated with the sample even after the sample has been destroyed (for example, after a cell has been lysed). Barcoding can be used to determine which polynucleotides in a mixture are associated with a particular sample. The term "immobilized", as used herein, refers to the association, attachment, or binding between a molecule (e.g. linker, adapter, oligonucleotide) and a solid support in a manner that provides a stable association under the conditions of elongation, amplification, ligation, and other processes as described herein. Such binding can be covalent or non-covalent. Non-covalent binding includes electrostatic, hydrophilic and hydrophobic interactions. Covalent binding is the formation of covalent bonds that are characterized by sharing of pairs of electrons between atoms. Such covalent binding can be directly between the molecule and the solid support or can be formed by a cross linker or by inclusion of a specific reactive group on either the solid support or the molecule or both. Covalent attachment of a molecule can be achieved using a binding partner, such as avidin or streptavidin, immobilized to the solid support and the non-covalent binding of the biotinylated molecule to the avidin or streptavidin. Immobilization may also involve a combination of covalent and non-covalent interactions.

As used herein, the term "3' end" designates the end of a nucleotide strand that has the hydroxyl group of the third carbon in the sugar-ring of the deoxyribose at its terminus.

As used herein, the term "5' end" designates the end of a nucleotide strand that has the fifth carbon in the sugar-ring of the deoxyribose at its terminus.

As used herein, the term "complementary" or "substantially complementary" refers to the hybridization, base pairing, or the formation of a duplex between nucleotides or nucleic acids. For example, complementarity exists between the two strands of a double stranded DNA molecule or between an oligonucleotide primer and a primer binding site on a single stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence, and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g., chemical compounds, biomolecules, nucleotides, binding reagents, cells, substrates, or solid supports) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, a protein (e.g., an antibody), or enzyme. In some embodiments contacting includes allowing a particle described herein to interact with an array.

As used herein, the terms "fluidic contact" or "fluidic contacting" or "fluidic communication" refers to at least two spatial regions being connected together such that a liquid or gas may flow between the two spatial regions. In embodiments, two spatially separated species (e.g., chemical compounds, biomolecules, nucleotides, binding reagents, cells, substrates, polymers, polymeric gels, or solid supports) are in fluidic contact when a liquid is capable of contacting each species, optionally simultaneously contacting both species. For example, placing two permeable substrates in fluidic contact may allow diffusion or flowing of a fluid (e.g., one or more liquid reagents) from one substrate to the other substrate. In some embodiments, the first later, the second layer, and the third layer of a multi-layer composition are in fluidic contact, wherein the first layer and the third layer are also in fluidic contact if present in the same fluidic environment. In embodiments, fluidic contact may be achieved using an integrated system of one or more chambers, ports, and/or channels that are interconnected and coupled via one or more connections or tubes.

As used herein, the terms "library", "RNA library" or "DNA library" or "library of DNA molecules" are used in accordance with their plain ordinary meaning and refer to a collection or a population of similarly sized nucleic acid fragments with known adapter sequences (e.g., known adapters attached to the 5' and 3' ends of each of the fragments). In embodiments, the library includes a plurality of nucleic acid fragments including one or more adapter sequences. In embodiments, the library includes circular nucleic acid templates. Libraries are typically prepared from input RNA, DNA, or cDNA and are processed by fragmentation, size selection, end-repair, adapter ligation, amplification, and purification. Alternative amplification-free (i.e., PCR free) methods for preparing a library of molecules include shearing input polynucleotides, size selecting and ligating adapters. A library may correspond to a single sample or a single origin. Multiple libraries, each with their own unique adapter sequences, may be pooled and sequenced in the same sequencing run using the methods and compositions described herein.

"Hybridize" shall mean the annealing of a nucleic acid sequence to another nucleic acid sequence (e.g., one single-stranded nucleic acid (such as a primer) to another nucleic acid) based on the well-understood principle of sequence complementarity. In an embodiment the other nucleic acid is a single-stranded nucleic acid. In some embodiments, one portion of a nucleic acid hybridizes to itself, such as in the formation of a hairpin structure. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution.

As used herein, "specifically hybridizes" refers to preferential hybridization under hybridization conditions where two nucleic acids, or portions thereof, that are substantially complementary, hybridize to each other and not to other nucleic acids that are not substantially complementary to either of the two nucleic acids. For example, specific hybridization includes the hybridization of a primer or capture nucleic acid to a portion of a target nucleic acid (e.g., a template, or adapter portion of a template) that is substantially complementary to the primer or capture nucleic acid. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex, which comprises a double stranded portion of nucleic acid.

As used herein, "hybridizing" or "annealing" are used interchangeably in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the melting temperature (Tm) of the formed hybrid, and the G:C ratio within the nucleic acids. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. For example, hybridizing a primer (e.g., an invasion primer as described herein) to a polynucleotide strand (e.g., a strand of a double-stranded polynucleotide) includes combining the primer and the polynucleotide strand in a reaction vessel under suitable hybridization reaction conditions.

As used herein, "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, "capable of hybridizing" is used in accordance with its ordinary meaning in the art and refers to two oligonucleotides that, under suitable conditions, can form a duplex (e.g., Watson-Crick pairing) which includes a double-stranded portion of nucleic acid. Such conditions, known in the art and described herein, depend upon, for example, the nature of the nucleotide sequence, temperature, and buffer conditions. The stringency of hybridization can be influenced by various parameters, including degree of identity and/or complementarity between the polynucleotides (or any target sequences within the polynucleotides) to be hybridized; melting point of the polynucleotides and/or target sequences to be hybridized, referred to as "Tm"; parameters such as salts, buffers, pH, temperature, GC % content of the polynucleotide and primers, and/or time. Typically, hybridization is favored in lower temperatures and/or increased salt concentrations, as well as reduced concentrations of organic solvents. Some exemplary conditions suitable for hybridization include incubation of the polynucleotides to be hybridized in solutions having sodium salts, such as NaCl, sodium citrate and/or sodium phosphate. In some embodiments, hybridization or wash solutions can include about 10-75% formamide and/or about 0.01-0.7% sodium dodecyl sulfate (SDS). In some embodiments, a hybridization solution can be a stringent hybridization solution which can include any combination of 50% formamide, 5×SSC (0.75 M NaCl, 0.075 M sodium citrate), 50 mM sodium phosphate (pH 6.8), 0.1% sodium pyrophosphate, 5×Denhardt's solution, 0.1% SDS, and/or 10% dextran sulfate. In some embodiments, the hybridization or washing solution can include BSA (bovine serum albumin). In some embodiments, hybridization or washing can be conducted at a temperature range of about 20-25° C., or about 25-30° C., or about 30-35° C., or about 35-40° C., or about 40-45° C., or about 45-50° C., or about 50-55° C., or higher. In some embodiments, hybridization or washing can be conducted for a time range of about 1-10 minutes, or about 10-20 minutes, or about 20-30 minutes, or about 30-40 minutes, or about 40-50 minutes, or about 50-60 minutes, or longer. In some embodiments, hybridization or wash conditions can be conducted at a pH range of about 5-10, or about pH 6-9, or about pH 6.5-8, or about pH 6.5-7.

As may be used herein, the terms "nucleic acid," "nucleic acid molecule," "nucleic acid sequence," "strand," "nucleic acid fragment," and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. In some embodiments, an oligonucleotide is a primer configured for extension by a polymerase when the primer is annealed completely or partially to a complementary nucleic acid template. A primer is often a single stranded nucleic acid. In certain embodiments, a primer, or portion thereof, is substantially complementary to a portion of an adapter. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. In some embodiments, an oligonucleotide may be immobilized to a solid support.

As used herein, the terms "polynucleotide primer", "oligonucleotide primer", and "primer" refers to any polynucleotide molecule that may hybridize to a polynucleotide template, be bound by a polymerase, and be extended in a template-directed process for nucleic acid synthesis (e.g., amplification and/or sequencing). The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment, the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

As used herein, the term "primer binding sequence" refers to a polynucleotide sequence that is complementary to at least a portion of a primer (e.g., a sequencing primer or an amplification primer). Primer binding sequences can be of any suitable length. In embodiments, a primer binding sequence is about or at least about 10, 15, 20, 25, 30, or more nucleotides in length. In embodiments, a primer binding sequence is 10-50, 15-30, or 20-25 nucleotides in length. The primer binding sequence may be selected such that the primer (e.g., sequencing primer) has the preferred characteristics to minimize secondary structure formation or minimize non-specific amplification, for example having a length of about 20-30 nucleotides; approximately 50% GC content, and a Tm of about 55° C. to about 65° C.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The term "messenger RNA" or "mRNA" refers to an RNA that is without introns and is capable of being translated into a polypeptide. The term "RNA" refers to any ribonucleic acid, including but not limited to mRNA, tRNA (transfer RNA), rRNA (ribosomal RNA), and/or noncoding RNA (such as lncRNA (long noncoding RNA)). The term "cDNA" refers to a DNA that is complementary or identical to an RNA, in either single stranded or double stranded form.

The order of elements within a nucleic acid molecule is typically described herein from 5' to 3'. In the case of a double-stranded molecule, the "top" strand is typically shown from 5' to 3', according to convention, and the order of elements is described herein with reference to the top strand.

A polynucleotide is typically composed of a specific sequence of four nucleotide bases (nucleobases): adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the terms "analogue" and "analog", in reference to a chemical compound, refers to compound having a structure similar to that of another one, but differing from it in respect of one or more different atoms, functional groups, or substructures that are replaced with one or more other atoms, functional groups, or substructures. In the context of a nucleotide, a nucleotide analog refers to a compound that, like the nucleotide of which it is an analog, can be incorporated into a nucleic acid molecule (e.g., an extension product) by a suitable polymerase, for example, a DNA polymerase in the context of a nucleotide analogue. The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, a "native" nucleotide is used in accordance with its plain and ordinary meaning and refers to a naturally occurring nucleotide that does not include an exogenous label (e.g., a fluorescent dye, or other label) or chemical modification such as may characterize a nucleotide analog. Examples of native nucleotides useful for carrying out procedures described herein include: dATP (2'-deoxy-adenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

In embodiments, the sequencing nucleotides of the present disclosure use a cleavable linker to attach the label to the nucleotide. The use of a cleavable linker ensures that the label can, if required, be removed after detection, avoiding any interfering signal with any labelled nucleotide incorporated subsequently. The use of the term "cleavable linker" is not meant to imply that the whole linker is required to be removed from the nucleotide base. The cleavage site can be located at a position on the linker that ensures that part of the linker remains attached to the nucleotide base after cleavage. The linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytidine, thymidine or uracil and the N-4 position on cytosine.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite ($Na_2S_2O_4$), weak acid, hydrazine ($N_2H_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently $-NH_2$, $-CN$, $-CH_3$, $C_2$-$C_6$ allyl (e.g., $-CH_2-CH=CH_2$), methoxyalkyl (e.g., $-CH_2-O-CH_3$), or $-CH_2N3$. In embodiments, the blocking moiety is attached to the 3' oxygen of the nucleotide and is independently

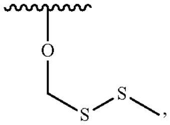 , 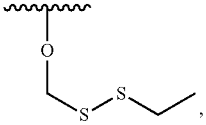 ,

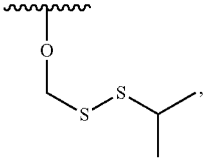 , 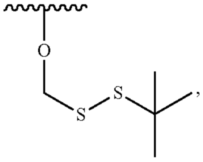 ,

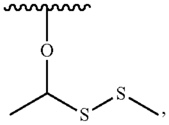 , 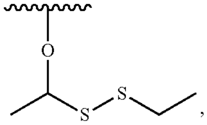 , 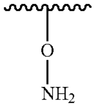 ,

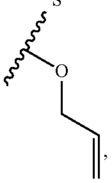 , 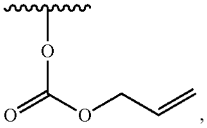 , 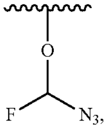 ,

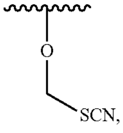 , 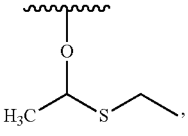 , 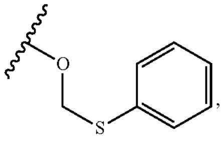 ,

-continued

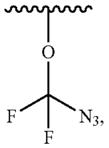,

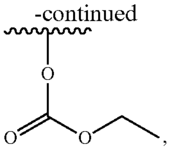,

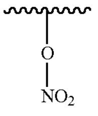,

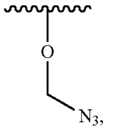, or

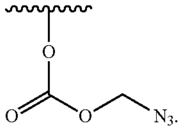.

A label moiety of a modified nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the OH group at the 3'-position of deoxyribose. Nucleotide analogues and DNA polymerase-based DNA sequencing are also described in U.S. Pat. No. 6,664,079, which is incorporated herein by reference in its entirety for all purposes. Non-limiting examples of detectable labels include labels comprising fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, the label is a fluorophore.

In some embodiments, a nucleic acid comprises a label. As used herein, the term "label" or "labels" is used in accordance with their plain and ordinary meanings and refer to molecules that can directly or indirectly produce or result in a detectable signal either by themselves or upon interaction with another molecule. Non-limiting examples of detectable labels include fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the label is a dye. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, a particular nucleotide type is associated with a particular label, such that identifying the label identifies the nucleotide with which it is associated. In embodiments, the label is luciferin that reacts with luciferase to produce a detectable signal in response to one or more bases being incorporated into an elongated complementary strand, such as in pyrosequencing. In embodiment, a nucleotide comprises a label (such as a dye). In embodiments, the label is not associated with any particular nucleotide, but detection of the label identifies whether one or more nucleotides having a known identity were added during an extension step (such as in the case of pyrosequencing). Examples of detectable agents (i.e., labels) include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). The term "cyanine" or "cyanine moiety" as described herein refers to a detectable moiety containing two nitrogen groups separated by a polymethine chain. In embodiments, the cyanine moiety has 3 methine structures (i.e., cyanine 3 or Cy3). In embodiments, the cyanine moiety has 5 methine structures (i.e., cyanine 5 or Cy5). In embodiments, the cyanine moiety has 7 methine structures (i.e., cyanine 7 or Cy7).

The term "nucleoside" refers, in the usual and customary sense, to a glycosylamine including a nucleobase and a five-carbon sugar (ribose or deoxyribose). Non-limiting examples of nucleosides include cytidine, uridine, adenosine, guanosine, thymidine and inosine. Nucleosides may be modified at the base and/or the sugar. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g., polynucleotides contemplated herein include any types of RNA, e.g., mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/ or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

As used herein, the term "removable" group, e.g., a label or a blocking group or protecting group, is used in accordance with its plain and ordinary meaning and refers to a chemical group that can be removed from a nucleotide analogue such that a DNA polymerase can extend the nucleic acid (e.g., a primer or extension product) by the incorporation of at least one additional nucleotide. Removal may be by any suitable method, including enzymatic, chemical, or photolytic cleavage. Removal of a removable group, e.g., a blocking group, does not require that the entire removable group be removed, only that a sufficient portion of it be removed such that a DNA polymerase can extend a nucleic acid by incorporation of at least one additional nucleotide using a nucleotide or nucleotide analogue. In general, the conditions under which a removable group is removed are compatible with a process employing the removable group (e.g., an amplification process or sequencing process).

As used herein, the terms "reversible blocking groups" and "reversible terminators" are used in accordance with their plain and ordinary meanings and refer to a blocking moiety located, for example, at the 3' position of a modified nucleotide and may be a chemically cleavable moiety such as an allyl group, an azidomethyl group or a methoxymethyl group, or may be an enzymatically cleavable group such as a phosphate ester. Non-limiting examples of nucleotide blocking moieties are described in applications WO 2004/018497, WO 96/07669, U.S. Pat. Nos. 7,057,026, 7,541,444, 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group —OR [reversible terminating (capping) group] is linked to the oxygen atom of the 3'-OH of the pentose, while the label is linked to the base, which acts as a reporter and can be cleaved. The 3'-O-blocked reversible terminators are known in the art, and may be, for instance, a 3'-$ONH_2$ reversible terminator, a 3'-O-allyl reversible terminator, or a 3'-O-azidomethyl reversible terminator. In embodiments, the reversible terminator moiety is attached to the 3'-oxygen of the nucleotide, having the formula:

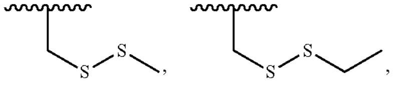

-continued

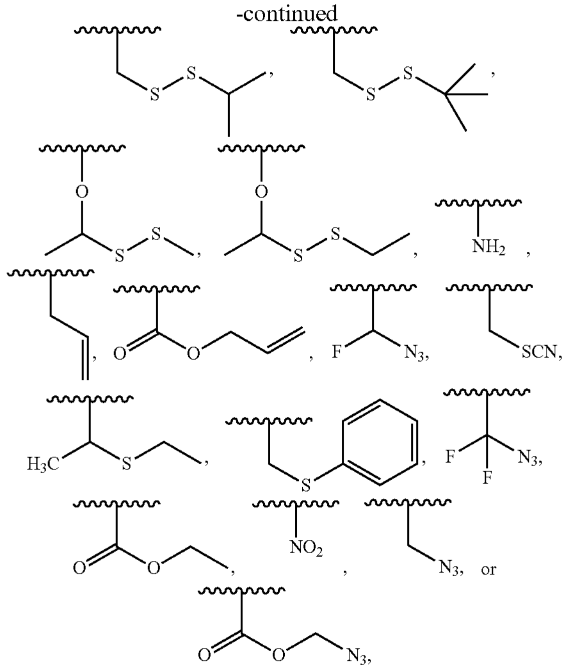

wherein the 3' oxygen of the nucleotide is not shown in the formulae above. The term "allyl" as described herein refers to an unsubstituted methylene attached to a vinyl group (i.e., —$CH$=$CH_2$). In embodiments, the reversible terminator moiety is

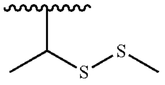 [SMILES: *C(C)SSC]

as described in U.S. Pat. No. 10,738,072, which is incorporated herein by reference for all purposes. For example, a nucleotide including a reversible terminator moiety may be represented by the formula:

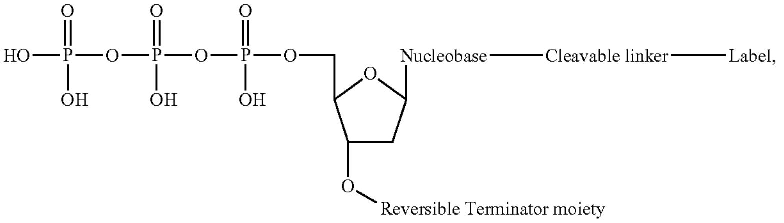

where the nucleobase is adenine or adenine analogue, thymine or thymine analogue, guanine or guanine analogue, or cytosine or cytosine analogue.

In some embodiments, a nucleic acid (e.g., an adapter or a primer) comprises a molecular identifier or a molecular barcode. As used herein, the term "molecular barcode" (which may be referred to as a "tag", a "barcode", a "molecular identifier", an "identifier sequence" or a "unique molecular identifier" (UMI)) refers to any material (e.g., a nucleotide sequence, a nucleic acid molecule feature) that is capable of distinguishing an individual molecule in a large heterogeneous population of molecules. In embodiments, a barcode is unique in a pool of barcodes that differ from one another in sequence, or is uniquely associated with a particular sample polynucleotide in a pool of sample polynucleotides. In embodiments, every barcode in a pool of adapters is unique, such that sequencing reads comprising the barcode can be identified as originating from a single sample polynucleotide molecule on the basis of the barcode alone. In other embodiments, individual barcode sequences may be used more than once, but adapters comprising the duplicate barcodes are associated with different sequences and/or in different combinations of barcoded adaptors, such that sequence reads may still be uniquely distinguished as originating from a single sample polynucleotide molecule on the basis of a barcode and adjacent sequence information (e.g., sample polynucleotide sequence, and/or one or more adjacent barcodes). In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are about 10 to about 50 nucleotides in length, such as about 15 to about 40 or about 20 to about 30 nucleotides in length. In a pool of different barcodes, barcodes may have the same or different lengths. In general, barcodes are of sufficient length and include sequences that are sufficiently different to allow the identification of sequencing reads that originate from the same sample polynucleotide molecule. In embodiments, each barcode in a plurality of barcodes differs from every other barcode in the plurality by at least three nucleotide positions, such as at least 3, 4, 5, 6, 7, 8, 9, 10, or more nucleotide positions. In some embodiments, substantially degenerate barcodes may be known as random. In some embodiments, a barcode may include a nucleic acid sequence from within a pool of known sequences. In some embodiments, the barcodes may be pre-defined. In embodiments, the barcodes are selected to form a known set of barcodes, e.g., the set of barcodes may be distinguished by a particular Hamming distance. In embodiments, each barcode sequence is unique within the known set of barcodes.

The term "nucleobase" or "base" as used herein refers to a purine or pyrimidine compound, or a derivative thereof, that may be a constituent of nucleic acid (i.e., DNA or RNA, or a derivative thereof). In embodiments, the nucleobase is a divalent purine or pyrimidine, or derivative thereof. In embodiments, the nucleobase is a monovalent purine or pyrimidine, or derivative thereof. In embodiments, the base is a derivative of a naturally occurring DNA or RNA base (e.g., a base analog). In embodiments the base is a hybridizing base. In embodiments the base hybridizes to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes cytosine or a derivative thereof (e.g., cytosine analog), guanine or a derivative thereof (e.g., guanine analog), adenine or a derivative thereof (e.g., adenine analog), thymine or a derivative thereof (e.g., thymine analog), uracil or a derivative thereof (e.g., uracil analog), hypoxanthine or a derivative thereof (e.g., hypoxanthine analog), xanthine or a derivative thereof (e.g., xanthine analog), 7-methylguanine or a derivative thereof (e.g., 7-methylguanine analog), deaza-adenine or a derivative thereof (e.g., deaza-adenine analog), deaza-guanine or a derivative thereof (e.g., deaza-guanine), deaza-hypoxanthine or a derivative thereof, 5,6-dihydrouracil or a derivative thereof (e.g., 5,6-dihydrouracil analog), 5-methylcytosine or a derivative thereof (e.g., 5-methylcytosine analog), or 5-hydroxymethylcytosine or a derivative thereof (e.g., 5-hydroxymethylcytosine analog) moieties. In embodiments, the base is adenine, guanine, uracil, cytosine, thymine, hypoxanthine, xanthine, theobromine, caffeine, uric acid, or isoguanine, which may be optionally substituted or modified. In embodiments, the base is adenine, guanine, hypoxanthine, xanthine, theobromine, caffeine, uric acid, or isoguanine, which may be optionally substituted or modified.

In embodiments, a nucleic acid (e.g., an adapter or primer) comprises a sample barcode. In general, a "sample barcode" is a nucleotide sequence that is sufficiently different from other sample barcode to allow the identification of the sample source based on sample barcode sequence(s) with which they are associated. In embodiments, a plurality of nucleotides (e.g., all nucleotides from a particular sample source, or sub-sample thereof) are joined to a first sample barcode, while a different plurality of nucleotides (e.g., all nucleotides from a different sample source, or different subsample) are joined to a second sample barcode, thereby associating each plurality of polynucleotides with a different sample barcode indicative of sample source. In embodiments, each sample barcode in a plurality of sample barcodes differs from every other sample barcode in the plurality by at least three nucleotide positions, such as at least 3, 4, 5, 6, 7, 8, 9, 10, or more nucleotide positions. In some embodiments, substantially degenerate sample barcodes may be known as random. In some embodiments, a sample barcode may include a nucleic acid sequence from within a pool of known sequences. In some embodiments, the sample barcodes may be predefined. In embodiments, the sample barcode includes about 1 to about 10 nucleotides. In embodiments, the sample barcode includes about 3, 4, 5, 6, 7, 8, 9, or about 10 nucleotides. In embodiments, the sample barcode includes about 3 nucleotides. In embodiments, the sample barcode includes about 5 nucleotides. In embodiments, the sample barcode includes about 7 nucleotides. In embodiments, the sample barcode includes about 10 nucleotides. In embodiments, the sample barcode includes about 6 to about 10 nucleotides.

As used herein, the term "biomolecule" refers to an agent (e.g., a compound, macromolecule, or small molecule), and the like derived from a biological system (e.g., an organism). The biomolecule may contain multiple individual components that collectively construct the biomolecule, for example, in embodiments, the biomolecule is a polynucleotide wherein the polynucleotide is composed of nucleotide monomers. The biomolecule may be or may include DNA, RNA, organelles, carbohydrates, lipids, proteins, or any combination thereof. These components may be extracellular. In some examples, the biomolecule may be referred to as a clump or aggregate of combinations of components. In some instances, the biomolecule may include one or more constituents of a cell but may not include other constituents of the cell. In embodiments, a biomolecule is a molecule produced by a biological system (e.g., an organism).

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, *E. Coli* DNA polymerase I, Bacteriophage T4 DNA polymerase, Sequenase, Taq DNA polymerase, DNA polymerase from *Bacillus stearothermophilus*, Bst 2.0 DNA polymerase, 9° N polymerase (exo-)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or Therminator™ IX DNA Polymerase. In embodiments, the polymerase is a protein polymerase. Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g. Therminator γ, 9° N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044). In embodiments, the polymerase is an enzyme described in US 2021/0139884. For example, a polymerase catalyzes the addition of a next correct nucleotide to the 3'-OH group of the primer via a phosphodiester bond, thereby chemically incorporating the nucleotide into the primer. Optionally, the polymerase used in the provided methods is a processive polymerase. Optionally, the polymerase used in the provided methods is a distributive polymerase.

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at either the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the term "incorporating" or "chemically incorporating," when used in reference to a primer and cognate nucleotide, refers to the process of joining the cognate nucleotide to the primer or extension product thereof by formation of a phosphodiester bond.

As used herein, the term "template polynucleotide" or "template nucleic acid" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In the context of selective sequencing, "target polynucleotide(s)" refers to the subset of polynucleotide(s) to be sequenced from within a starting population of polynucleotides.

In embodiments, a target polynucleotide is a cell-free polynucleotide. In general, the terms "cell-free," "circulating," and "extracellular" as applied to polynucleotides (e.g. "cell-free DNA" (cfDNA) and "cell-free RNA" (cfRNA)) are used interchangeably to refer to polynucleotides present in a sample from a subject or portion thereof that can be isolated or otherwise manipulated without applying a lysis step to the sample as originally collected (e.g., as in extraction from cells or viruses). Cell-free polynucleotides are thus unencapsulated or "free" from the cells or viruses from which they originate, even before a sample of the subject is collected. Cell-free polynucleotides may be produced as a byproduct of cell death (e.g., apoptosis or necrosis) or cell shedding, releasing polynucleotides into surrounding body fluids or into circulation. Accordingly, cell-free polynucleotides may be isolated from a non-cellular fraction of blood (e.g., serum or plasma), from other bodily fluids (e.g., urine), or from non-cellular fractions of other types of samples.

As used herein, the term "adjacent," refers to two nucleotide sequences in a nucleic acid, can refer to nucleotide sequences separated by 0 to about 20 nucleotides, more specifically, in a range of about 1 to about 10 nucleotides, or to sequences that directly abut one another. As those of skill in the art appreciate, two nucleotide sequences that that are to ligated together will generally directly abut one another.

A nucleic acid can be amplified by a suitable method. The term "amplification," "amplified," or "amplifying" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof. In some embodiments an amplification reaction comprises a suitable thermal stable polymerase. Thermal stable polymerases are known in the art and are stable for prolonged periods of time, at temperature greater than 80° C. when compared to common polymerases found in most mammals. In certain embodiments the term "amplified"

refers to a method that comprises a polymerase chain reaction (PCR). Conditions conducive to amplification (i.e., amplification conditions) are known and often comprise at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer).

As used herein, bridge-PCR (bPCR) amplification is a method for solid-phase amplification as exemplified by the disclosures of U.S. Pat. Nos. 5,641,658; 7,115,400; and U.S. Patent Publ. No. 2008/0009420, each of which is incorporated herein by reference in its entirety. Bridge-PCR involves repeated polymerase chain reaction cycles, cycling between denaturation, annealing, and extension conditions and enables controlled, spatially-localized, amplification, to generate amplification products (e.g., amplicons) immobilized on a solid support in order to form arrays comprised of colonies (or "clusters") of immobilized nucleic acid molecule.

Amplification according to the present teachings encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA (oligonucleotide ligation assay)/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html-); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18- (2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, PCT Publication No. WO0056927A3, and PCT Publication No. WO9803673A1.

In some embodiments, amplification includes at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can include thermocycling or can be performed isothermally.

As used herein, the term "rolling circle amplification (RCA)" refers to a nucleic acid amplification reaction that amplifies a circular nucleic acid template (e.g., single-stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase. RCA may be performed by using any of the DNA polymerases that are known in the art (e.g., a Phi29 DNA polymerase, a Bst DNA polymerase, or SD polymerase).

A nucleic acid can be amplified by a thermocycling method or by an isothermal amplification method. In some embodiments a rolling circle amplification method is used. In some embodiments amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface or substrate (e.g., a polymer or a particle, or a combination thereof). In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution-based primers can be used. Non-limiting examples of solid phase nucleic acid amplification reactions include interfacial amplification, bridge PCR amplification, emulsion PCR, WildFire amplification (e.g., US patent publication US20130012399), the like or combinations thereof.

As used herein, the terms "cluster" and "colony" are used interchangeably to refer to a discrete site on a solid support that includes a plurality of immobilized polynucleotides and optionally, a plurality of immobilized complementary polynucleotides. The term "clustered array" refers to an array formed from such clusters or colonies. In this context the term "array" is not to be understood as requiring an ordered arrangement of clusters. The term "array" is used in accordance with its ordinary meaning in the art, and refers to a population of different molecules that are attached to one or more solid-phase substrates such that the different molecules can be differentiated from each other according to their relative location. An array can include different molecules that are each located at different addressable features on a solid-phase substrate. The molecules of the array can be nucleic acid primers, nucleic acid probes, nucleic acid templates or nucleic acid enzymes such as polymerases or ligases. Arrays useful in the invention can have densities that ranges from about 2 different features to many millions, billions or higher. The density of an array can be from 2 to as many as a billion or more different features per square cm. For example an array can have at least about 100 features/$cm^2$, at least about 1,000 features/$cm^2$, at least about 10,000 features/$cm^2$, at least about 100,000 features/$cm^2$, at least about 10,000,000 features/$cm^2$, at least about 100,000,000 features/$cm^2$, at least about 1,000,000,000 features/$cm^2$, at least about 2,000,000,000 features/$cm^2$ or higher. In embodiments, the arrays have features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher.

As used herein, the terms "overlapping amplification cluster" and "overlapping cluster" refer to a site (e.g., a discrete site) on in a polymer layer that includes a plurality of polyclonal immobilized polynucleotides, and optionally a plurality of immobilized complementary polynucleotides. In embodiments, to generate an overlapping amplification cluster, multiple template polynucleotides are immobilized within one spot polymer layer and subsequently amplified. In an overlapping amplification cluster, a fraction of the surface is occupied by copies of one template polynucleotide species, and other fractions of the surface are occupied of copies of a different template polynucleotide. In embodiments, each immobilized polynucleotide in an overlapping amplification cluster is included in a detection region. In embodiments, an overlapping amplification cluster is included in one or more detection regions. As used herein, the term "detection region" refers to a location where at least one analyte molecule is present. A site can contain only a single analyte molecule or it can contain a population of several analyte molecules of the same species. In some embodiments, a site can include multiple different analyte molecule species, each species being present in one or more copies. Sites of an array are typically discrete. The discrete sites can be contiguous, or they can have spaces between each other. In embodiments, the same template polynucleotide sequence may be present in the same location (e.g., same x-y coordinates and/or geographic location). In embodiments, the same template polynucleotide sequence may be present in different locations (e.g., different x-y coordinates and/or geographic location). In embodiments, the overlapping cluster may be referred to as a feature. In embodiments, multiple template polynucleotides seed one spot (i.e., a feature) of a patterned array or unpatterned solid support. In embodiments, a fraction of the surface area within the feature is occupied by copies of one template, and another fraction of the patterned spot can be occupied by copies of another template. The fractions of the template polynucleotides within the feature are inherently stochastic and governed by Poisson statistics.

Detection can be carried out at ensemble or single molecule levels on an array. Ensemble level detection is detection that occurs in a way that several copies of a single template sequence (e.g. multiple amplicons of a template) are detected at each individual site and individual copies at the site are not distinguished from each other. Thus, ensemble detection provides an average signal from many copies of a particular template sequence at the site. For example, the site can contain at least 10, 100, 1000 or more copies of a particular template sequence. Of course, a site can contain multiple different template sequences each of which is present as an ensemble. Alternatively, detection at a single molecule level includes detection that occurs in a way that individual template sequences are individually resolved on the array, each at a different site. Thus, single molecule detection provides a signal from an individual molecule that is distinguished from one or more signals that may arise from a population of molecules within which the individual molecule is present. Of course, even in a single molecule array, a site can contain several different template sequences (e.g., two or more template sequence regions located along a single nucleic acid molecule).

An array of sites (e.g., an array of features) can appear as a grid of spots or patches. The sites can be located in a repeating pattern or in an irregular non-repeating pattern. Particularly useful patterns are hexagonal patterns, rectilinear patterns, grid patterns, patterns having reflective symmetry, patterns having rotational symmetry, or the like. Asymmetric patterns can also be useful; in embodiments, the array of features are present in an asymmetric pattern.

The size of the sites and/or spacing between the sites in an array can vary to achieve high density, medium density, or lower density. High density arrays are characterized as having sites with a pitch that is less than about 15 μm. Medium density arrays have sites with a pitch that is about 15 to 30 μm, while low density arrays have a pitch that is greater than 30 μm. An array useful in some embodiments can have sites with a pitch that is less than 100 μm, 50 μm, 10 μm, 5 μm, 1 μm, or 0.5 μm. An embodiment of the methods set forth herein can be used to image an array at a resolution sufficient to distinguish sites at the above densities or density ranges. However, the detecting step will typically use a detector having a spatial resolution that is too low to resolve points at a distance equivalent to the spacing between a first template (or first primer extension product hybridized thereto) and a second template (or second primer extension product hybridized thereto) of an overlapping cluster at an individual site. In particular embodiments, sites of an array can each have an area that is larger than about 100 $nm^2$, 250 $nm^2$, 500 $nm^2$, 1 $\mu m^2$, 2.5 $\mu m^2$, 5 $\mu m^2$, 10 $\mu m^2$, 100 $\mu m^2$, or 500 $\mu m^2$. Alternatively or additionally, sites of an array can each have an area that is smaller than about 1 $mm^2$, 500 $\mu m^2$, 100 $\mu m^2$, 25 $\mu m^2$, 10 $\mu m^2$, 5 $\mu m^2$, 1 $\mu m^2$, 500 $nm^2$, or 100 $nm^2$. Indeed, a site can have a size that is in a range between an upper and lower limit selected from those exemplified above.

Generally, an array will have sites with different nucleic acid sequence content. In embodiments, each of a plurality of sites of the array contains different ratios of a population of template polynucleotides, wherein each population of template polynucleotides contains different sequencing primer binding sites. Accordingly, each of the sites in an array can contain a nucleic acid sequence that is unique compared to the nucleic acid sequences at the other sites in the array. However, in some cases an array can have redundancy such that two or more sites have the same nucleic acid content.

As used herein, the term "each," when used in reference to a collection of items, is intended to identify an individual item in the collection but does not necessarily refer to every item in the collection. Exceptions can occur if explicit disclosure or context clearly dictates otherwise.

Provided herein are methods and compositions for analyzing a sample (e.g., sequencing nucleic acids within a sample). A sample (e.g., a sample comprising nucleic acid) can be obtained from a suitable subject. A sample can be isolated or obtained directly from a subject or part thereof. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid).

In some embodiments, a sample includes one or more nucleic acids, or fragments thereof. A sample can include nucleic acids obtained from one or more subjects. In some embodiments a sample includes nucleic acid obtained from a single subject. In some embodiments, a sample includes a mixture of nucleic acids. A mixture of nucleic acids can include two or more nucleic acid species having different nucleotide sequences, different fragment lengths, different origins (e.g., genomic origins, cell or tissue origins, subject origins, the like or combinations thereof), or combinations thereof.

A subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a human subject. A subject can be a patient (e.g., a human patient). In some embodiments a subject is suspected of having a genetic variation or a disease or condition associated with a genetic variation.

The methods and kits of the present disclosure may be applied, mutatis mutandis, to the sequencing of RNA, or to determining the identity of a ribonucleotide.

As used herein, the terms "sequencing", "sequence determination", and "determining a nucleotide sequence", are used in accordance with their ordinary meaning in the art, and refer to determination of partial as well as full sequence information of the nucleic acid being sequenced, and particular physical processes for generating such sequence information. That is, the term includes sequence comparisons, fingerprinting, and like levels of information about a target nucleic acid, as well as the express identification and ordering of nucleotides in a target nucleic acid. The term also includes the determination of the identification, ordering, and locations of one, two, or three of the four types of nucleotides within a target nucleic acid. Sequencing produces one or more sequencing reads. In some embodiments, a sequencing process described herein comprises contacting a template and an annealed primer with a suitable polymerase under conditions suitable for polymerase extension and/or sequencing. The sequencing methods are preferably carried out with the target polynucleotide arrayed on a solid substrate within a particular polymer layer. Multiple target polynucleotides can be immobilized within a polymer layer through linker molecules, or can be attached to particles, e.g., microspheres, which can also be attached to a solid substrate.

The term "multiplexing" as used herein refers to an analytical method in which the presence and/or amount of multiple targets, e.g., multiple nucleic acid target sequences, can be assayed simultaneously by using the methods and devices as described herein, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

Complementary single stranded nucleic acids and/or substantially complementary single stranded nucleic acids can hybridize to each other under hybridization conditions, thereby forming a nucleic acid that is partially or fully double stranded. All or a portion of a nucleic acid sequence may be substantially complementary to another nucleic acid sequence, in some embodiments. As referred to herein, "substantially complementary" refers to nucleotide sequences that can hybridize with each other under suitable hybridization conditions. Hybridization conditions can be altered to tolerate varying amounts of sequence mismatch within complementary nucleic acids that are substantially complementary. Substantially complementary portions of nucleic acids that can hybridize to each other can be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. In some embodiments substantially complementary portions of nucleic acids that can hybridize to each other are 100% complementary. Nucleic acids, or portions thereof, that are configured to hybridize to each other often comprise nucleic acid sequences that are substantially complementary to each other.

As used herein, the term "sequencing reaction mixture" is used in accordance with its plain and ordinary meaning and refers to an aqueous mixture that contains the reagents necessary to allow dNTP or dNTP analogue (e.g., a modified nucleotide) to add a nucleotide to a DNA strand by a DNA polymerase. In embodiments, the sequencing reaction mixture includes a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton X), a chelator (e.g., EDTA), and/or salts (e.g., ammonium sulfate, magnesium chloride, sodium chloride, or potassium chloride).

As used herein, the term "sequencing cycle" is used in accordance with its plain and ordinary meaning and refers to incorporating one or more nucleotides (e.g., a compound described herein) to the 3' end of a polynucleotide with a polymerase, and detecting one or more labels that identify the one or more nucleotides incorporated. The sequencing may be accomplished by, for example, sequencing by synthesis, sequencing by binding, sequencing by ligation, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

As used herein, the term "extension" or "elongation" is used in accordance with their plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) DNA strand.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode sequence and a template nucleotide sequence. In embodiments, a sequencing read includes reading a template nucleotide sequence. In embodiments, a sequencing read includes reading a barcode and not a template nucleotide sequence. Reads of length 20-40 base pairs (bp) are referred to as ultra-short. Typical sequencers produce read lengths in the range of 100-500 bp. Read length is a factor which can affect the results of biological studies. For example, longer read lengths improve the resolution of de novo genome assembly and detection of structural variants. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence. In embodiments, a sequencing read includes a computationally derived string corresponding to the detected label. In some embodiments, a sequencing read may include 500, 600, 700, 800, 900, 1,000, 1,100, 1,200, 1,300, 1,400, 1,500, or more nucleotide bases. In embodiments, a sequencing read is a string of characters representing the sequence of nucleotides. In embodiments, the length of a sequencing read corresponds to the length of the target sequence. In embodiments, the length of a sequencing read corresponds to the number of sequencing cycles. A sequencing read may be subjected to initial processing (often termed "pre-processing") prior to annotation. Pre-processing includes filtering out low-quality sequences, sequence trimming to remove continuous low-quality nucleotides, merging paired-end sequences, or identifying and filtering out PCR repeats using known techniques in the art. The sequenced reads may then be assembled and aligned using bioinformatic algorithms known in the art. A sequencing read may be aligned to a reference sequence. In embodiments, a sequencing read includes a computationally derived string corresponding to the detected complementary nucleotide (e.g., a labeled nucleotide). The sequence reads are optionally stored in an appropriate data structure for further evaluation. In embodiments, a first sequencing reaction can generate a first sequencing read. The first sequencing read can provide the sequence of a first region of the polynucleotide fragment. In some embodiments, the nucleic acid template is optionally subjected to one or more additional rounds of sequencing using additional sequencing primers, thereby generating additional sequencing reads.

As used herein, the term "polymer" refers to macromolecules having one or more structurally unique repeating units. The repeating units are referred to as "monomers," which are polymerized for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer.

Polymers can be hydrophilic, hydrophobic or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically copolymers having hydrophilic segment(s) and hydrophobic segment(s). Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic. In some embodiments, the alternating layers of polymeric gels described comprise a hydrophilic material.

As used herein, the term "hydrogel" or "hydrogel carrier" refers to a three-dimensional polymeric structure that is substantially insoluble in water, but which is capable of absorbing and retaining water (e.g., large quantities of water) to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can be comprised of natural or synthetic polymers. Hydrogels can contain over 99% water and may comprise natural or synthetic polymers, or a combination thereof. Hydrogels also possess a degree of flexibility very similar to natural tissue, due to their significant water content. A detailed description of suitable hydrogels may be found in published U.S. patent application 20100055733, herein specifically incorporated by reference. By "hydrogel subunits" or "hydrogel precursors" is meant hydrophilic monomers, prepolymers, or polymers that can be crosslinked, or "polymerized", to form a three-dimensional (3D) hydrogel network. In some embodiments, the alternating layers of polymeric gels described herein are hydrogels.

Hydrogels may be prepared by cross-linking hydrophilic biopolymers or synthetic polymers. Thus, in some embodiments, the hydrogel may include a crosslinker. As used herein, the term "crosslinker" refers to a molecule that can form a three-dimensional network when reacted with the appropriate base monomers. Examples of the hydrogel polymers, which may include one or more crosslinkers, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-(meth)acrylate, PEO—PPO-PEO copolymers (Pluronics), poly(phosphazene), poly(methacrylates), poly(N-vinylpyrrolidone), PL(G)A-PEO-PL(G)A copolymers, poly(ethylene imine), polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations thereof. Thus, for example, a combination may include a polymer and a crosslinker, for example polyethylene glycol (PEG)-thiol/PEG-acrylate, acrylamide/N,N'-bis(acryloyl)cystamine (BACy), or PEG/polypropylene oxide (PPO). In embodiments, the hydrogel includes chemical crosslinks (e.g., intermolecular or intramolecular joining of two or more molecules by a covalent bond) and may be referred to as a chemical hydrogel. In embodiments, the hydrogel includes physical crosslinks (e.g., intermolecular or intramolecular joining of two or more molecules by a non-covalent bond) and may be referred to as a physical hydrogel. In embodiments, the physical hydrogel include one or more crosslinks including hydrogen bonds, hydrophobic interactions, and/or polymer chain entanglements.

The terms "iniferter mediated polymerization" and the like refer, in the usual and customary sense, to polymerization employing an "iniferter" which, as known in the art, is a chemical compound that simultaneously acts as initiator, transfer agent, and terminator in controlled free radical polymerization reactions, e.g., dithiocarbamates. See e.g., Otsu, T., & Yashida, M., *Mackromol. Chem., Rapid Commun.,* 1982, 3:127-132.

The terms "stable free radical mediated polymerization," "SRFP" and the like refer, in the usual and customary sense, to polymerization reactions wherein the coupling of the stable free radical with the polymeric radical is sufficiently reversible that the termination step is reversible, and the propagating radical concentration can be limited to levels that allow for controlled polymerization. See e.g., Veregin, R. P. N., et al., *Macromolecules* 1993, 26:5316-5320.

The terms "atom transfer radical polymerization," "ATRP" and the like refer, in the usual and customary sense, to methods of polymerization employing a transition metal catalyst, wherein the atom transfer step is the key step in the reaction responsible for uniform polymer chain growth. See e.g., Kato, M., et al., *Macromolecules* 1995, 28:1721-1723; Wang, J. & Matyjaszewski, K., *J. Am. Chem. Soc.* 1995, 117:5614-5615.

The terms "reversible addition fragmentation chain transfer polymerization," "RAFT" and the like refer, in the usual and customary sense, to methods of polymerization which use a chain transfer agent in the form of a thiocarbonylthio compound or the like to afford control over the generated molecular weight and polydispersity during a free-radical polymerization. See e.g., Yeole, N., *Synlett.* 2010(10): 1572-1573; Moad, G., et al., *Aust. J. Chem.,* 2005, 58:379-410.

As used herein, the term "substrate" refers to a solid support material. The substrate can be non-porous or porous. The substrate can be rigid or flexible. As used herein, the terms "solid support" and "solid surface" refers to discrete solid or semi-solid surface. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. Solid supports may be in the form of discrete particles, which alone does not imply or require any particular shape. The term "particle" means a small body made of a rigid or semi-rigid material. A nonporous substrate generally provides a seal against bulk flow of liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. Particularly useful solid supports for some embodiments have at least one surface located within a flow cell. Solid surfaces can also be varied in their shape depending on the application in a method described herein. For example, a solid surface useful herein can be planar, or contain regions which are concave or convex. In embodiments, the geometry of the concave or convex regions (e.g., wells) of the solid surface conform to the size and shape of the particle (e.g., see FIG. 2C) to maximize the contact between as substantially circular particle. In embodiments, the wells of an array are randomly located such that nearest neighbor features have random spacing between each other. Alternatively, in embodiments the spacing between the wells can be ordered, for example, forming a regular pattern. The term solid substrate is encompassing of a substrate (e.g., a flow cell) having a surface comprising a polymer coating covalently attached thereto. In embodiments, the solid substrate is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456:53-59 (2008). In certain embodiments a substrate comprises a surface (e.g., a surface of a flow cell, a surface of a tube, a surface of a chip), for example a metal surface (e.g., steel, gold, silver, aluminum, silicon and copper). In embodiments a substrate (e.g., a substrate surface) is coated and/or comprises functional groups and/or inert materials. In certain embodiments a substrate comprises a bead, a chip, a capillary, a plate, a membrane, a wafer (e.g., silicon wafers), a comb, or a pin for example. In some embodiments a substrate comprises a bead and/or a nanoparticle. A substrate can be made of a suitable material, non-limiting examples of which include a plastic or a suitable polymer (e.g., polycarbonate, poly(vinyl alcohol), poly(divinylbenzene), polystyrene, polyamide, polyester, polyvinylidene difluoride (PVDF), polyethylene, polyurethane, polypropylene, and the like), borosilicate, glass, nylon, Wang resin, Merrifield resin, metal (e.g., iron, a metal alloy, sepharose, agarose, polyacrylamide, dextran, cellulose and the like or combinations thereof. In embodiments a substrate comprises a magnetic material (e.g., iron, nickel, cobalt, platinum, aluminum, and the like). In embodiments a substrate comprises a magnetic bead (e.g., DYNABEADS®, hematite, AMPure XP). Magnets can be used to purify and/or capture nucleic acids bound to certain substrates (e.g., substrates comprising a metal or magnetic material). The flow cell is typically a glass slide containing small fluidic channels (e.g., a glass slide 75 mm×25 mm×1 mm having one or more channels), through which sequencing solutions (e.g., polymerases, nucleotides, and buffers) may traverse. Though typically glass, suitable flow cell materials may include polymeric materials, plastics, silicon, quartz (fused silica), Borofloat® glass, silica, silica-based materials, carbon, metals, an optical fiber or optical fiber bundles, sapphire, or plastic materials such as COCs and epoxies. The particular material can be selected based on properties desired for a particular use. For example, materials that are transparent to a desired wavelength of radiation are useful for analytical techniques that will utilize radiation of the desired wavelength. Conversely, it may be desirable to select a material that does not pass radiation of a certain wavelength (e.g., being opaque, absorptive, or reflective). In embodiments, the material of the flow cell is selected due to the ability to conduct thermal energy. In embodiments, a flow cell includes inlet and outlet ports and a flow channel extending there between. In embodiments, the solid support is an unpatterned solid support. The term "unpatterned solid support" as used herein refers to a solid support with a uniform polymer surface including, for example, amplification primers randomly distributed throughout the polymer surface. This is in contrast to a patterned solid support, wherein amplification primers, for example, as localized to specific regions of the surface, such as to wells in an array. In embodiments, an unpatterned solid support does not include organized surface features such as wells, pits, channels, ridges, raised regions, pegs, posts or the like. In embodiments, the surface of an unpatterned solid support does not contain interstitial regions. In embodiments, an unpatterned solid support includes a polymer (e.g., a hydrophilic polymer). In certain embodiments, the unpatterned solid support includes a plurality of oligonucleotides (e.g., primer oligonucleotides) randomly distributed throughout the polymer (e.g., the plurality of primer oligonucleotides are covalently attached to the polymer in a random distribution, as illustrated in FIGS. 8D-8F). An unpatterned solid support may be, for example, a glass slide including a polymer coating (a hydrophilic polymer coating).

The term "surface" is intended to mean an external part or external layer of a substrate. The surface can be in contact with another material such as a gas, liquid, gel, polymer, organic polymer, second surface of a similar or different material, metal, or coat. The surface, or regions thereof, can be substantially flat. The substrate and/or the surface can have surface features such as wells, pits, channels, ridges, raised regions, pegs, posts or the like.

As used herein, the term "channel" refers to a passage in or on a substrate material that directs the flow of a fluid. A channel may run along the surface of a substrate, or may run through the substrate between openings in the substrate. A channel can have a cross section that is partially or fully surrounded by substrate material (e.g., a fluid impermeable substrate material). For example, a partially surrounded cross section can be a groove, trough, furrow or gutter that inhibits lateral flow of a fluid. The transverse cross section of an open channel can be, for example, U-shaped, V-shaped, curved, angular, polygonal, or hyperbolic. A channel can have a fully surrounded cross section such as a tunnel, tube, or pipe. A fully surrounded channel can have a rounded, circular, elliptical, square, rectangular, or polygonal cross section. In particular embodiments, a channel can be located in a flow cell, for example, being embedded within the flow cell. A channel in a flow cell can include one or more windows that are transparent to light in a particular region of the wavelength spectrum. In embodiments, the channel contains one or more polymers of the disclosure. In embodiments, the channel is filled by the one or more polymers, and flow through the channel (e.g., as in a sample fluid) is directed through the polymer in the channel. In embodiments, the assay is in a channel of a flow cell.

The terms "particle" and "bead" are used interchangeably and mean a small body made of a rigid or semi-rigid material. The body can have a shape characterized, for example, as a sphere, oval, microsphere, or other recognized particle shape whether having regular or irregular dimensions. As used herein, the term "discrete particles" refers to physically distinct particles having discernible boundaries. The term "particle" does not indicate any particular shape. The shapes and sizes of a collection of particles may be different or about the same (e.g., within a desired range of dimensions, or having a desired average or minimum dimension). A particle may be substantially spherical (e.g., microspheres) or have a non-spherical or irregular shape, such as cubic, cuboid, pyramidal, cylindrical, conical, oblong, or disc-shaped, and the like. In embodiments, the particle has the shape of a sphere, cylinder, spherocylinder, or ellipsoid.

As used herein, the term "discrete particles" refers to physically distinct particles having discernible boundaries. Discrete particles collected in a container and contacting one another will define a bulk volume containing the particles, and will typically leave some internal fraction of that bulk volume unoccupied by the particles, even when packed closely together.

A "nanoparticle," as used herein, is a particle wherein the longest diameter is less than or equal to 1000 nanometers. Nanoparticles may be composed of any appropriate material. Nanoparticles may be composed of at least two distinct materials, one material (e.g., the MOF carrier) forms the core and the other material forms the shell (e.g., copolymer) surrounding the core. In embodiments, the nanoparticle is composed of a copolymer described herein. In embodiments, a nanoparticle has a shortest diameter greater than or equal to 1 nanometer (e.g., diameter from 1 to 1000 nanometers). In contrast to a functionalized particle, an unmodified particle refers to a particle which has not been further functionalized. Thus, for example, an unmodified particle does not include a nitrogen containing moiety (e.g., terminal amine moieties). For example, an unmodified nanoparticle refers to nanoparticle as synthesized without post hoc functionalization. As used herein, the terms "bare particle" and "unmodified particle" are synonymous and interchangeable.

A functionalized particle, as used herein, may refer to the post hoc conjugation (i.e. conjugation after the formation of the particle) of a moiety to a functional group on the surface of a particle. For example, a particle may be further functionalized to include additional atoms (e.g., nitrogen) or chemical entities (e.g., polymeric moieties, polymerization initiators, or bioconjugate group).

Lengths and sizes of nanoparticles and functionalized particles as described herein may be measured using Transmission Electron Microscopy. For example, transmission electron microscopy measurements of the various particle samples may be drop coated (5 μL) onto 200 mesh copper EM grids, air-dried and imaged using a FEI Tecnai 12 TEM equipped with a Gatan Ultrascan 2K CCD camera at an accelerating voltage of 120 kV. The average size distributions of the particles may then be obtained from the TEM images using Image J software that were plotted using software (e.g., Origin Pro 8) to obtain the histogram size distributions of the particles. In embodiment, the length of a nanoparticle refers to the longest dimension of the particle.

The presence of the polynucleotide primer on the shell polymer surrounding the core permits a nucleic acid amplification reaction to take place. In embodiments, the cores are "surrounded" by the shell polymer in the sense that the shell polymer completely covers each core, and no core is in direct contact with any other core. The shell layer may enclose (e.g., surround, encapsulate, envelope) a core. In embodiments, each core surrounded by the shell polymer forms a discrete particle, the outer surface of which is defined by the shell polymer. In embodiments, the shells of discrete core-shell particles suspended in a container (e.g., a well, tube, or flow cell) expands, to fill any space between adjacent particles. In such cases, the boundaries of individual particles may no longer be readily discernable, but each core remains separated from each other by the shell polymer surrounding each, which can be readily observed by, e.g., detecting products of a nucleic acid amplification reaction. The shell polymer may itself surround a degradable particle core. The core can be comprised of a variety of materials, including but not limited to a polymer, inorganic material, or hybrid of organic-inorganic material, such as a metal-organic framework (MOF carrier). The degradable particle core may be a hydrophobic particle core made through emulsion or latex. In embodiments, the degradable particle core is a MOF carrier such as Zeolitic Imidazolate Framework (e.g., ZIF-8). In embodiments, the degradable particle core is a hydrophobic particle such as polystyrene (PS) or polymethyl methacrylate (PMMA). The term "support particle" as used herein may refer to any particle or substance having a diameter in the micrometer range, such as a "microparticle," which typically has a diameter of approximately 1 μm and higher, or a "nanoparticle," which typically has a diameter of 1 nm to 1 μm. The degradable particle core, may be referred to herein as a nanoparticle core wherein the longest diameter is less than 1000 nanometers. Lengths and sizes of particles and their surrounding cores as described herein may be measured using Transmission Electron Microscopy (TEM). In embodiments, the degradable particle core includes a plurality of oligonucleotide moieties covalently attached to the degradable particle core particle via a polymeric bioconjugate linker. In embodiments, the bioconjugate linker is formed via a reaction between a particle polymer including a first bioconjugate reactive moiety and an oligonucleotide including a second bioconjugate reactive moiety. In embodiments, the degradable particle core is porous.

As used herein, the term "MOF" is used in accordance with its ordinary meaning in the art and refers to a metal-organic framework. A MOF is a type of porous material comprised of metal containing nodes and organic ligands linked through coordination bonds. The structure and topology of MOFs can be designed and tailored so that the MOF can form one-, two-, or three-dimensional structures. The modular nature of MOFs allows for great synthetic tunability so properties such as porosity, stability, particle morphology and conductivity can be tailored for specific applications including encapsulation or release of guest molecules. The organic ligands used in MOFs are also referred to as "linkers" and are typically mono-, di-, tri-, or tetravalent ligands. The choice of metal and linker dictates the structure and properties of the MOF. For example, the metal's coordination preference can influence the size and shape of the pores in the MOF through the metal's preference for number and orientation of binding ligands. A MOF typically has potential voids between the organic ligands which make them valuable in applications such as drug delivery, bio-storage and bio-catalysis. Further MOFs can undergo post-synthetic modification to further tune properties through swapping, altering or removing linker or node components in the framework. The MOF can be modified using a "modulator" or "modulating agent". The modulator competes with the organic linkers to bind to the metal center. In doing so, this prevents formation of impurities and slows down the reaction, allowing for increased reproducibility and crystallinity of the final product. Compounds that can act as modulators include but are not limited to CTAB, 1-methylimidazole, sodium formate and n-butylamine. A MOF can be degraded to release the compound(s) and/or material(s) encapsulated by the MOF. A MOF can be degraded in response to changes in pH, temperature or light. Examples of MOF structures are zinc imidazolate framework (e.g., ZIF-8), Zr based MOFs, mesoporous iron (III) carboxylate MIL-100(Fe).

As used herein, the term "ZIF-8" refers to a zeolitic imidazolate framework, which is a type of MOF. A ZIF-8 is composed of metal cation $Zn^{2+}$ linked to the 2-methylimidazolate ligand species. On-demand release of material (i.e., controlled degradation) from a ZIF-8 carrier occurs in the presence of an external stimulus such as pH and at high efficiency (up to 100%) and/or at high temperature conditions. The ZIF-8 can be degraded by lowering the pH with an acid such as HCl, or by raising the pH with a base such as NaOH, and/or in the presence of degrading compounds such as phosphate, thereby eroding or dissolving the MOF.

The term "microplate", "microtiter plate" or "multiwell plate" as used herein, refers to a substrate comprising a surface, the surface including a plurality of reaction chambers separated from each other by interstitial regions on the surface. In embodiments, the microplate has dimensions as provided and described by American National Standards Institute (ANSI) and Society for Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012, which are incorporated herein by reference. The dimensions of the microplate as described herein and the arrangement of the reaction chambers may be compatible with an established format for automated laboratory equipment. In embodiments, the device described herein provides methods for high-throughput screening. High-throughput screening (HTS) refers to a process that uses a combination of modern robotics, data processing and control software, liquid handling devices, and/or sensitive detectors, to efficiently process a large amount of (e.g., thousands, hundreds of thousands, or millions) samples in biochemical, genetic, or pharmacological experiments, either in parallel or in sequence, within a reasonably short period of time (e.g., days). Preferably, the process is amenable to automation, such as robotic simultaneous handling of 96 samples, 384 samples, 1536 samples or more. A typical HTS robot tests up to 100,000 to a few hundred thousand compounds per day. The samples are often in small volumes, such as no more than 1 mL, 500 μl, 200 μl, 100 μl, 50 μl or less. Through this process, one can rapidly identify active compounds, small molecules, antibodies, proteins or polynucleotides in a cell.

The reaction chambers may be provided as wells (alternatively referred to as reaction chambers), for example a microplate may contain 2, 4, 6, 12, 24, 48, 96, 384, or 1536 sample wells. In embodiments, the 96 and 384 wells are arranged in a 2:3 rectangular matrix. In embodiments, the 24 wells are arranged in a 3:8 rectangular matrix. In embodiments, the 48 wells are arranged in a 3:4 rectangular matrix. In embodiments, the reaction chamber is a microscope slide (e.g., a glass slide about 75 mm by about 25 mm). In embodiments the slide is a concavity slide (e.g., the slide includes a depression). In embodiments, the slide includes a coating for enhanced cell adhesion (e.g., poly-L-lysine, silanes, carbon nanotubes, polymers, epoxy resins, or gold). In embodiments, the microplate is about 5 inches by about 3.33 inches, and includes a plurality of 5 mm diameter wells. In embodiments, the microplate is about 5 inches by about 3.33 inches, and includes a plurality of 6 mm diameter wells. In embodiments, the microplate is about 5 inches by about 3.33 inches, and includes a plurality of 7 mm diameter wells. In embodiments, the microplate is about 5 inches by about 3.33 inches, and includes a plurality of 7.5 mm diameter wells. In embodiments, the microplate is 5 inches by 3.33 inches, and includes a plurality of 7.5 mm diameter wells. In embodiments, the microplate is about 5 inches by about 3.33 inches, and includes a plurality of 8 mm diameter wells. In embodiments, the microplate is a flat glass or plastic tray in which an array of wells are formed, wherein each well can hold between from a few microliters to hundreds of microliters of fluid reagents and samples.

The term "well" refers to a discrete concave feature in a substrate having a surface opening that is completely surrounded by interstitial region(s) of the surface. Wells can have any of a variety of shapes at their opening in a surface including but not limited to round, elliptical, square, polygonal, or star shaped (i.e., star shaped with any number of vertices). The cross section of a well taken orthogonally with the surface may be curved, square, polygonal, hyperbolic, conical, or angular. The wells of a microplate are available in different shapes, for example F-Bottom: flat bottom; C-Bottom: bottom with minimal rounded edges; V-Bottom: V-shaped bottom; or U-Bottom: U-shaped bottom. In embodiments, the well is substantially square. In embodiments, the well is square. In embodiments, the well is F-bottom. In embodiments, the microplate includes 24 substantially round flat bottom wells. In embodiments, the microplate includes 48 substantially round flat bottom wells. In embodiments, the microplate includes 96 substantially round flat bottom wells. In embodiments, the microplate includes 384 substantially square flat bottom wells.

The discrete regions (i.e., features, wells) of the microplate may have defined locations in a regular array, which may correspond to a rectilinear pattern, circular pattern, hexagonal pattern, or the like. In embodiments, the pattern of wells includes concentric circles of regions, spiral patterns, rectilinear patterns, hexagonal patterns, and the like. In embodiments, the pattern of wells is arranged in a rectilinear or hexagonal pattern A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. In embodiments, interstitial regions have a surface material that differs from the surface material of the wells (e.g., the interstitial region contains a photoresist and the surface of the well is glass). In embodiments, interstitial regions have a surface material that is the same as the surface material of the wells (e.g., both the surface of the interstitial region and the surface of well contain a polymer or copolymer).

As used herein, the term "selective" or "selectivity" or the like of a compound refers to the substance's ability to discriminate between molecular targets. As used herein, the terms "specific", "specifically", "specificity", or the like of a compound refers to the substance's ability to cause a particular action, such as binding, to a particular molecular target with minimal or no action to other substances (e.g., an antibody and antigen). For example, a chemical reagent may selectively modify one nucleotide type in that it reacts with one nucleotide type (e.g., cytosines) and not other nucleotide types (e.g., adenine, thymine, or guanine). When used in the context of sequencing, such as in "selectively sequencing," this term refers to sequencing one or more target polynucleotides from an original starting population of polynucleotides, and not sequencing non-target polynucleotides from the starting population. Typically, selectively sequencing one or more target polynucleotides involves differentially manipulating the target polynucleotides based on known sequence. For example, target polynucleotides may be hybridized to a probe oligonucleotide that may be labeled (such as with a member of a binding pair) or bound to a surface. In embodiments, hybridizing a target polynucleotide to a probe oligonucleotide includes the step of displacing one strand of a double-stranded nucleic acid. Probe-hybridized target polynucleotides may then be separated from non-hybridized polynucleotides, such as by removing probe-bound polynucleotides from the starting population or by washing away polynucleotides that are not bound to a probe. The result is a selected subset of the starting population of polynucleotides, which is then subjected to sequencing, thereby selectively sequencing the one or more target polynucleotides.

The terms "bind" and "bound" as used herein are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules (e.g., as in a substrate, bound to a first antibody, bound to an analyte, bound to a second antibody), thereby forming a complex. As used herein, the term "attached" refers to the state of two things being joined, fastened, adhered, connected or bound to each other. For example, a sample such as a cell or tissue, can be attached to a material, such as a hydrogel, polymer, or solid support, by a covalent or non-covalent bond. In embodiments, attachment is a covalent attachment.

"Specific binding" is where the binding is selective between two molecules. A particular example of specific binding is that which occurs between an antibody and an antigen. Typically, specific binding can be distinguished from non-specific when the dissociation constant (KD) is less than about $1\times10^{-5}$ M or less than about $1\times10^{-6}$ M or $1\times10^{-7}$ M. Specific binding can be detected, for example, by ELISA, immunoprecipitation, coprecipitation, with or without chemical crosslinking, two-hybrid assays and the like.

The term "adapter" as used herein refers to any linear oligonucleotide that can be ligated to a nucleic acid molecule, thereby generating nucleic acid products that can be sequenced on a sequencing platform (e.g., an Illumina or Singular Genomics sequencing platform). In embodiments, adapters include two reverse complementary oligonucleotides forming a double-stranded structure. In embodiments, an adapter includes two oligonucleotides that are complementary at one portion and mismatched at another portion, forming a Y-shaped or fork-shaped adapter that is double stranded at the complementary portion and has two overhangs at the mismatched portion. Since Y-shaped adapters have a complementary, double-stranded region, they can be considered a special form of double-stranded adapters. When this disclosure contrasts Y-shaped adapters and double stranded adapters, the term "double-stranded adapter" or "blunt-ended" is used to refer to an adapter having two strands that are fully complementary, substantially (e.g., more than 90% or 95%) complementary, or partially complementary. In embodiments, adapters include sequences that bind to sequencing primers. In embodiments, adapters include sequences that bind to immobilized oligonucleotides (e.g., primer sequences) or reverse complements thereof. In embodiments, the adapter is substantially non-complementary to the 3' end or the 5' end of any target polynucleotide present in the sample. In embodiments, the adapter can include a sequence that is substantially identical, or substantially complementary, to at least a portion of a primer, for example a universal primer. In embodiments, the adapter can include an index sequence (also referred to as barcode or tag) to assist with downstream error correction, identification or sequencing.

As used herein, the term "hairpin adapter" refers to a polynucleotide including a double-stranded stem portion and a single-stranded hairpin loop portion. In some embodiments, an adapter is a hairpin adapter (also referred to herein as a "hairpin"). In some embodiments, a hairpin adapter includes a single nucleic acid strand including a stem-loop structure. In some embodiments, a hairpin adapter includes a nucleic acid having a 5'-end, a 5'-portion, a loop, a 3'-portion and a 3'-end (e.g., arranged in a 5' to 3' orientation). In some embodiments, the 5' portion of a hairpin adapter is annealed and/or hybridized to the 3' portion of the hairpin adapter, thereby forming a stem portion of the hairpin adapter. In some embodiments, the 5' portion of a hairpin adapter is substantially complementary to the 3' portion of the hairpin adapter. In certain embodiments, a hairpin adapter includes a stem portion (i.e., stem) and a loop, wherein the stem portion is substantially double stranded thereby forming a duplex. In some embodiments, the loop of a hairpin adapter includes a nucleic acid strand that is not complementary (e.g., not substantially complementary) to itself or to any other portion of the hairpin adapter. In some embodiments, a method herein includes ligating a first adapter to a first end of a double stranded nucleic acid, and ligating a second adapter to a second end of a double stranded nucleic acid. In some embodiments, the first adapter and the second adapter are different. For example, in certain embodiments, the first adapter and the second adapter may include different nucleic acid sequences or different structures. In some embodiments, the first adapter is a Y-adapter and the second adapter is a hairpin adapter. In some embodiments, the first adapter is a hairpin adapter and a second adapter is a hairpin adapter. In certain embodiments, the first adapter and the second adapter may include different primer binding sites, different structures, and/or different capture sequences (e.g., a sequence complementary to a capture nucleic acid). In some embodiments, some, all or substantially all of the nucleic acid sequence of a first adapter and a second adapter are the same. In some embodiments, some, all or substantially all of the nucleic acid sequence of a first adapter and second adapter are substantially different.

As used herein, the term "loop" is used in accordance with its plain ordinary meaning and refers to the single-stranded region of a hairpin adapter that are located between the duplexed "stem" region of the hairpin adapter. In embodiments, the hairpin loop region is between about 4 nucleotides to 150 nucleotides in length. In embodiments, the hairpin loop is at least 4, 5, 6, 7, 8, 9, 10, 15, 20, 25, 30, 35, 40, 45, 50, or more nucleotides in length. In embodiments, the hairpin loop includes 1, 2, 3, 4, 5, 6, 7, 8, 9, 10, or more T nucleotides. In embodiments, the hairpin loop may include one or more of a primer binding sequence, a barcode, a UMI sequence, or a cleavable site. In some embodiments, a hairpin adapter includes a nucleic acid having a 5'-end, a 5'-portion, a loop, a 3'-portion and a 3'-end (e.g., arranged in a 5' to 3' orientation). In some embodiments, the 5' portion of a hairpin adapter is annealed and/or hybridized to the 3' portion of the hairpin adapter, thereby forming a stem portion of the hairpin adapter. In some embodiments, the 5' portion of a hairpin adapter is substantially complementary to the 3' portion of the hairpin adapter. In certain embodiments, a hairpin adapter includes a stem portion (i.e., stem) and a loop, wherein the stem portion is substantially double stranded thereby forming a duplex. In some embodiments, the loop of a hairpin adapter includes a nucleic acid strand that is not complementary (e.g., not substantially complementary) to itself or to any other portion of the hairpin adapter.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

As used herein the term "determine" can be used to refer to the act of ascertaining, establishing or estimating. A determination can be probabilistic. For example, a determination can have an apparent likelihood of at least 50%, 75%, 90%, 95%, 98%, 99%, 99.9% or higher. In some cases, a determination can have an apparent likelihood of 100%. An exemplary determination is a maximum likelihood analysis or report. As used herein, the term "identify," when used in reference to a thing, can be used to refer to recognition of the thing, distinction of the thing from at least one other thing or categorization of the thing with at least one other thing. The recognition, distinction or categorization can be probabilistic. For example, a thing can be identified with an apparent likelihood of at least 50%, 75%, 90%, 95%, 98%, 99%, 99.9% or higher. A thing can be identified based on a result of a maximum likelihood analysis. In some cases, a thing can be identified with an apparent likelihood of 100%.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |

-continued

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

AS used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or streptavidin to form a avidin-biotin complex or streptavidin-biotin complex.

The term "covalent linker" is used in accordance with its ordinary meaning and refers to a divalent moiety which connects at least two moieties to form a molecule.

The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

As used herein, the term "control" or "control experiment" is used in accordance with its plain and ordinary meaning and refers to an experiment in which the subjects, cells, tissues, or reagents of the experiment are treated as in a parallel experiment except for omission of a procedure, reagent, or variable of the experiment. In some instances, the control is used as a standard of comparison in evaluating experimental effects. In embodiments, a control cell is the same cell type as the cell being examined, wherein the control cell does not include the variable or is subjected to conditions being examined.

Typically, the concentration and molecular weight of the hydrogel subunit(s) will depend on the selected polymer and the desired characteristics, e.g., pore size, swelling properties, conductivity, elasticity/stiffness (Young's modulus), biodegradability index, etc., of the hydrogel network into which they will be polymerized. For example, it may be desirable for the hydrogel to comprise pores of sufficient size to allow the passage of macromolecules, e.g., proteins, nucleic acids, or small molecules as described in greater detail below, into the specimen. The ordinarily skilled artisan will be aware that pore size generally decreases with increasing concentration of hydrogel subunits and generally increases with an increasing ratio of hydrogel subunits to crosslinker, and will prepare a hydrogel composition that comprises a concentration of hydrogel subunits that allows the passage of such macromolecules. As another example, it may be desirable for the hydrogel to have a particular stiffness, e.g., to provide stability in handling the embedded specimen, e.g., a Young's Modulus of about 2-70 $kN/m^2$, for example, about 2 $kN/m^2$, about 4 $kN/m^2$, about 7 $kN/m^2$, about 10 $kN/m^2$, about 15 $kN/m^2$, about 20 $kN/m^2$, about 40 $kN/m^2$, but typically not more than about 70 $kN/m^2$. The ordinarily skilled artisan will be aware that the elasticity of a hydrogel network may be influenced by a variety of factors, including the branching of the polymer, the concentration of hydrogel subunits, and the degree of cross-linking, and will prepare a hydrogel composition that comprises a concentration of hydrogel subunits to provide such desired elasticity. Thus, for example, the hydrogel composition may comprise an acrylamide monomer at a concentration of from about 1% w/v to about 20% w/v, e.g., about 2% to about 15%, about 3% to about 10%, about 4% to about 8%, and a concentration of bis-acrylamide crosslinker in the range of about 0.01% to about 0.075%, e.g., 0.01%, 0.02%, 0.025%, 0.03%, 0.04%, 0.05%, 0.06%, or 0.075%; or, for example, the hydrogel composition may comprise PEG prepolymers having a molecular weight ranging from at least about 2.5K to about 50K, e.g., 2.5K or more, 3.5K or more, 5K or more, 7.5K or more, 10K or more, 15K or more, 20K or more, but typically not more than about 50K, at a concentration in a range from about 1% w/w to about 50% w/w, e.g., 1% or more, 5% or more, 7.5% or more, 10% or more, 15% or more, 20% or more, 30% or more, 40% or more, and usually not more than about 50%. Concentrations of hydrogel subunits that provide desired hydrogel characteristics may be readily determined by methods in the art or as described in the working examples herein.

As used herein, the term "feature" refers a site (i.e., a physical location) on a solid support for one or more molecule(s). A feature can contain only a single molecule or it can contain a population of several molecules of the same species (i.e., a cluster). Features of an array are typically discrete. The discrete features can be contiguous, or they can have spaces between each other. An "optically resolvable feature" refers to a feature capable of being distinguished from other features. Optics and sensor resolution has a finite limit as to a resolvable area. The Rayleigh criterion for the diffraction limit to resolution states that two images are just resolvable when the center of the diffraction pattern of one object is directly over the first minimum of the diffraction pattern of the other object. The minimal distance between two resolvable objects, r, is proportional to the wavelength of light and inversely proportional to the numerical aperture (NA). That is, the minimal distance between two resolvable objects is provided as r=0.61 wavelength/NA. If detecting light in the UV-vis spectrum (about 100 nm to about 900 nm), the remaining mutable variable to increase the resolution is the NA of the objective lens. A lens with a large NA will be able to resolve finer details. For example, a lens with larger NA is capable of detecting more light and so it produces a brighter image. Thus, a large NA lens provides more information to form a clear image, and so its resolving power will be higher. Typical dry objectives have an NA of about 0.80 to about 0.95. Higher NAs may be obtained by increasing the imaging medium refractive index between the object and the objective front lens for example immersing the lens in water (refractive index=1.33), glycerin (refractive index=1.47), or immersion oil (refractive index=1.51). Most oil immersion objectives have a maximum numerical aperture of 1.4, with the typical objectives having an NA ranging from 1.0 to 1.35.

As used herein, the term "upstream" refers to a region in the nucleic acid sequence that is towards the 5' end of a particular reference point, and the term "downstream" refers to a region in the nucleic acid sequence that is toward the 3' end of the reference point.

As used herein, the terms "incubate," and "incubation" refer collectively to altering the temperature of an object in a controlled manner such that conditions are sufficient for conducting the desired reaction. Thus, it is envisioned that the terms encompass heating a receptacle (e.g., a microplate) to a desired temperature and maintaining such temperature for a fixed time interval. Also included in the terms is the act of subjecting a receptacle to one or more heating and cooling cycles (i.e., "temperature cycling" or "thermal cycling"). While temperature cycling typically occurs at relatively high rates of change in temperature, the term is not limited thereto, and may encompass any rate of change in temperature.

"Synthetic" agents refer to non-naturally occurring agents, such as enzymes or nucleotides. The term "synthetic target" as used herein refers to a modified protein or nucleic acid such as those constructed by synthetic methods. In embodiments, a synthetic target is artificial or engineered, or derived from or contains an artificial or engineered protein or nucleic acid (e.g., non-natural or not wild type). For example, a polynucleotide that is inserted or removed such that it is not associated with nucleotide sequences that normally flank the polynucleotide as it is found in nature is a synthetic target polynucleotide.

The term "reaction vessel" is used in accordance with its ordinary meaning in chemistry or chemical engineering, and refers to a container having an inner volume in which a reaction takes place. In embodiments, the reaction vessel may be designed to provide suitable reaction conditions such as reaction volume, reaction temperature or pressure, and stirring or agitation, which may be adjusted to ensure that the reaction proceeds with a desired, sufficient or highest efficiency for producing a product from the chemical reaction. In embodiments, the reaction vessel is a container for liquid, gas or solid. In embodiments, the reaction vessel may include an inlet, an outlet, a reservoir and the like. In embodiments, the reaction vessel is connected to a pump (e.g., vacuum pump), a controller (e.g., CPU), or a monitoring device (e.g., UV detector or spectrophotometer). In embodiments, the reaction vessel is a flow cell. In embodiments, the reaction vessel is within a sequencing device.

It will be understood that the steps of the methods set forth herein can be carried out in a manner to expose an entire site or a plurality of sites of an array with the treatment. For example, a step that involves extension of a primer can be carried out by delivering primer extension reagents to an array such that multiple nucleic acids (e.g. different nucleic acids in a mixture) at each of one or more sites of the solid support are contacted with the primer extension reagents. Similarly, a step of deblocking a blocked primer extension product can be carried out by exposing an array with a deblocking treatment such that multiple nucleic acids (e.g. different nucleic acids in a mixture) at each of one or more sites of the array are contacted with the treatment.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Compositions & Kits

In an aspect, provided herein are compositions useful in nucleic acid amplification and detection (e.g., sequencing). In embodiments, the composition includes alternating layers of oligonucleotide polymeric gels separated by non-oligonucleotide polymeric gels, wherein the oligonucleotide polymeric gel layers include oligonucleotide moieties attached to the oligonucleotide polymeric gel. For example, described herein are three-dimensional (3D) structures in which one or more amplification and/or sequencing reactions may occur, wherein detection of the amplification or sequenced products occurs by imaging through multiple two-dimensional planes. In embodiments, the three-dimensional structures include layers of a polymeric gel forming a 3D scaffold, and are suitable for generating of DNA clusters in discrete layers within the scaffold. In embodiments, the polymeric gel is a porous polymer matrix. In embodiments, the polymeric gel is a hydrogel. In embodiments, the polymeric gel is a polymer network. In embodiments, the composition does not cause excessive light scattering and allows for high-resolution imaging. The composition may have an index of refraction close to water (e.g., the composition has a refractive index at or about 1.3). In embodiments, the composition is optically transparent. In embodiments, the composition permits efficient movement of small molecules, including nucleotides, while also allowing for large molecules (enzymes, DNA templates) to traverse. The optical system used to image the 3D volume may be capable of optically resolving or "sectioning" the volume, and imaging through multiple layers in the volume without unwanted interference from other layers. In embodiments, the composition is formed by alternating layers of polymeric gels, wherein alternating layers include oligonucleotide moieties attached to the polymeric gel.

In an aspect is provided a composition including: (i) a first layer including a polymeric gel including a plurality of oligonucleotides attached to the polymeric gel; (ii) a second layer including a polymeric gel, wherein the polymeric gel does not include a plurality of oligonucleotides attached to the polymeric gel; and (iii) a third layer including a polymeric gel including a plurality of oligonucleotides attached to the polymeric gel. In embodiments, the each oligonucleotide moieties are covalently attached to the polymeric gel.

In an aspect is provided a composition including: (i) a first layer including a polymeric gel including a plurality of particles, each particle including a plurality of oligonucleotide moieties covalently attached to the particle via a polymeric bioconjugate linker; (ii) a second layer including a polymeric gel including a plurality of particles, wherein each particle does not include a plurality of oligonucleotide moieties; and (iii) a third layer including a polymeric gel including a plurality of particles, each particle including a plurality of oligonucleotide moieties covalently attached to the particle via a polymeric bioconjugate linker. In embodiments, each particle is permeable to a sequencing reaction mixture.

In an aspect is provided a composition including: (i) a first layer including a polymeric gel including a plurality of oligonucleotides covalently attached to the polymeric gel; (ii) a second layer including a polymeric gel, wherein the polymeric gel does not include a plurality of oligonucleotides covalently attached to the polymeric gel; and (iii) a third layer including a polymeric gel including a plurality of oligonucleotides covalently attached to the polymeric gel.

In an aspect is provided a composition including (i) a first layer including a polymeric gel; (ii) a second layer including a polymeric gel including a plurality of oligonucleotides covalently attached to the polymeric gel; and (iii) a third layer including a polymeric gel, wherein the first layer and the third layer do not include a plurality of oligonucleotides covalently attached to each of the polymeric gel of the first layer and the polymeric gel of the third layer.

In an aspect is provided a solid support including a multi-layer polymer, wherein the multi-layer polymer includes: a first layer attached to the solid support, wherein the first polymer layer includes a first oligonucleotide within a first polymer layer, and a second layer attached to the first polymer layer, wherein the second polymer layer does not include an oligonucleotide capable of hybridizing a target polynucleotide (e.g., an oligonucleotide including an amplification primer binding sequence) within the second polymer layer. In embodiments, the first oligonucleotide includes a first amplification primer binding sequence and a first sequencing primer binding sequence. In embodiments, the solid support further includes a third layer attached to the second layer, wherein the third layer includes a second oligonucleotide. In embodiments, the second oligonucleotide includes a second amplification primer binding sequence and a second sequencing primer binding sequence. In embodiments the first amplification primer binding sequence is the same as the second amplification primer binding sequence. In embodiments the first amplification primer binding sequence is different as the second amplification primer binding sequence.

In another aspect is provided a solid support including a multi-layer polymer, wherein the multi-layer polymer includes: a first layer (e.g., a polymeric gel) attached to the solid support, wherein the first layer includes a plurality of particles, each particle including a first oligonucleotide moiety covalently attached to the particle via a polymeric bioconjugate linker, and a second layer attached to the first polymer layer, wherein the second layer includes a plurality of particles, each particle does not include an oligonucleotide moiety, wherein the first oligonucleotide includes a first amplification primer binding sequence and a first sequencing primer binding sequence.

In embodiments, the solid support further includes a third layer attached to the second layer, wherein the third layer includes a plurality of particles, each particle including a second oligonucleotide. In embodiments, the second oligonucleotide includes a second amplification primer binding sequence and a second sequencing primer binding sequence. In embodiments the first amplification primer binding sequence is the same as the second amplification primer binding sequence. In embodiments the first amplification primer binding sequence is different as the second amplification primer binding sequence.

In embodiments, solid support and/or the composition includes a third layer, wherein the first layer is immediately adjacent to the second layer, wherein the third layer is immediately adjacent to the second layer, and wherein the first layer and third layer are not immediately adjacent.

In embodiments, the polymeric gel is permeable to an amplification and/or sequencing reaction mixture (e.g., one or more aqueous mixtures that contains the reagents necessary to allow addition of an optionally detectable nucleotide to a polynucleotide strand by a polymerase). In embodiments, the polymeric gel is permeable to large molecules such as enzymes and DNA moieties.

In an aspect is provided a composition including: (i) a first layer including a plurality of particles, each particle including a plurality of oligonucleotide moieties covalently attached to the particle via a polymeric bioconjugate linker; (ii) a second layer including a plurality of particles, wherein each particle does not include a plurality of oligonucleotide moieties; and (iii) a third layer including a plurality of particles, each particle including a plurality of oligonucleotide moieties covalently attached to the particle via a polymeric bioconjugate linker. In embodiments, each particle is permeable to a sequencing reaction mixture.

In embodiments, the first layer is immediately adjacent to the second layer, wherein the third layer is immediately adjacent to the second layer, and wherein the first layer and third layer are not immediately adjacent. In embodiments, the first layer is in contact with the second layer. In embodiments, the second layer is in contact with the third layer. In embodiments, the first layer, second layer, and third layer are in contact.

In embodiments, the first layer, second layer, and third layer are in fluidic contact. In embodiments, the first layer and second layer are in fluidic contact. In embodiments, the second layer and third layer are in fluidic contact. In embodiments, the first layer and third layer are in fluidic contact.

In embodiments, the first, second, and third layers form a contiguous layered unit. In embodiments, each contiguous layered unit includes a first layer and a third layer each including a polymeric gel including a plurality of oligonucleotides covalently attached to the polymeric gel, and a second layer including a polymeric gel, wherein the polymeric gel does not include a plurality of oligonucleotides covalently attached to the polymeric gel. In embodiments, each contiguous layered unit includes a first layer and a third layer each including a polymeric gel including a plurality of particles, each particle including a plurality of oligonucleotide moieties covalently attached to the particle via a polymeric bioconjugate linker; and a second layer including a polymeric gel including a plurality of particles, wherein each particle does not include a plurality of oligonucleotide moieties. In embodiments, each contiguous layered unit includes a first layer and a second layer each including a plurality of particles, each particle including a plurality of oligonucleotide moieties covalently attached to the particle via a polymeric bioconjugate linker; and a second layer including a plurality of particles, wherein each particle does not include a plurality of oligonucleotide moieties. In some embodiments, the second layer is immediately adjacent and in fluidic contact with the first layer, and the third layer is immediately adjacent and in fluidic contact with the second layer.

Figure 3:
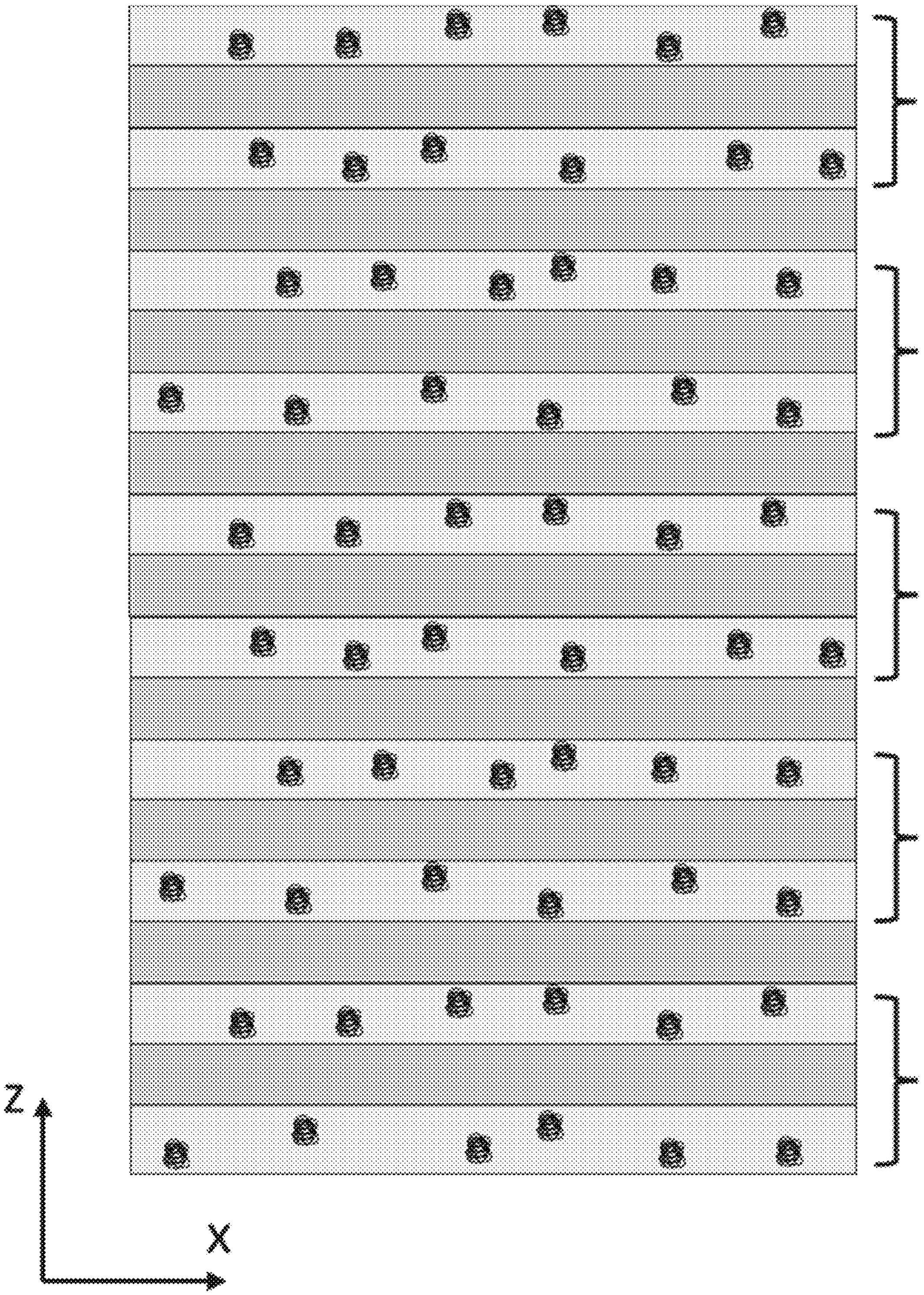
FIG. 3 illustrates an exemplary multi-layered, spatially heterogeneous polymer scaffold. In this example, the polymer scaffold includes 10 active polymer layers, each separated by at least one inactive polymer layer. The bottommost active polymer layer may, for example, contact the surface of the solid support. The uppermost active polymer layer may, for example, be exposed to the environment, or contact a cover. As described herein, each set of two active layers separated by an inactive polymer layer may be referred to as a contiguous layered unit, as denoted by the brackets on the right-hand side of the scaffold. In this illustration, the multi-layered, spatially heterogeneous polymer scaffold has five contiguous layered units, each separated by at least one inactive polymer layer.

In embodiments, the composition further includes two or more contiguous layered units (e.g., the composition illustrated in FIG. 3 includes five contiguous layered units, as indicated by each of the brackets). In embodiments, each of the two or more contiguous layered units is separated by a layer including a polymeric gel, wherein the polymeric gel does not include a plurality of oligonucleotides covalently attached to the polymeric gel (see, e.g., FIG. 3). In embodiments, each of the two or more contiguous layered units is separated by a layer including a polymeric gel including a plurality of particles, wherein each particle does not include a plurality of oligonucleotide moieties. In embodiments, each of the two or more contiguous layered units is separated by a layer including a plurality of particles, wherein each particle does not include a plurality of oligonucleotide moieties.

In embodiments, each layer is substantially planar. A "substantially planar" shape may be substantially flat and uninterrupted, or may have openings, divots, or other interruptions therein, and/or may be curved or bent.

In embodiments, the composition is contained in a substrate. In embodiments, the composition is attached to a solid support. In embodiments, the solid support is a slide, for example, a glass slide. In embodiments, the solid support includes one, two, three, or more contiguous layered units as described herein.

In embodiments, each layer has a width of about 1-20 mm, a length of about 1-20 cm, and a depth of about 0.5-15 μm. In embodiments, each layer has a width of about 1-20 mm. In embodiments, each layer has a width of about 1, about 2, about 3, about 4, about 5, about 6, about 7, about 8, about 9, about 10, about 11, about 12, about 13, about 14, about 15, about 16, about 17, about 18, about 19, or about 20 mm. In embodiments, each layer has a length of about 1-20 cm. In embodiments, each layer has a length of about 1, about 2, about 3, about 4, about 5, about 6, about 7, about 8, about 9, about 10, about 11, about 12, about 13, about 14, about 15, about 16, about 17, about 18, about 19, or about 20 cm. In embodiments, each layer has a depth of about 0.5-15 μm. In embodiments, each layer has a depth of about 0.5, about 1, about 2, about 3, about 4, about 5, about 6, about 7, about 8, about 9, about 10, about 11, about 12, about 13, about 14, or about 15 μm.

In embodiments, the first layer, the third layer, or both the first layer and the third layer are attached to a solid support. In embodiments, the first layer is attached to a solid support. In embodiments, the third layer is attached to a solid support. In embodiments, both the first layer and the third layer are attached to a solid support.

In embodiments, at least one contiguous layered unit is attached to a solid support. In embodiments, at least two contiguous layered units are attached to a solid support. In embodiments, one contiguous layered unit is attached to a solid support. In embodiments, two contiguous layered units are attached to a solid support. In embodiments, every contiguous layered unit is attached to a solid support. In embodiments, a plurality of contiguous layered units are attached to a solid support. In embodiments, the contiguous layered unit is prepared by spin-coating each layer composition onto a solid support in an alternating fashion until the target number of layers have been deposited (e.g., until three layers have been deposited onto the solid support). For example, the first layer, second layer, and third layer are spin-coated sequentially onto a solid support, thereby forming a contiguous layered unit attached to the solid support. Additional spin-coating of layer compositions may be performed to add additional contiguous layered units (e.g., an additional three layers are spin coated onto the uppermost contiguous layered unit, thereby adding an additional contiguous layered unit onto the solid support). In embodiments, the at least one contiguous layered unit is attached to the solid support via non-covalent binding. For example, the contiguous layered unit is attached to the solid support due to surface interactions, such as Van der Waal forces, electrostatic forces, hydrophobic interactions and hydrogen bonds. The physical adsorption efficiency can be enhanced by treating the solid support with air plasma to increase its hydrophilicity. In embodiments, the solid support includes a functionalized glass surface or a functionalized plastic surface. In embodiments, the functionalized glass surface includes (3-aminopropyl)triethoxysilane (APTES), (3-Aminopropyl)trimethoxysilane (APTMS), γ-Aminopropylsilatrane (APS), N-(6-aminohexyl)aminomethyltriethoxysilane (AHAMTES), polyethylenimine (PEI), 5,6-epoxyhexyltriethoxysilane, or triethoxysilylbutyraldehyde, or a combination thereof. In embodiments, the contiguous layered unit is retained on the solid support due to interactions with the functionalized surface of the support (e.g., due to the positive charge of the amines covalently bound to an APTES-functionalized surface which facilitate strong attachment forces and prevent contiguous layered unit detachment). In embodiments, the solid support includes a polymer coating onto which the contiguous layered unit is covalently attached to (e.g., through the association of molecules of bioconjugate reactive groups).

In embodiments, the oligonucleotide (alternatively referred to herein as primer or polynucleotide primer) is covalently attached to the polymer. In embodiments, the 5' end of the oligonucleotide moiety contains a functional group that is tethered to the polymer (i.e., the particle shell polymer or the polymeric particle). Non-limiting examples of covalent attachment include amine-modified oligonucleotide moieties reacting with epoxy or isothiocyanate groups on the polymer, succinylated oligonucleotide moieties reacting with aminophenyl or aminopropyl functional groups on the polymer, dibenzocycloctyne-modified oligonucleotide moieties reacting with azide functional groups on the particle polymer (or vice versa), trans-cyclooctyne-modified oligonucleotide moieties reacting with tetrazine or methyl tetrazine groups on the polymer (or vice versa), disulfide modified oligonucleotide moieties reacting with mercapto-functional groups on the polymer, amine-functionalized oligonucleotide moieties reacting with carboxylic acid groups on the polymer via 1-ethyl-3-(3-dimethylaminopropyl)-carbodiimide hydrochloride (EDC) chemistry, thiol-modified oligonucleotide moieties attaching to a polymer via a disulfide bond or maleimide linkage, alkyne-modified oligonucleotide moieties attaching to a polymer via copper-catalyzed click reactions to azide functional groups on the polymer, and acrydite-modified oligonucleotide moieties polymerizing with free acrylic acid monomers on the polymer to form polyacrylamide or reacting with thiol groups on the polymer. In embodiments, the oligonucleotide moiety is attached to the polymer through electrostatic binding. For example, the negatively charged phosphate backbone of the primer may be bound electrostatically to positively charged monomers in the polymer.

In embodiments, the plurality of particles are uniformly arranged. In embodiments, each of the first and third layer of the composition include a single layer of particles. In embodiments, each of the first and third layer of the composition include one or more layers of particles. In embodiments, each layer of the composition includes a single layer of particles. In embodiments, each layer of the composition includes one or more layers of particles. In embodiments, arranging particles in a each layer of the composition includes distributing particles throughout the layer (e.g., a polymeric gel layer of the composition) such that substantially all particles (e.g., at least 90%, 95%, 99%, or 100%) are in contact with the layer. The maximum number of particles capable of forming a uniform layer, or non-uniform layer, will depend on the size of the particles and the dimensions of the polymeric gel to which they are applied, as can be calculated by one skilled in the art. The plurality of particles in the polymeric gel layer may be arranged uniformly (e.g., particles packed closely together with substantially no gaps, or having gaps of uniform size and in uniform intervals), or arranged non-uniformly (e.g., particles having an unordered arrangement of particles, such that some particles are closer together than others). In general, an arrangement lacking a substantially regular spacing between particles is considered non-uniform. For example, MOF particles may be collected in a volume at a concentration that allows for irregular gaps (e.g., bubble-like spaces of a suspending fluid) surrounded by particles. For example, to produce a non-uniform arrangement of particles, particles may be applied to the polymeric gel layer at a concentration such that particles only occupy about 80% of the surface area, and are allowed to come to rest at random positions. In embodiments, a polymeric gel layer including a plurality of particles is stabilized by cross-linking particles to a polymer and/or to one another. In embodiments, the plurality of particles are not uniformly arranged.

In embodiments, the first polymer layer, the third polymer layer, or both the first polymer layer and the third polymer layer are attached to a solid support (e.g., attached to the top and the bottom of a flow cell). In embodiments, the first layer is immediately adjacent to the second layer, wherein the third layer is immediately adjacent to the second layer, and wherein the first layer and third layer are not immediately adjacent. In embodiments, the first layer is in contact with the second layer. In embodiments, the second layer is in contact with the third layer. In embodiments, the first layer, second layer, and third layer are in contact. In embodiments, the first layer, second layer, and third layer are in fluidic contact. In embodiments, the first layer and second layer are in fluidic contact. In embodiments, the second layer and third layer are in fluidic contact. In embodiments, the first layer and third layer are in fluidic contact.

In embodiments, each polymer layer includes the same polymer composition. In embodiments, each polymer layer includes a different polymer composition. In embodiments, each polymer layer includes polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl) cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly (vinylsulfonic acid) (PVSA), poly(L-aspartic acid), poly(L-glutamic acid), polylysine, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, each polymer layer is a hydrogel.

In embodiments, the polymer layer includes polymerized units of polyethylene glycol methacrylate (PEGMA) and glicydyl methacrylate (GMA). In embodiments, the polymer layer includes polymerized units of polyethylene glycol methacrylate (PEGMA) and isocyanatoethyl methacrylate (IEM). In embodiments, the polymer layer includes polymerized units of glicydyl methacrylate azide (GMA azide) and polyethylene glycol methacrylate (PEGMA). In embodiments, the ratio of GMA azide to PEGMA is 1:1. In embodiments, the ratio of GMA azide to PEGMA is 1:2. In embodiments, the ratio of GMA azide to PEGMA is 1:3. In embodiments, the ratio of GMA azide to PEGMA is 1:4. In embodiments, the ratio of GMA azide to PEGMA is 1:5. In embodiments, the ratio of GMA azide to PEGMA is 1:6. In embodiments, the ratio of GMA azide to PEGMA is 1:7. In embodiments, the ratio of GMA azide to PEGMA is 1:8. In embodiments, the polymer layer includes polymerized units of 3-azido-2-hydroxypropyl methacrylate, 2-azido-3-hydroxypropyl methacrylate, 2-(((2-azidoethoxy)carbonyl)amino)ethyl methacrylate, 3-azido-2-hydroxypropyl acrylate, 2-azido-3-hydroxypropyl acrylate, or 2-(((2-azidoethoxy)carbonyl)amino)ethyl acrylate. In embodiments, the polymer layer includes polymerized units of 3-azido-2-hydroxypropyl methacrylate, 2-azido-3-hydroxypropyl methacrylate, or 2-(((2-azidoethoxy)carbonyl)amino)ethyl methacrylate. In embodiments, the polymer layer includes polymerized units of 3-azido-2-hydroxypropyl methacrylate. In embodiments, the polymer layer includes polymerized units of 3-azido-2-hydroxypropyl methacrylate 2-azido-3-hydroxypropyl methacrylate. In embodiments, the polymer layer includes polymerized units of 3-azido-2-hydroxypropyl methacrylate 2-(((2-azidoethoxy)carbonyl)amino)ethyl methacrylate. In embodiments, the polymer layer includes polymerized units of a) polyethylene glycol methacrylate (PEGMA) and glicydyl methacrylate (GMA), b) polyethylene glycol methacrylate (PEGMA) and isocyanatoethyl methacrylate (IEM), or c) polyethylene glycol methacrylate (PEGMA) and glicydyl methacrylate (GMA) azide, wherein the particle core is a silica particle. In embodiments, the particle includes a plurality of polymer layers (e.g., a plurality of polyethylene glycol methacrylate (PEGMA) and glicydyl methacrylate (GMA) azide copolymers).

The polymer layer may be polymerized from a mixture of functionalized and non-functionalized monomers, such that at least some functionalized monomers that provide attachment points (e.g., azide moieties) for primers (e.g., DBCO-containing oligonucleotide primers) are spaced from one another by one or more monomers lacking such attachment points (e.g., PEG or AAm). The frequency of monomer units attached to primers within a polymer can be adjusted by changing the concentration of the corresponding functionalized monomer in the mixture of monomers. In embodiments, monomer units of the polymer layer that are attached to a polynucleotide primer are separated by, on average, about or at least about 1, 2, 3, 4, 5, 6, 7, 8, 9, 10, 15, 20, 25, 30, 40, 50, or more monomer units that are not attached to a primer, referred to herein as (ng). In embodiments, monomer units of the polymer layer that are attached to a polynucleotide primer (referred to herein as oligonucleotide moieties) are separated by, on average, about or at least about 1, 2, 3, 4, 5, 6, 7, 8, 9, 10, 15, 20, 25, 30, 40, 50, or more monomer units that are not attached to a primer, referred to herein as (ng). In embodiments, monomer units of the polymer layer that are attached to a polynucleotide primer are separated by, on average, about or at least about 4 to 8 monomer units that are not attached to a primer. In embodiments, monomer units of the polymer layer that are attached to a polynucleotide primer are separated by, on average, about 4 to 8 monomer units that are not attached to a primer. In embodiments, monomer units of the polymer layer that are attached to a polynucleotide primer are separated by, on average, about or at least about 6, 7, or 8 monomer units that are not attached to a primer. In embodiments, primer-attached monomers are separated by, on average, about 1-50, 2-40, 3-30, 4-25, or 5-20 monomers not attached to primers. In embodiments, monomer units of the polymer layer that are attached to a polynucleotide primer are separated by 3 monomer units that are not attached to a primer (aka 3 ng). In embodiments, monomer units of the polymer layer that are attached to a polynucleotide primer are separated by 6 ng. In embodiments, monomer units the polymer layer that are attached to a polynucleotide primer are separated by 9 ng. The mixture can include monomers with different functional groups (e.g., azides, alkynes, DBCO, etc.) as described herein.

In embodiments, the polymer layer includes a copolymer of two or more of the following polymerizable monomers, wherein at least one of the polymerizable monomers includes a bioconjugate reactive moiety: polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, N-vinyl pyrrolidone, polyethylene glycol (PEG)-thiol/PEG-acrylate, acrylamide/N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), and/or isocyanatoethyl methacrylate (IEM).

In embodiments, the polymeric gel, plurality of particles, or both include water.

In embodiments, the polymeric gel, plurality of particles, or both have a refractive index of about 1.3 when hydrated. In embodiments, the polymeric gel, plurality of particles, or both have a refractive index of about 1.2-1.6, 1.25-1.5, or 1.3-1.4 when hydrated. In embodiments, the polymeric gel, plurality of particles, or both have a refractive index of 1.2, 1.25, 1.3, 1.35, 1.4, 1.45, 1.5, 1.55, or 1.6 when hydrated.

The manner in which a polynucleotide primer is attached to the polymeric gel will depend on the type of functional group used to form the attachment. A variety of suitable functional groups are available, examples of which are provided herein. In embodiments, functional groups are selected that specifically react with their intended target (e.g., a paired functional group attached to a desired target, such as a primer), while also exhibiting anti-fouling characteristics that prevent, or have a reduced propensity for, non-specific binding of enzymes, dye-labeled nucleotides, and nucleic acids.

Polymeric gels can comprise any of a variety of polymers. In embodiments, the polymeric gel is a hydrogel. In embodiments, hydrogels are super-absorbent (e.g., containing more than about 90% water) and can be comprised of natural or synthetic polymers. Hydrogels can contain over 99% water and may comprise natural or synthetic polymers, or a combination thereof. Hydrogels also possess a degree of flexibility very similar to natural tissue, due to their significant water content. A detailed description of suitable hydrogels may be found in published U.S. patent application 20100055733, herein specifically incorporated by reference. By "hydrogel subunits" or "hydrogel precursors" is meant hydrophilic monomers, prepolymers, or polymers that can be crosslinked, or "polymerized", to form a three-dimensional (3D) hydrogel network. Examples of hydrogels include, but are not limited to agarose- and acrylamide-based gels, such as polyacrylamide, poly-N-isopropylacrylamide, poly N-isopropylpolyacrylamide, 2-hydroxyethyl acrylate and methacrylate, zwitterionic monomers, polyethylene glycol acrylate and methacrylate. In embodiments, the hydrogel includes agarose, alginate, gelatin, cellulose, polyolefin, polyethylene glycol, polyvinyl alcohol, and/or acrylate polymers and copolymers. In embodiments, the hydrogel includes agarose, amylose, or amylopectin. In embodiments, the hydrogel includes acrylamide, methacrylate and methacrylamide polymers and copolymers thereof. In embodiments, an aqueous solution of one or more types of monomers is dispersed in a droplet, and then polymerized, e.g., to form a gel. Another example of a hydrogel includes alginic acid that can be gelled by the addition of calcium ions. As a further example, gelation initiators (e.g., ammonium persulfate and TEMED for acrylamide, or Ca' for alginate) can be added to a droplet, for example, by co-flow with the aqueous phase, by co-flow through the oil phase, or by coalescence of two different drops. In embodiments, the monomers include acrylate and/or methacrylate monomers. In embodiments, monomers include hydrophilic and/or hydrophobic monomers. In embodiments, the shell polymer comprises a polymer of one or more of acrylate, methacrylate, polyolefins, styrene, polycarbonates, polyurethanes, polysiloxanes, polyalkyloxides, polynorbornene, or polysaccharides. In embodiments, the shell polymer comprises a polymer of one or more of GMA (glicydyl methacrylate), HEMA (Hydroxyethylmethacrylate), HEA (Hydroxyethylacrylate), or HPMA (hydroxypropylmethacrylate). In further embodiments, polymeric gel is formed by polymerization of monomers in a solution. The type and concentration of monomers, and the duration of the polymerization reaction may be selected to produce polymeric gels having a desired property.

In embodiments, the hydrogel includes about 80% to about 99% water. In embodiments, the hydrogel includes about 80% to about 95% water. In embodiments, the hydrogel includes about 80% to about 90% water. In embodiments, the hydrogel includes about 80% to about 85% water. In embodiments, the hydrogel includes about 80%, about 85%, about 90%, about 91%, about 92%, about 93%, about 94%, about 95%, about 96%, about 97%, about 98%, or about 99% water. In embodiments, the hydrogel includes about 80% water. In embodiments, the hydrogel includes about 85% water. In embodiments, the hydrogel includes about 90% water. In embodiments, the hydrogel includes about 91% water. In embodiments, the hydrogel includes about 92% water. In embodiments, the hydrogel includes about 93% water. In embodiments, the hydrogel includes about 94% water. In embodiments, the hydrogel includes about 95% water. In embodiments, the hydrogel includes about 96% water. In embodiments, the hydrogel includes about 97% water. In embodiments, the hydrogel includes about 98% water. In embodiments, the hydrogel includes about 99% water.

In embodiments, the polymeric gel includes a thermo-responsive polymer, chemically-responsive polymer, light-responsive polymer, or pH-responsive polymer. In embodiments, the polymeric gel includes a thermo-responsive polymer. In embodiments, the polymeric gel includes a chemically-responsive polymer. In embodiments, the polymeric gel includes a light-responsive polymer. In embodiments, the polymeric gel includes a pH-responsive polymer.

Thermo-responsive polymers undergo reversible volume-phase transitions in response to changes in their surrounding temperatures (see, Lim H L et al. Biomater. Sci. 2014; 2: 603, which is incorporated herein by reference in its entirety). In embodiments, the thermo-responsive polymer includes a homopolymer or copolymer of acrylamide, methacrylamide, N-ethyl acrylamide, N-n-propyl acrylamide, N-n-propyl methacrylamide, N-isopropyl acrylamide, N-isopropyl methacrylamide, N-cyclopropyl acrylamide, N-cyclopropyl methacrylamide, N-ethoxyethyl acrylamide, N-ethoxyethyl methacrylamide, N-tetrahydrofurfuryl acrylamide, N-tetrahydro furfuryl methacrylamide, N,N-dimethyl (meth)acrylamide, N,N-ethylmethyl acrylamide, N,N-diethyl acrylamide, 1-(1-oxo-2-propenyl)-pyrrolidine, 1-(1-oxo-2-propenyl)-piperidine, 4-(1-oxo-2-propenyl)-morpholine, 1-(1-oxo-2-methyl-2-propenyl)-pyrrolidine, 1-(1-oxo-2-methyl-2-propenyl)-piperidine, 4-(1-oxo-2-methyl-2-propenyl)-morpholine, methyl vinyl ether, or a combination thereof. Additional examples of thermo-responsive polymers may be found, for example, in U.S. Pat. Pubs. US2008/0160559 and US2014/0255333, which are incorporated herein by reference in their entirety.

In embodiments, the chemically-responsive polymer is responsive to chemical stimuli, for example, changes in ionic strength, pH, solvent composition, and molecular species in the external solution/environment. In embodiments, the chemically-responsive polymer is a pH-responsive polymer. In embodiments, the pH-responsive polymer includes methyl acrylate, ethyl acrylate, vinyl acrylate, propyl acrylate, butyl acrylate, hexyl acrylate, octyl acrylate, decyl acrylate, dodecyl acrylate, myristyl acrylate, lauryl acrylate, cetyl acrylate, stearyl acrylate, methyl methacrylate, ethyl methacrylate, propyl methacrylate, butyl methacrylate, isobutyl methacrylate, hexyl methacrylate, 2-ethylhexyl-(meth)acrylate, phenyl methacrylate, octyl methacrylate, decyl methacrylate, dodecyl methacrylate, myristyl methacrylate, lauryl methacrylate, cetyl methacrylate, stearyl methacrylate, or a combination thereof. Additional examples of pH-sensitive polymers may be found, for example in U.S. Pat. Pubs. US2005/0154165 and US2005/0137372, which are incorporated herein by reference in their entirety.

In embodiments, the light-responsive polymer includes different modes of actions that can be stimulated by light, such as photoisomerization, photocleavage, photodimerization, photorearrangement, and photoconjugation. For example, an azobenzene group undergoes a reversible cis-trans isomerization upon UV irradiation, while photochromic chromophores like coumarin, anthracene, and cinnamoyl groups undergo reversible dimerization upon UV irradiation. Specifically, polymers containing coumarin, anthracene, and cinnamoyl moieties undergo photodimerization reaction when irradiated with long-wavelength UV light ($\lambda$=300-365 nm), and photoreversible cleavage upon exposure to short-wavelength UV light ($\lambda$=254 nm) (see, Mohamed M A et al. Progress in Polymer Science. 2019; 98:

101147, which is incorporated herein by reference in its entirety). In embodiments, the light-responsive polymer is capable of changing its physical and/or chemical properties such as elasticity, viscosity, shape and swelling degree, for example, upon light irradiation. In various embodiments, the light-responsive polymer includes light reactive groups such as photochromic moieties. In some embodiments, light-sensitive chromophores such as azobenzenes are added into a polymer network, thereby making embodiments of the polymer sensitive to UV light. In some embodiments, photocleavable groups are immobilized into a polymer network, thereby making embodiments of the polymer sensitive to UV light. In other embodiments, chlorophyllin chromophore is introduced into a polymer, e.g. a poly(N-isopropylacrylamide) (PNIPAM) so that it becomes sensitive to visible light. Additional examples of light-responsive polymers may be found in, for example, U.S. Pat. Pub. US2006/0257629 and PCT Pub. WO2016/123480, each of which is incorporated herein by reference in its entirety.

In embodiments, the pH-responsive polymer includes polymers each intramolecularly having an acidic functional group such as a carboxylic acid or a sulfonic acid group, or a basic functional group such as a primary amine, a secondary amine, or a tertiary amine. Specific examples are polymers as polymerized products of monomers such as acrylic acid, methacrylic acid, vinyl acetate, maleic acid, vinylsulfonic acid, styrenesulfonic acid, vinylpyridine, vinylaniline, vinylimidazole, aminoethyl acrylate, methylaminoethyl acrylate, dimethylaminoethyl acrylate, ethylaminoethyl acrylate, ethylmethylaminoethyl acrylate, diethylaminoethyl acrylate, aminoethyl methacrylate, methylaminoethyl methacrylate, dimethylaminoethyl methacrylate, ethylaminoethyl methacrylate, ethylmethylaminoethyl methacrylate, diethylaminoethyl methacrylate, aminopropyl acrylate, methylaminopropyl acrylate, dimethylaminopropyl acrylate, ethylaminopropyl acrylate, ethylmethylaminopropyl acrylate, diethylaminespropyl acrylate, aminopropyl methacrylate, methylaminopropyl methacrylate, dimethylaminopropyl methacrylate, ethylaminopropyl methacrylate, ethylmethylaminopropyl methacrylate, diethylaminopropyl methacrylate, dimethylaminoethylacrylamide, and dimethylaminopropylacrylamide. Additional examples of pH-responsive polymers may be found, for example, in U.S. Pat. Pub. US2007/0196492, which is incorporated herein by reference in its entirety.

In embodiments, each core has a core diameter, the shell polymer surrounding each core has a thickness defining an outer shell diameter, and the core and shell diameters are designed to have particular dimensions. In embodiments, the core diameter may be about 5% to about 95%, about 10% to about 90%, about 20% to about 80%, about 30% to about 70%, or about 40% to about 60% of the outer shell diameter, or a number or a range between any two of these values. In embodiments, the core diameter about or at most about 10%, 20%, 30%, 40%, 50%, 60%, 70%, 80%, 90%, 95%, or 99% of the shell diameter or a number or a range between any two of these values. In embodiments, the core diameter is about 20% to about 80% of the outer shell diameter, or about 50% of the shell diameter.

In embodiments, the core diameter is about 50-2000 nanometers, 500-1500 nanometers, about 1000 nanometers, or a number or a range between any two of these values. In embodiments, the core diameter is at least, about, or at most 100, 200, 300, 400, 500, 600, 700, 800, 900, 1000, 1100, 1200, 1300, 1400, 1500, 1600, 1700, 1800, 1900, 2000 nanometers or a number or a range between any two of these values. In embodiments, the shell diameter is about 0.1-10 microns, 0.25-5 microns, 0.5-2 microns, 1 micron, or a number or a range between any two of these values. In embodiments, the shell diameter is at least, about, or at most 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 μm or a number or a range between any two of these values. In embodiments, the core diameter is about 200-1200 nanometers, and/or the shell diameter is about 0.25-5 μm (microns).

In embodiments, the particle includes a degradable particle core, referred to herein as a core, and polymer shell surrounding the core. The core may be referred to herein as a nanoparticle core wherein the longest diameter is less than 1000 nanometers. Lengths and sizes of particles and their surrounding cores as described herein may be measured using Transmission Electron Microscopy (TEM). In embodiments, the cores and/or polymer shells of the particles are approximately spherical. As used herein the term “spherical” refers to structures which appear substantially or generally of spherical shape to the human eye, and does not require a sphere to a mathematical standard. In other words, “spherical” cores or particles are generally spheroidal in the sense of resembling or approximating to a sphere. In embodiments, the diameter of a spherical core or particle is substantially uniform, e.g., about the same at any point, but may contain imperfections, such as deviations of up to 1, 2, 3, 4, 5 or up to 10%. Because cores or particles may deviate from a perfect sphere, the term “diameter” refers to the longest dimension of a given core or particle. Likewise, polymer shells are not necessarily of perfect uniform thickness all around a given core. Thus, the term “thickness” in relation to a polymer structure (e.g., a shell polymer of a particle) refers to the average thickness of the polymer layer.

In embodiments, the core polynucleotide primer is covalently attached to the core. In embodiments, the 5' end of the polynucleotide contains a functional group that is tethered to the core. Non-limiting examples of covalent attachment include amine-modified polynucleotides reacting with epoxy or isothiocyanate groups on the core, succinylated polynucleotides reacting with aminophenyl or aminopropyl functional groups on the core, dibenzocycloctyne-modified polynucleotides reacting with azide functional groups on the core (or vice versa), trans-cyclooctyne-modified polynucleotides reacting with tetrazine or methyl tetrazine groups on the core (or vice versa), disulfide modified polynucleotides reacting with mercapto-functional groups on the core, amine-functionalized polynucleotides reacting with carboxylic acid groups on the core via 1-ethyl-3-(3-dimethylaminopropyl)-carbodiimide hydrochloride (EDC) chemistry, thiol-modified polynucleotides attaching to a core via a disulphide bond or maleimide linkage, alkyne-modified polynucleotides attaching to a core via copper-catalyzed click reactions to azide functional groups on the core, and acrydite-modified polynucleotides polymerizing with free acrylic acid monomers on the core to form polyacrylamide or reacting with thiol groups on the core. In embodiments, the core polynucleotide primer is attached to the core through electrostatic binding. For example, the negatively charged phosphate backbone of the primer may be bound electrostatically to positively charged monomers in the core.

In embodiments, each core includes multiple copies of one or more core polynucleotide primer(s). In embodiments, the one or more core polynucleotide primers include at least two different primers attached to the core (e.g., a forward and a reverse primer), each of which may be present in multiple copies.

In embodiments, the core and shell polymer are permeable to a polymerase for amplifying the target polynucleotide. In embodiments, the shell polymer has a higher permeability than the core. In embodiments, the core and shell polymer have the same permeability. In embodiments, the shell polymer is permeable to a polymerase for amplifying the target polynucleotide, such that the interface of the core is in contact with the polymerase. In embodiments, the core and shell polymer are permeable to a sequencing reaction mixture. The term "sequencing reaction mixture" refers to an aqueous mixture that contains the reagents necessary to allow addition of a nucleotide to a polynucleotide strand by a polymerase (e.g., addition of a dNTP or dNTP analogue to a DNA strand by a DNA polymerase). Exemplary mixtures include buffers (e.g., saline-sodium citrate (SSC), tris(hydroxymethyl)aminomethane or "Tris"), salts (e.g., KCl or $(NH_4)_2SO_4$)), nucleotides, polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), detergents and/or crowding agents (e.g., PEG, Tween, BSA). In embodiments, the shell polymer is permeable to a sequencing reaction mixture for amplifying the target polynucleotide, such that the interface of the core is in contact with the sequencing reaction mixture.

In embodiments, each core contains one or more reagents for amplifying the target polynucleotide (e.g., a sequencing reaction mixture). Examples of reagents include but are not limited to polymerase, buffer, and nucleotides. In embodiments, the nucleotides are reversibly terminated nucleotides carrying fluorescent dyes, such that the identity of a nucleotide added in a sequencing reaction can be identified based on the fluorescent dye with which it is associated.

In embodiments, each core further includes a detectable label that indicates the identity of a nucleotide in the target polynucleotide. In embodiments, the detectable label is a fluorescent label.

In embodiments, each core further includes a silica, magnetic, or paramagnetic material, such as in the form of a bead. For example, the core/shell layers may be formed around a supporting bead, for example, a silica, magnetic, or paramagnetic bead. In some embodiments, the composition includes a solid bead support (which itself may include a magnetic core and an encapsulating polymer layer), a functional core layer around the bead for primer attachment, and a shell polymer layer in which no amplification reactions take place.

In embodiments, the particle includes a degradable particle core, referred to herein as a core, and polymer shell surrounding the core.

In embodiments, the particle is a functionalized particle including a degradable particle core (e.g., a MOF particle core) and a polymer shell, wherein the polymer shell is covalently attached to the particle core and includes a plurality of polymerized units of shell monomers and one or more shell monomers includes an oligonucleotide moiety covalently linked to the shell monomer. In embodiments, the particle is a functionalized particle including a degradable particle core and a polymer shell surrounding the particle core wherein the polymer shell includes a plurality of polymerized units of shell monomers and one or more of the shell monomers includes an oligonucleotide moiety covalently linked to the shell monomer via a bioconjugate linker. The polymer shell includes a polymerized units of shell monomers (e.g., PEGMA) linked with bioconjugate reactive moieties (e.g., GMA-Az). In embodiments, the polymerized shell comprises linear polymerized units of shell monomers linked with bioconjugate reactive moieties. In embodiments, the linear polymerized units of shell monomers may be crosslinked. In embodiments, the polymerized units of shell monomer is covalently bound to the degradable particle core. For example, the polymerized units of shell monomers is attached to the particle via a polymerization initiator, for example (3-trimethoxysilyl)propyl 2-bromo-2-methylpropionate, wherein the —Si—O— moieties are attached to a silica particle. In embodiments, the polymerization initiator has the formula:

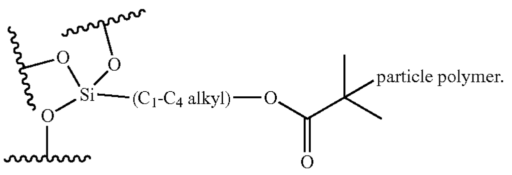

In an aspect is a particle including a degradable particle core; a polymer shell surrounding the degradable particle core; and a plurality of oligonucleotide moieties covalently attached to the particle via a polymeric bioconjugate linker. In embodiments, the polymer shell includes a plurality of polymerized units of shell monomers and a plurality of oligonucleotide moieties wherein each oligonucleotide moiety is covalently attached to the polymer shell via a bioconjugate linker. In embodiments, the polymeric bioconjugate linker is the product of a reaction between the two bioconjugate group (e.g., click chemistry group). In embodiments, the polymeric bioconjugate linker is formed between a first reactive moiety and a second reactive moiety as described herein. In embodiments, the degradable particle core is a pH-sensitive particle core.

In embodiments, each particle includes a plurality of oligonucleotide moieties covalently attached to said particle via a polymeric bioconjugate linker. In embodiments, the polymeric bioconjugate linker is formed through a reaction between a particle polymer (e.g., a polymer covalently attached to the surface of the particle) including a first bioconjugate reactive moiety and an oligonucleotide including a second bioconjugate reactive moiety. In embodiments, the average longest dimension of the particle is from about 100 nm to about 3000 nm. In embodiments, each particle includes a plurality of oligonucleotide moieties covalently attached to said particle via a bioconjugate linker, wherein the polymeric bioconjugate linker is formed through a reaction between a particle polymer (e.g., a polymer covalently attached to the surface of the particle) including a first bioconjugate reactive moiety (e.g., an azide) and an oligonucleotide including a second bioconjugate reactive moiety (e.g., DBCO). Bioconjugate reactive moieties are described herein, and for example further characterized and described in Hein et al (Pharm Res. 2008 October; 25(10): 2216-2230) and Devaraj and Finn (Chem. Rev. 2021, 121, 12, 6697-6698), both of which are each incorporated herein by reference in their entirety.

In embodiments, each particle includes a plurality of oligonucleotide moieties covalently attached to the particle via a polymeric bioconjugate linker. In embodiments, the polymeric bioconjugate linker is a polymer (i.e., a molecule including structurally unique repeating units) including one or more reacted bioconjugate reactive moieties. In embodiments, the bioconjugate linker is illustrated in Scheme 1. In embodiments, the polymeric bioconjugate linker is a polymer including a subunit of formula Ia, Ib, II, or III as described in U.S. Pat. No. 11,236,387, which is incorporated herein by reference in its entirety and for all purposes.

In embodiments, the particle includes a degradable particle core surrounded by a polymer shell wherein the polymer shell is functionalized for primer attachment. In embodiments, the particle comprises a degradable particle core surrounded by a polymer shell wherein the polymer shell includes a plurality of polymerized units of shell monomers and one or more shell monomers includes an oligonucleotide moiety covalently linked to the shell monomer. In embodiments, the particle (e.g., a nanoparticle) includes a plurality of oligonucleotide moieties covalently attached to the polymer shell via a bioconjugate linker, wherein the bioconjugate linker is formed via a reaction between a particle polymer including a first bioconjugate reactive moiety and an oligonucleotide including a second bioconjugate reactive moiety as described herein. In embodiments, the particle includes a polymer shell (e.g., a polymer or copolymer described herein).

In embodiments, the particle has a degradable particle core that is a metal-organic framework (MOF) particle core. MOFs are a form of a porous coordination polymer. In embodiments, the MOF particle core is an Isoreticular Metal-Organic Framework (IR-MOF) core, Zeolitic Imidazolate Framework (ZIF) core, Porous Coordination Network (PCN) core, Materials Institute Lavoisier (MIL) MOF core, Porous Coordination Polymer (PCP) core, or University of Oslo (UiO) MOF core. In embodiments, the MOF core is a Zeolitic Imidazolate Framework 8 (ZIF-8) core or a UiO-66 MOF core. The aforementioned MOF cores are known in the art, see for example Zhou et al. review article titled "Introduction to Metal-Organic Frameworks" published in Chem. Rev. 2012, 112, 2, 673-674, Furukawa et al. (see Science, vol. 341, No. 6149, 1230444, 2013), and/or Cohen (see Chem. Reviews, Vol. 112, No. 2, p. 970-1000, 2012).

In embodiments, the degradable particle core is a polystyrene (PS) particle, or polymethyl methacrylate (PMMA) particle, or latex particle. In embodiments, the MOF particle is any metal-organic framework particle that can be degraded by a change in external conditions, including a change in pH, temperature, or other chemical degrading agent. In embodiments, the MOF particle is a Zeolitic Imidazolate Framework 8 (ZIF-8) particle. In embodiments, the MOF particle is UiO-66. In embodiments, the MOF particle is a Zr based MOFs, mesoporous iron (III) carboxylate MIL-100(Fe). In embodiments, the degrading the degradable particle core does not destroy or damage the oligonucleotide. In embodiments, the degrading the degradable particle core does not destroy or damage the polymer shell. In embodiments, the MOF particle is as described in Furukawa et al. (see Science, vol. 341, No. 6149, 1230444, 2013) or Cohen (see Chem. Reviews, Vol. 112, No. 2, p. 970-1000, 2012).

In embodiments, the degradable particle core can be removed to release material through the presence of an external stimulus. In embodiments, the external stimulus is a change in pH. In embodiments, the pH is altered with a base to degrade the particle core. In embodiments, the base is NaOH. In embodiments, the pH is altered with an acid to degrade the particle core. In embodiments, the external stimulus is the presence of a compound such as phosphate. In embodiments, degrading the particle core causes the release of the polymer shell. In embodiments, the degradable particle core is degraded under conditions that would not degrade and/or alter an oligonucleotide. In embodiments, the mass of the degradable particle core reduces upon incubation with the external stimulus. In embodiments, the shape of the degradable particle core changes to amorphous upon incubation with the external stimulus.

In embodiments, the particle has a polymer shell surrounding the degradable particle core. In embodiments, the polymer shell includes polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl) cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly (vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (TEM), or a copolymer thereof. In embodiments, the polymer shell includes polymerized units of polyethylene glycol methacrylate (PEGMA) and glicydyl methacrylate (GMA). In embodiments, the polymer shell includes polymerized units of polyethylene glycol methacrylate (PEGMA) and isocyanatoethyl methacrylate (IEM). In embodiments, the polymer shell includes polymerized units of glicydyl methacrylate azide (GMA azide) and polyethylene glycol methacrylate (PEGMA).

In embodiments, the polymer shell includes polymerized units of 3-azido-2-hydroxypropyl methacrylate, 2-azido-3-hydroxypropyl methacrylate, 2-(((2-azidoethoxy)carbonyl) amino)ethyl methacrylate, 3-azido-2-hydroxypropyl acrylate, 2-azido-3-hydroxypropyl acrylate, or 2-(((2-azidoethoxy)carbonyl)amino)ethyl acrylate. In embodiments, the polymer shell includes polymerized units of 3-azido-2-hydroxypropyl methacrylate, 2-azido-3-hydroxypropyl methacrylate, or 2-(((2-azidoethoxy)carbonyl) amino)ethyl methacrylate. In embodiments, the polymer shell includes polymerized units of 3-azido-2-hydroxypropyl methacrylate. In embodiments, the polymer shell includes polymerized units of 3-azido-2-hydroxypropyl methacrylate 2-azido-3-hydroxypropyl methacrylate. In embodiments, the polymer shell includes polymerized units of 3-azido-2-hydroxypropyl methacrylate 2-(((2-azidoethoxy)carbonyl)amino)ethyl methacrylate. In embodiments, the polymer shell includes polymerized units of a) polyethylene glycol methacrylate (PEGMA) and glicydyl methacrylate (GMA), b) polyethylene glycol methacrylate (PEGMA) and isocyanatoethyl methacrylate (IEM), or c) polyethylene glycol methacrylate (PEGMA) and glicydyl methacrylate (GMA) azide. In embodiments, the polymer shell is permeable to a polymerase.

In embodiments, the polymeric gel is porous and/or permeable to fluids, solutes, and solvents. In embodiments, degrading the degradable particle core (e.g., the MOF particle) provides a void, space, and/or a pore within the polymeric gel (e.g., generates a porous polymeric gel). In embodiments, the pores include a diameter substantially similar to the diameter of the original particle. In embodiments, the pores are capable of retaining large polynucleotides (e.g., 10-50 kb polynucleotides do not transit the pore, while remaining selective for medium to small polynucleotides (e.g., less than about 10 kb, less than about 5 kb, or less than about 1 kb polynucleotides).

In embodiments, each polymer layer includes a plurality of oligonucleotide moieties covalently attached to said polymer layer via a polymeric bioconjugate linker. In embodiments, each particle includes a plurality of oligonucleotide moieties covalently attached to said particle via a polymeric bioconjugate linker. In embodiments, the polymeric bioconjugate linker is a polymer (i.e., a molecule including structurally unique repeating units) including one or more reacted bioconjugate reactive moieties. In embodiments, the bioconjugate linker is illustrated in Scheme 1. In embodiments, the polymeric bioconjugate linker is a polymer including a subunit of formula Ia, Ib, II, or III as described in U.S. Pat. No. 11,236,387, which is incorporated herein by reference in its entirety and for all purposes.

In embodiments, the oligonucleotide moiety includes a DBCO bioconjugate reactive moiety that reacts with an azide bioconjugate reactive moiety on the particle polymer and forms a bioconjugate linker that covalently links the oligonucleotide moiety to the particle polymer, for example according to the following scheme:

Scheme 1.

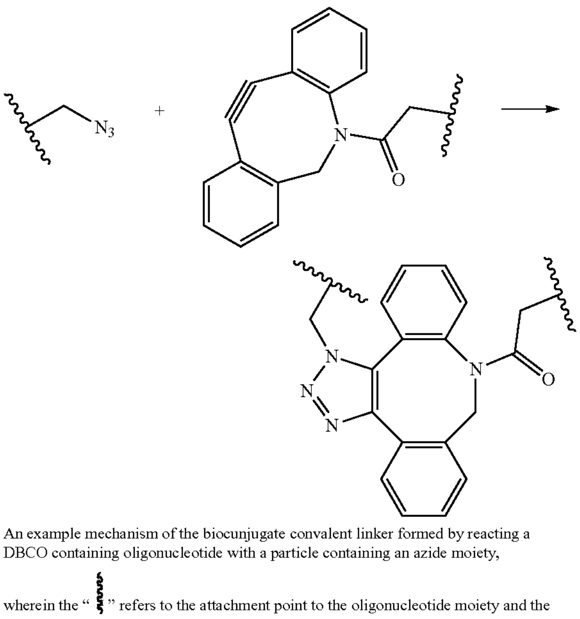

An example mechanism of the biocunjugate convalent linker formed by reacting a DBCO containing oligonucleotide with a particle containing an azide moiety, wherein the "" refers to the attachment point to the oligonucleotide moiety and the particle polymer, respectively.

In embodiments, the particle includes a degradable particle core surrounded by a polymer shell wherein the polymer shell is functionalized for primer attachment. In embodiments, the particle comprises a degradable particle core surrounded by a polymer shell wherein the polymer shell includes a plurality of polymerized units of shell monomers and one or more shell monomers includes an oligonucleotide moiety covalently linked to the shell monomer.

In embodiments, the particle has a degradable particle core that includes a metal-organic framework (MOF) particle. In embodiments, the degradable particle core includes a polystyrene (PS) particle, or polymethyl methacrylate (PMMA) particle, or latex particle. In embodiments, the MOF particle is any metal-organic framework particle that can be degraded by a change in external conditions, including a change in pH, temperature, or other chemical degrading agent. In embodiments, the MOF particle is a Zeolitic Imidazolate Framework 8 (ZIF-8) particle. In embodiments, the MOF particle is UiO-66. In embodiments, the MOF particle is a Zr based MOFs, mesoporous iron (III) carboxylate MIL-100(Fe). In embodiments, the degrading the degradable particle core does not destroy or damage the oligonucleotide.

In embodiments, the degradable particle core can be removed to release material through the presence of an external stimulus. In embodiments, the external stimulus is a change in pH. In embodiments, the pH is altered with a base to degrade the particle core. In embodiments, the base is NaOH. In embodiments, the pH is altered with an acid to degrade the particle core. In embodiments, the external stimulus is the presence of a compound such as phosphate. In embodiments, degrading the particle core causes the release of the polymer shell. In embodiments, the degradable particle core is degraded under conditions that would not degrade and/or alter an oligonucleotide. In embodiments, the mass of the degradable particle core reduces upon incubation with the external stimulus.

In embodiments, the particle has a polymer shell surrounding the degradable particle core. In embodiments, the polymer shell includes polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl) cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly (vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (TEM), or a copolymer thereof. In embodiments, the polymer shell includes polymerized units of polyethylene glycol methacrylate (PEGMA) and glicydyl methacrylate (GMA). In embodiments, the polymer shell includes polymerized units of polyethylene glycol methacrylate (PEGMA) and isocyanatoethyl methacrylate (IEM). In embodiments, the polymer shell includes polymerized units of glicydyl methacrylate azide (GMA azide) and polyethylene glycol methacrylate (PEGMA).

In embodiments, the polymer shell includes polymerized units of 3-azido-2-hydroxypropyl methacrylate, 2-azido-3-hydroxypropyl methacrylate, 2-(((2-azidoethoxy)carbonyl) amino)ethyl methacrylate, 3-azido-2-hydroxypropyl acrylate, 2-azido-3-hydroxypropyl acrylate, or 2-(((2-azidoethoxy)carbonyl)amino)ethyl acrylate. In embodiments, the polymer shell includes polymerized units of 3-azido-2-hydroxypropyl methacrylate, 2-azido-3-hydroxypropyl methacrylate, or 2-(((2-azidoethoxy)carbonyl) amino)ethyl methacrylate. In embodiments, the polymer shell includes polymerized units of 3-azido-2-hydroxypropyl methacrylate. In embodiments, the polymer shell includes polymerized units of 3-azido-2-hydroxypropyl methacrylate 2-azido-3-hydroxypropyl methacrylate. In embodiments, the polymer shell includes polymerized units of 3-azido-2-hydroxypropyl methacrylate 2-(((2-azidoethoxy)carbonyl)amino)ethyl methacrylate. In embodiments, the polymer shell includes polymerized units of a) polyethylene glycol methacrylate (PEGMA) and glicydyl methacrylate (GMA), b) polyethylene glycol methacrylate (PEGMA) and isocyanatoethyl methacrylate (IEM), or c) polyethylene glycol methacrylate (PEGMA) and glicydyl methacrylate (GMA) azide. In embodiments, the polymer shell is permeable to a polymerase.

In embodiments, the polymer shell includes polymerized units of glicydyl methacrylate azide (GMA azide) and polyethylene glycol methacrylate (PEGMA) in the ratio of 1:1. In embodiments, the ratio of GMA azide to PEGMA is 1:2. In embodiments, the ratio of GMA azide to PEGMA is 1:3. In embodiments, the ratio of GMA azide to PEGMA is 1:4. In embodiments, the ratio of GMA azide to PEGMA is 1:5. In embodiments, the ratio of GMA azide to PEGMA is 1:6. In embodiments, the ratio of GMA azide to PEGMA is 1:7. In embodiments, the ratio of GMA azide to PEGMA is 1:8.

The polymer shell may be polymerized from a mixture of functionalized and non-functionalized monomers, such that at least some functionalized monomers that provide attachment points (e.g., azide moieties) for primers (e.g., DBCO-containing oligonucleotide primers) are spaced from one another by one or more monomers lacking such attachment points (e.g., PEG or AAm). The frequency of monomer units attached to primers within a polymer can be adjusted by changing the concentration of the corresponding functionalized monomer in the mixture of monomers. In embodiments, monomer units of the polymer that are attached to a polynucleotide primer (referred to herein as oligonucleotide moieties) are separated by, on average, about or at least about 1, 2, 3, 4, 5, 6, 7, 8, 9, 10, 15, 20, 25, 30, 40, 50, or more monomer units that are not attached to a primer, referred to herein as (ng). In embodiments, monomer units of the polymer that are attached to a polynucleotide primer are separated by, on average, about or at least about 4 to 8 monomer units that are not attached to a primer. In embodiments, monomer units of the polymer that are attached to a polynucleotide primer are separated by, on average, about or at least about 6, 7, or 8 monomer units that are not attached to a primer. In embodiments, primer-attached monomers are separated by, on average, about 1-50, 2-40, 3-30, 4-25, or 5-20 monomers not attached to primers. In embodiments, monomer units of the polymer that are attached to a polynucleotide primer are separated by 3 monomer units that are not attached to a primer (aka 3 ng). In embodiments, monomer units of the polymer that are attached to a polynucleotide primer are separated by 6 ng. In embodiments, monomer units the polymer that are attached to a polynucleotide primer are separated by 9 ng. The mixture can include monomers with different functional groups (e.g., azides, alkynes, DBCO, etc.) as described herein.

In embodiments, the average longest dimension of the particle is from about 100 nm to about 3000 nm. In embodiments, the average longest dimension of the particle is from about 200 nm to about 2900 nm. In embodiments, the average longest dimension of the particle is from about 300 nm to about 2800 nm. In embodiments, the average longest dimension of the particle is from about 400 nm to about 2700 nm. In embodiments, the average longest dimension of the particle is from about 500 nm to about 2600 nm. In embodiments, the average longest dimension of the particle is from about 600 nm to about 2500 nm. In embodiments, the average longest dimension of the particle is from about 700 nm to about 2400 nm. In embodiments, the average longest dimension of the particle is from about 800 nm to about 2300 nm. In embodiments, the average longest dimension of the particle is from about 900 nm to about 2200 nm. In embodiments, the average longest dimension of the particle is from about 1000 nm to about 2100 nm. In embodiments, the average longest dimension of the particle is from about 900 nm to about 2000 nm. In embodiments, the average longest dimension of the particle is from about 150 nm to about 600 nm. In some embodiments, the average longest dimension of the particle is from about 350 nm to about 600 nm. In some embodiments, the average longest dimension of the particle is from about 400 nm to about 500 nm. In some embodiments, the average longest dimension of the particle is about 500 nm. In some embodiments, the average longest dimension of the particle is about 400 nm. In some embodiments, the average longest dimension of the particle is about 400 nm, 450 nm, 500 nm, or 550 nm. In some embodiments, the average longest dimension of the particle is about 410 nm, 420 nm, 430 nm, 440 nm or 450 nm. In some embodiments, the average longest dimension of the particle is about 460 nm, 470 nm, 480 nm, 490 nm or 500 nm. In embodiments, the average longest dimension of the particle is at least, about, or at most 100, 200, 300, 400, 500, 600, 700, 800, 900, 1000 nm or a number or a range between any two of these values. In embodiments, the average longest dimension of the degradable particle core is from about 100 nm to about 3000 nm. In embodiments, the average longest dimension of the degradable particle core is from about 200 nm to about 2900 nm. In embodiments, the average longest dimension of the degradable particle core is from about 300 nm to about 2800 nm. In embodiments, the average longest dimension of the degradable particle core is from about 400 nm to about 2700 nm. In embodiments, the average longest dimension of the degradable particle core is from about 500 nm to about 2600 nm. In embodiments, the average longest dimension of the degradable particle core is from about 600 nm to about 2500 nm. In embodiments, the average longest dimension of the degradable particle core is from about 700 nm to about 2400 nm. In embodiments, the average longest dimension of the degradable particle core is from about 800 nm to about 2300 nm. In embodiments, the average longest dimension of the degradable particle core is from about 900 nm to about 2200 nm. In embodiments, the average longest dimension of the degradable particle core is from about 1000 nm to about 2100 nm. In embodiments, the average longest dimension of the degradable particle core is from about 900 nm to about 2000 nm. In embodiments, the average longest dimension of the degradable particle core is from about 150 nm to about 600 nm. In some embodiments, the average longest dimension of the degradable particle core is from about 350 nm to about 600 nm. In some embodiments, the average longest dimension of the degradable particle core is from about 400 nm to about 500 nm. In some embodiments, the average longest dimension of the degradable particle core is about 500 nm. In some embodiments, the average longest dimension of the degradable particle core is about 400 nm. In some embodiments, the average longest dimension of the degradable particle core is about 400 nm, 450 nm, 500 nm, or 550 nm. In some embodiments, the average longest dimension of the degradable particle core is about 410 nm, 420 nm, 430 nm, 440 nm or 450 nm. In some embodiments, the average longest dimension of the degradable particle core is about 460 nm, 470 nm, 480 nm, 490 nm or 500 nm. In embodiments, the average longest dimension of the degradable particle core is at least, about, or at most 100, 200, 300, 400, 500, 600, 700, 800, 900, 1000 nm or a number or a range between any two of these values. In embodiments, the shell diameter is about 0.1-10 microns, 0.25-5 microns, 0.5-2 microns, 1 micron, or a number or a range between any two of these values. In embodiments, the particle shell diameter is at least, about, or at most 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 μm or a number or a range between any two of these values. In embodiments, the core diameter is about 150-700 nanometers, and/or the shell diameter is about 0.25-5 μm (microns).

In embodiments, the average longest dimension of the nanoparticle is from about 100 nm to about 400 nm. In embodiments, the average longest dimension of the nanoparticle is about 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average longest dimension of the nanoparticle is from about 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm. In embodiments, the average longest dimension of the nanoparticle is less than about 1000 nm. In embodiments, the average longest dimension of the nanoparticle is less than about 900 nm. In embodiments, the average longest dimension of the nanoparticle is less than about 800 nm. In embodiments, the average longest dimension of the nanoparticle is less than about 700 nm. In embodiments, the average longest dimension of the nanoparticle is less than about 600 nm. In embodiments, the average longest dimension of the nanoparticle is less than about 500 nm. In embodiments, the average longest dimension of the nanoparticle is less than about 400 nm. In embodiments, the average longest dimension of the nanoparticle is less than about 300 nm. In embodiments, the average longest dimension of the nanoparticle is less than about 200 nm. In embodiments, the average longest dimension of the nanoparticle is less than about 100 nm. In embodiments, the average longest dimension of the nanoparticle is 400 nm without the particle shell.

In embodiments, the particle includes a plurality of bioconjugate reactive moieties. In embodiments, a bioconjugate reactive moiety includes an amine moiety, aldehyde moiety, alkyne moiety, azide moiety, carboxylic acid moiety, dibenzocyclooctyne (DBCO) moiety, norbornene moiety, tetrazine moiety, epoxy moiety, isocyanate moiety, furan moiety, maleimide moiety, thiol moiety, or transcyclooctene (TCO) moiety. In embodiments, the particle includes a plurality of azide moieties, alkyne moieties, dibenzocyclooctyne (DBCO) moieties, norbornene moieties, epoxy moieties, or isocyanate moieties. In some embodiments, the particle includes a plurality of oligonucleotide moieties (e.g., ssDNA moieties) covalently attached via a bioconjugate linker to the polymer shell. The bioconjugate linker is the product of a reaction between the two bioconjugate group (e.g. click chemistry group). In embodiments, each of the plurality of bioconjugate reactive moieties includes an amine moiety, aldehyde moiety, alkyne moiety, azide moiety, carboxylic acid moiety, dibenzocyclooctyne (DBCO) moiety, norbornene moiety, tetrazine moiety, epoxy moiety, isocyanate moiety, furan moiety, maleimide moiety, thiol moiety, or transcyclooctene (TCO) moiety. In embodiments, each of the plurality of bioconjugate reactive moieties include an amine moiety, azide moiety, dibenzocyclooctyne (DBCO) moiety, epoxy moiety, or isocyanate moiety. In embodiments, each of the plurality of bioconjugate reactive moieties include an amine moiety, azide moiety, alkyne moiety, dibenzocyclooctyne (DBCO) moiety, epoxy moiety, or isocyanate moiety. In embodiments, the bioconjugate reactive moiety is an azido moiety.

In embodiments, each particle includes multiple copies of one or more oligonucleotide moieties. In embodiments, the one or more oligonucleotide moieties include at least two different primers attached to the polymer (e.g., a forward and a reverse primer), each of which may be present in multiple copies. In embodiments, about or at most at most about 50%, 40%, 30%, 25%, 20%, 15%, 10%, 5%, or less of the monomers in the polymer of each particle are attached to a copy of the oligonucleotide moiety. In embodiments, about 1-25%, about 2-20%, about 3-15%, about 4-14%, or about 5-12% of the monomers in the polymer of each particle are attached to a copy of the oligonucleotide moiety, or a number or a range between any two of these values. In embodiments, about 5-10% of the monomers in the polymer of each particle are attached to a copy of the oligonucleotide moiety. In embodiments, two different oligonucleotide moieties are attached to the particle (e.g., a forward and a reverse primer), which facilitates generating multiple amplification products from the first extension product or a complement thereof.

In embodiments, the particle includes a first plurality of oligonucleotide moieties and a second plurality of oligonucleotide moieties. The first plurality of oligonucleotide moieties is different from the second plurality of oligonucleotide moieties. In embodiments, the particle has a plurality of oligonucleotide moieties that is about 10 to about 250 nucleotides in length. In embodiments, the particle has a plurality of oligonucleotide moieties that is about 15 to about 60 nucleotides in length. In embodiments, each of the particles include substantially the same oligonucleotide moieties (e.g., a first population of oligonucleotide moieties and a different second population of oligonucleotide moieties). In embodiments, each of the particles comprise at least two species of substantially the same oligonucleotide moieties (i.e., the same sequences). In embodiments, each particle includes a first plurality of a platform primer sequence and a second plurality of a differing platform primer sequence. In embodiments, the platform primer sequence is used during amplification reactions (e.g., solid phase amplification). In embodiments, each particle includes oligonucleotide moieties capable of annealing to an adapter of a library nucleic acid molecule. The term "library" merely refers to a collection or plurality of template nucleic acid molecules which share common sequences at their 5' ends (e.g., the first end) and common sequences at their 3' ends (e.g., the second end). The term "adapter" as used herein refers to any linear oligonucleotide that can be ligated to a nucleic acid molecule, thereby generating nucleic acid products that can be sequenced on a sequencing platform (e.g., an Illumina or Singular Genomics sequencing platform). In embodiments, adapters include two reverse complementary oligonucleotides forming a double-stranded structure. In embodiments, an adapter includes two oligonucleotides that are complementary at one portion and mismatched at another portion, forming a Y-shaped or fork-shaped adapter that is double stranded at the complementary portion and has two overhangs at the mismatched portion. Since Y-shaped adapters have a complementary, double-stranded region, they can be considered a special form of double-stranded adapters. When this disclosure contrasts Y-shaped adapters and double stranded adapters, the term "double-stranded adapter" or "blunt-ended" is used to refer to an adapter having two strands that are fully complementary, substantially (e.g., more than 90% or 95%) complementary, or partially complementary. In embodiments, adapters include sequences that bind to sequencing primers. In embodiments, adapters include sequences that bind to immobilized oligonucleotides (e.g., P7 and P5 sequences) or reverse complements thereof. In embodiments, the adapter is substantially non-complementary to the 3' end or the 5' end of any target polynucleotide present in the sample. In embodiments, the adapter can include a sequence that is substantially identical, or substantially complementary, to at least a portion of a primer, for example a universal primer. In embodiments, the adapter can include an index sequence (also referred to as barcode or tag) to assist with downstream error correction, identification or sequencing. In embodiments, each of the particles include at least two populations of substantially the same oligonucleotide moieties.

In some embodiments, the oligonucleotide moiety is about 5 to about 250 nucleotides in length. In some embodiments, the oligonucleotide moiety is about 5 to about 200 nucleotides in length. In some embodiments, the oligonucleotide moiety is about 5 to about 150 nucleotides in length. In some embodiments, the oligonucleotide moiety is about 5 to about 100 nucleotides in length. In some embodiments, the oligonucleotide moiety is about 5 to about 60 nucleotides in length. In some embodiments, the oligonucleotide moiety is about 5 to about 50 nucleotides in length. In some embodiments, the oligonucleotide moiety is about 5 to about 40 nucleotides in length. In some embodiments, the oligonucleotide moiety is about 10 to about 250 nucleotides in length. In some embodiments, the oligonucleotide moiety is about 10 to about 200 nucleotides in length. In some embodiments, the oligonucleotide moiety is about 10 to about 150 nucleotides in length. In some embodiments, the oligonucleotide moiety is about 10 to about 100 nucleotides in length. In some embodiments, the oligonucleotide moiety is about 10 to about 60 nucleotides in length. In some embodiments, the oligonucleotide moiety is about 10 to about 50 nucleotides in length. In some embodiments, the oligonucleotide moiety is about 10 to about 45 nucleotides in length. In some embodiments, the oligonucleotide moiety is about 10 to about 40 nucleotides in length. In some embodiments, the oligonucleotide moiety is about 15 to about 100 nucleotides in length. In some embodiments, the oligonucleotide moiety is about 15 to about 90 nucleotides in length. In some embodiments, the oligonucleotide moiety is about 15 to about 80 nucleotides in length. In some embodiments, the oligonucleotide moiety is about 15 to about 70 nucleotides in length. In some embodiments, the oligonucleotide moiety is about 15 to about 60 nucleotides in length. In some embodiments, the oligonucleotide moiety is about 15 to about 50 nucleotides in length. In some embodiments, the oligonucleotide moiety is about 15 to about 40 nucleotides in length. In some embodiments, the oligonucleotide moiety is about 15 to about 30 nucleotides in length. In some embodiments, the oligonucleotide moiety is about 20 to about 35 nucleotides in length. In some embodiments, the oligonucleotide moiety is about 20 to about 30 nucleotides in length. In some embodiments, the oligonucleotide moiety is about 25 to about 30 nucleotides in length. In some embodiments, the oligonucleotide moiety is about 25 to about 35 nucleotides in length. In some embodiments, the oligonucleotide moiety is about 30 to about 50 nucleotides in length. In some embodiments, the oligonucleotide moiety is about 30 to about 75 nucleotides in length. In some embodiments, the oligonucleotide moiety is about 50 to about 150 nucleotides in length. In some embodiments, the oligonucleotide moiety is about 75 to about 200 nucleotides in length.

In embodiments, the oligonucleotide moiety includes spacer nucleotides. Including spacer nucleotides in the linker puts the target polynucleotide in an environment having a greater resemblance to free solution. This can be beneficial, for example, in enzyme-mediated reactions such as sequencing-by-synthesis. It is believed that such reactions suffer less steric hindrance issues that can occur when the polynucleotide is directly attached to the particle or is attached through a very short linker (e.g., a linker comprising about 1 to 3 carbon atoms). Spacer nucleotides form part of the oligonucleotide moiety but do not participate in any reaction carried out on or with the oligonucleotide (e.g., a hybridization or amplification reaction). In embodiments, the spacer nucleotides include 1 to 20 nucleotides. In embodiments, the linker includes 10 spacer nucleotides. In embodiments, the linker includes 12 spacer nucleotides. In embodiments, the linker includes 15 spacer nucleotides. It is preferred to use polyT spacers, although other nucleotides and combinations thereof can be used. In embodiments, the linker includes 10, 11, 12, 13, 14, or 15 T spacer nucleotides. In embodiments, the linker includes 12 T spacer nucleotides. Spacer nucleotides are typically included at the 5' ends of oligonucleotide which are attached to the particle. Attachment can be achieved via a phosphorothioate present at the 5' end of the oligonucleotide, an azide moiety, a dibenzocyclooctyne (DBCO) moiety, or any other bioconjugate reactive moiety. The linker may be a carbon-containing chain such as those of formula $—(CH_2)n-$ wherein "n" is from 1 to about 1000. However, a variety of other linkers may be used so long as the linkers are stable under conditions used in DNA sequencing. In embodiments, the linker includes polyethylene glycol (PEG) having a general formula of $—(CH_2—CH_2\text{-}0)m-$, wherein m is an integer from about 1 to 500.

In embodiments, the linker, or the oligonucleotides (e.g., primers) include a cleavable site. A cleavage site is a site which allows controlled cleavage of the immobilized polynucleotide strand (e.g., the linker, the primer, or the polynucleotide) by chemical, enzymatic or photochemical means. Any suitable enzymatic, chemical, or photochemical cleavage reaction may be used to cleave the cleavage site. The cleavage reaction may result in removal of a part or the whole of the strand being cleaved. Suitable cleavage means include, for example, restriction enzyme digestion, in which case the cleavage site is an appropriate restriction site for the enzyme which directs cleavage of one or both strands of a duplex template; RNase digestion or chemical cleavage of a bond between a deoxyribonucleotide and a ribonucleotide, in which case the cleavage site may include one or more ribonucleotides; chemical reduction of a disulfide linkage with a reducing agent (e.g., THPP or TCEP), in which case the cleavage site should include an appropriate disulfide linkage; chemical cleavage of a diol linkage with periodate, in which case the cleavage site should include a diol linkage; generation of an abasic site and subsequent hydrolysis, etc. In embodiments, the cleavage site is included in the oligonucleotide (e.g., within the oligonucleotide sequence of the primer). In embodiments, the linker or the oligonucleotide, includes a diol linkage which permits cleavage by treatment with periodate (e.g., sodium periodate). It will be appreciated that more than one diol can be included at the cleavage site. One or more diol units may be incorporated into a polynucleotide using standard methods for automated chemical DNA synthesis. Oligonucleotide nucleotide primers including one or more diol linkers can be conveniently prepared by chemical synthesis. The diol linker is cleaved by treatment with any substance which promotes cleavage of the diol (e.g., a diol-cleaving agent). In embodiments, the diol-cleaving agent is periodate, e.g., aqueous sodium periodate ($NaIO_4$). Following treatment with the diol-cleaving agent (e.g., periodate) to cleave the diol, the cleaved product may be treated with a "capping agent" in order to neutralize reactive species generated in the cleavage reaction. Suitable capping agents for this purpose include amines, e.g., ethanolamine or propanolamine. In embodiments, cleavage may be accomplished by using a modified nucleotide as the cleavable site (e.g., uracil, 8oxoG, 5-mC, 5-hmC) that is removed or nicked via a corresponding DNA glycosylase, endonuclease, or combination thereof.

In embodiments, each of the particle-immobilized oligonucleotides (e.g., immobilized primers) is about 5 to about 25 nucleotides in length. In embodiments, each of the particle-immobilized oligonucleotides (e.g., immobilized primers) is about 10 to about 40 nucleotides in length. In embodiments, each of the particle-immobilized oligonucleotides (e.g., immobilized primers) is about 15 to 60 nucleotides in length. In embodiments, each of the particle-immobilized oligonucleotides (e.g., immobilized primers) is about 5 to about 100 nucleotides in length. In embodiments, each of the particle-immobilized oligonucleotides (e.g., immobilized primers) is about 20 to 200 nucleotides in length. In embodiments, each of the particle-immobilized oligonucleotides (e.g., immobilized primers) about or at least about 5, 6, 7, 8, 9, 10, 12, 15, 18, 20, 25, 30, 35, 40, 50 or more nucleotides in length. In embodiments, one or more particle-immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, the 3' modification is a 3'-phosphate modification includes a 3' phosphate moiety, which is removed by a PNK enzyme. In embodiments, each of the immobilized oligonucleotides (e.g., immobilized primers) is about 5 to about 25 nucleotides in length. In embodiments, each of the immobilized oligonucleotides (e.g., immobilized primers) is about 10 to about 40 nucleotides in length. In embodiments, each of the immobilized oligonucleotides (e.g., immobilized primers) is about 15 to 60 nucleotides in length. In embodiments, each of the immobilized oligonucleotides (e.g., immobilized primers) is about 5 to about 100 nucleotides in length. In embodiments, each of the immobilized oligonucleotides (e.g., immobilized primers) is about 20 to 200 nucleotides in length. In embodiments, each of the immobilized oligonucleotides (e.g., immobilized primers) about or at least about 5, 6, 7, 8, 9, 10, 12, 15, 18, 20, 25, 30, 35, 40, 50 or more nucleotides in length. In embodiments, one or more immobilized oligonucleotides include blocking groups at their 3' ends that prevent polymerase extension.

In embodiments, the plurality of oligonucleotide primers form covalent attachments (i.e., bioconjugate linkers) to one or more components and/or crosslinking agents in the polymer through bioconjugate reactive moieties. In embodiments, the 5' end of the primer contains a functional group that is capable of reacting with a complementary group so the primer may be tethered to the polymer. In embodiments, the primers may be used to aid in tethering the extension product to a confined area and may not be extended. In embodiments, the immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, the method includes extending the one or more immobilized oligonucleotides hybridized to an extension product with a polymerase. For example, the one or more immobilized oligonucleotides may be used to aid in tethering the extension product to a localized area and may be extended in an exponential RCA amplification reaction. In embodiments, the 5' end of the primer is covalently attached to a cellular component. In embodiments, the 5' end of the primer is covalently attached to the polymer.

In embodiments, the amplification method includes a standard dNTP mixture including dATP, dCTP, dGTP and dTTP (for DNA) or dATP, dCTP, dGTP and dUTP (for RNA). In embodiments, the amplification method includes a mixture of standard dNTPs and modified nucleotides that contain functional moieties (e.g., bioconjugate reactive groups) that serve as attachment points to the polymer matrix (e.g. a hydrogel). In embodiments, the amplification method includes a mixture of standard dNTPs and modified nucleotides that contain functional moieties (e.g., bioconjugate reactive groups) that participate in the formation of a bioconjugate linker. The modified nucleotides may react and link the amplification product to the surrounding scaffold. For example, amplifying may include an extension reaction wherein the polymerase incorporates a modified nucleotide into the amplification product, wherein the modified nucleotide includes a bioconjugate reactive moiety (e.g., an alkynyl moiety) attached to the nucleobase. The bioconjugate reactive moiety of the modified nucleotide participates in the formation of a bioconjugate linker by reacting with a complementary bioconjugate reactive moiety present in the polymer (e.g., a crosslinking agent, such as NHS-PEG-azide, or an amine moiety) thereby attaching the amplification product to the internal scaffold polymer layer. In embodiments, the functional moiety can be covalently cross-linked, copolymerize with or otherwise non-covalently bound to the matrix. In embodiments, the functional moiety can react with a cross-linker. In embodiments, the functional moiety can be part of a ligand-ligand binding pair. Suitable exemplary functional moieties include an amine, acrydite, alkyne, biotin, azide, and thiol. In embodiments of cross-linking, the functional moiety is cross-linked to modified dNTP or dUTP or both. In embodiments, suitable exemplary cross-linker reactive groups include imidoester (DMP), succinimide ester (NHS), maleimide (Sulfo-SMCC), carbodiimide (DCC, EDC) and phenyl azide. Cross-linkers within the scope of the present disclosure may include a spacer moiety. In embodiments, such spacer moieties may be functionalized. In embodiments, such spacer moieties may be chemically stable. In embodiments, such spacer moieties may be of sufficient length to allow amplification of the nucleic acid bound to the polymer matrix. In embodiments, suitable exemplary spacer moieties include polyethylene glycol, carbon spacers, photo-cleavable spacers and other spacers known to those of skill in the art and the like. In embodiments, amplification reactions include standard dNTPs and a modified nucleotide (e.g., amino-allyl dUTP, 5-TCO-PEG4-dUTP, $C_8$-Alkyne-dUTP, 5-Azidomethyl-dUTP, 5-Vinyl-dUTP, or 5-Ethynyl dLTTP). For example, during amplification a mixture of standard dNTPs and aminoallyl deoxyuridine 5'-triphosphate (dUTP) nucleotides may be incorporated into the amplicon and subsequently cross-linked to the polymer matrix by using a cross-linking reagent (e.g., an amine-reactive crosslinking agent with PEG spacers, such as (PEGylated bis(sulfosuccinimidyl)suberate) $(BS(PEG)_9)$). In embodiments, one or more nucleotides within the amplification primer sequence, the sequencing primer sequence, and/or the immobilized oligonucleotide primer(s) contains one or more functional moieties (e.g., bioconjugate reactive groups) that serve as attachment points to the polymer layer (e.g. a hydrogel).

In embodiments, the oligonucleotide moiety includes one or more phosphorothioate nucleotides. In embodiments, the oligonucleotide moiety includes a plurality of phosphorothioate nucleotides. In embodiments, about or at least about 20%, 30%, 40%, 50%, 60%, 70%, 80%, 90%, or about 100% of the nucleotides in the oligonucleotide moiety are phosphorothioate nucleotides. In embodiments, most of the nucleotides in the oligonucleotide moiety are phosphorothioate nucleotides. In embodiments, all of the nucleotides in the oligonucleotide moiety are phosphorothioate nucleotides. In embodiments, none of the nucleotides in the oligonucleotide moiety are phosphorothioate nucleotides.

In some embodiments, the oligonucleotide moiety is capable of hybridizing to a complementary sequence of a template nucleic acid. In embodiments, the oligonucleotide moiety includes DNA. In embodiments, the oligonucleotide moiety includes RNA. In embodiments, the oligonucleotide moiety is DNA. In embodiments, the oligonucleotide moiety is RNA. In embodiments, the oligonucleotide moiety includes a single-stranded DNA. In embodiments, the oligonucleotide moiety includes a single-stranded RNA. In embodiments, the oligonucleotide moiety is a single-stranded DNA. In embodiments, the oligonucleotide moiety is a single-stranded RNA. In embodiments, the oligonucleotide moiety is a nucleic acid sequence complementary to a target polynucleotide (e.g., complementary to a common adapter sequence of the target polynucleotide).

In an aspect is provided a composition including two or more contiguous layered units, wherein each of the two or more contiguous layered units includes a first layer and a third layer, wherein each first and third layer includes a polymeric gel including a plurality of oligonucleotides attached to the polymeric gel, wherein every first and third layer of the two or more contiguous layered units is separated by a second layer including a passive polymeric gel, wherein the passive polymeric gel does not include a plurality of oligonucleotides attached to the passive polymeric gel. In embodiments, the plurality of oligonucleotides of each of the two or more contiguous layered units is covalently attached to the polymeric gel.

In an aspect is provided a composition including two or more layers, wherein each of the two or more layers includes a polymeric gel including a plurality of oligonucleotides attached to the polymeric gel, wherein every two layers of the two or more layers is separated by a layer including a passive polymeric gel, wherein the passive polymeric gel does not include a plurality of oligonucleotides attached to the passive polymeric gel. In embodiments, the plurality of oligonucleotides of each of the two or more layers is covalently attached to the polymeric gel.

In embodiments of the methods and compositions provided herein, the amplification products (alternatively referred to herein as amplicon clusters, or clusters) have a mean or median separation from one another of about 0.5-5 μm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 μm or a number or a range between any two of these values. In embodiments, the mean or median separation is about 0.1-10 microns. In embodiments, the mean or median separation is about 0.25-5 microns. In embodiments, the mean or median separation is about 0.5-2 microns. In embodiments, the mean or median separation is about or at least about 0.1 μm. In embodiments, the mean or median separation is about or at least about 0.25 μm. In embodiments, the mean or median separation is about or at least about 0.5 μm. In embodiments, the mean or median separation is about or at least about 1.0 μm. In embodiments, the mean or median separation is about or at least about 2.0 μm. In embodiments, the mean or median separation is about or at least about 5.0 μm. In embodiments, the mean or median separation is about or at least about 10 μm. The mean or median separation may be measured center-to-center (i.e., the center of one cluster to the center of a second cluster). In embodiments of the methods provided herein, the amplicon clusters have a mean or median separation (measured center-to-center) from one another of about 0.5-5 μm. The mean or median separation may be measured edge-to-edge (i.e., the edge of one amplicon cluster to the edge of a second amplicon cluster). In embodiments of the methods provided herein, the amplicon clusters have a mean or median separation (measured edge-to-edge) from one another of about 0.2-5 μm.

In embodiments of the methods provided herein, the amplicon clusters have a mean or median diameter of about 100-2000 nm, or about 200-1000 nm. In embodiments, the mean or median diameter is about 100-3000 nanometers, about 500-2500 nanometers, about 1000-2000 nanometers, or a number or a range between any two of these values. In embodiments, the mean or median diameter is about or at most about 100, 200, 300, 400, 500, 600, 700, 800, 900, 1,000, 1,100, 1,200, 1,300, 1,400, 1,500, 1,600, 1,700, 1,800, 1,900, 2000 nanometers or a number or a range between any two of these values. In embodiments, the mean or median diameter is about 100-3,000 nanometers. In embodiments, the mean or median diameter is about 100-2000 nanometers. In embodiments, the mean or median diameter is about 500-2500 nanometers. In embodiments, the mean or median diameter is about 200-1000 nanometers.

In embodiments, the mean or median diameter is about 1,000-2,000 nanometers. In embodiments, the mean or median diameter is about or at most about 100 nanometers. In embodiments, the mean or median diameter is about or at most about 200 nanometers. In embodiments, the mean or median diameter is about or at most about 500 nanometers. In embodiments, the mean or median diameter is about or at most about 1,000 nanometers. In embodiments, the mean or median diameter is about or at most about 2,000 nanometers. In embodiments, the mean or median diameter is about or at most about 2,500 nanometers. In embodiments, the mean or median diameter is about or at most about 3,000 nanometers.

In embodiments, the composition includes a solid support including a polymer layer. In embodiments, the polymer layer includes polymerized units of alkoxysilyl methacrylate, alkoxysilyl acrylate, alkoxysilyl methylacrylamide, alkoxysilyl methylacrylamide, or a copolymer thereof. In embodiments, the polymer layer includes polymerized units of alkoxysilyl methacrylate. In embodiments, the polymer layer includes polymerized units of alkoxysilyl acrylate. In embodiments, the polymer layer includes polymerized units of alkoxysilyl methylacrylamide. In embodiments, the polymer layer includes polymerized units of alkoxysilyl methylacrylamide. In embodiments, the polymer layer includes glycidyloxypropyl-trimethyloxysilane. In embodiments, the polymer layer includes methacryloxypropyl-trimethoxysilane. In embodiments, the polymer layer includes polymerized units of

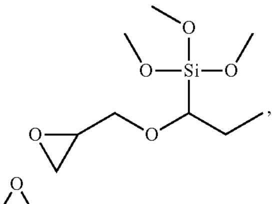
,

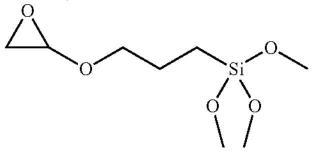
,

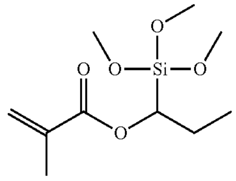
, or

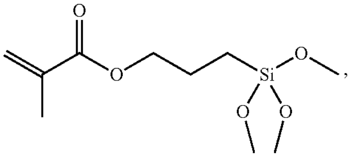
, or a copolymer thereof.

In embodiments, the composition includes a solid support including a passivated polymer layer (alternatively referred to as a passivated polymer coating). In embodiments, the solid support comprises a passivated polymer layer, wherein the passivated polymer layer includes an amphiphilic copolymer. The term "amphiphilic copolymer" is used in accordance with its ordinary meaning and refers to a copolymer composed of polymerized hydrophilic (e.g., PEG monomers and hydrophobic monomers (e.g., alkoxysilyl or (poly(propylene oxide) monomers). The term "amphiphilic copolymer" is used in accordance with its ordinary meaning and refers to a copolymer composed of polymerized hydrophilic (e.g., PEG monomers or HEMA monomers) and hydrophobic monomers (e.g., alkoxysilyl or (poly(propylene oxide) monomers). Amphiphilic copolymers can have both hydrophilic and hydrophobic properties. In embodiments, the polymer layer includes an amphiphilic acrylate copolymer or amphiphilic methacrylate copolymer.

In embodiments, the amphiphilic (co)polymer includes a poloxamer. In some embodiments, the solid support includes a poloxamer layer. In some embodiments, the poloxamer is a polyoxyethylene-polyoxypropylene copolymers. In some embodiments, the poloxamer is poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, and poloxamer 407. In embodiments, the poloxamer is poloxamer 184, poloxamer 188, poloxamer 338, or poloxamer 407 (also known as F127).

In embodiments, the solid support includes a passivated polymer layer, wherein the passivated polymer layer includes a brush copolymer or a comb polymer. A comb polymer includes a main polymer chain with two or more three-way branch points and linear side chains. A brush polymer includes a main polymer chain with linear, unbranched side chains and where one or more of the branch points has four-way functionality or larger. In embodiments, the passivated polymer layer does not include oligonucleotide moieties. In embodiments, the passivated polymer layer is substantially free of oligonucleotides. In embodiments, the passivated polymer layer does not include oligonucleotide capture moieties. In embodiments, the passivated polymer layer binds to the resist of the array.

In embodiments, the solid support includes a photoresist, alternatively referred to herein as a resist. A "resist" as used herein is used in accordance with its ordinary meaning in the art of lilthography and refers to a polymer matrix (e.g., a polymer network). In embodiments, the photoresist is a silsesquioxane resist, an epoxy-based polymer resist, poly (vinylpyrrolidone-vinyl acrylic acid) copolymer resist, an Off-stoichiometry thiol-enes (OSTE) resist, amorphous fluoropolymer resist, a crystalline fluoropolymer resist, polysiloxane resist, or a organically modified ceramic polymer resist. In embodiments, the photoresist is a silsesquioxane resist. In embodiments, the photoresist is an epoxy-based polymer resist. In embodiments, the photoresist is a poly(vinylpyrrolidone-vinyl acrylic acid) copolymer resist. In embodiments, the photoresist is an Off-stoichiometry thiol-enes (OSTE) resist. In embodiments, the photoresist is an amorphous fluoropolymer resist. In embodiments, the photoresist is a crystalline fluoropolymer resist. In embodiments, the photoresist is a polysiloxane resist. In embodiments, the photoresist is an organically modified ceramic polymer resist. In embodiments, the photoresist includes polymerized alkoxysilyl methacrylate polymers and metal oxides (e.g., $SiO_2$, ZrO, MgO, $Al_2O_3$, $TiO_2$ or $Ta_2O_5$). In embodiments, the photoresist includes polymerized alkoxysilyl acrylate polymers and metal oxides (e.g., $SiO_2$, ZrO, MgO, $Al_2O_3$, $TiO_2$ or $Ta_2O_5$). In embodiments, the photoresist includes metal atoms, such as Si, Zr, Mg, Al, Ti, and/or Ta atoms.

In some embodiments, the solid support includes a hydrophobic polymer layer. In embodiments, the solid support includes a perfluorinated polymer. In embodiments, the solid support includes a polyfluorinated polymer. In embodiments, the solid support includes polymerized units of a fluorine-containing methacrylate (e.g., $CH_2{=}C(CH_3)COOC—(CF_3)_2CF_2CF_2CF_3$). Non-limiting examples and synthetic protocols of fluorine-containing methacrylate monomers may be found in Zhang, D., (2018). Materials (Basel, Switzerland), 11(11), 2258 (2018), which is incorporated herein by reference. In embodiments, the fluorinated polymer is an amorphous (non-crystalline) fluoropolymer (e.g., CYTOP® from Bellex), a crystalline fluoropolymer, or a fluoropolymer having both amorphous and crystalline domains.

In some embodiments, the solid support includes a hydrophilic polymer layer. In some embodiments, the hydrophilic polymer is a silane functionalized polymer. In some embodiments, the silane functionalized polymer is a silane functionalized polyethylene glycol (Si-PEG) polymer or a silane functionalized poly(acrylamide) (Si-PAm).

In embodiments, the passivated polymer layer or the amphiphilic polymer includes polymerized units of alkoxysilyl polymers. In embodiments, the passivated polymer layer includes polymerized units of alkoxysilyl polymers (e.g., TMSPM) and polymerized units of polyethylene glycol methacrylate (PEGMA. In embodiments, the amphiphilic copolymer includes polymerized units of alkoxysilyl polymers and polymerized units of polyethylene glycol methacrylate (PEGMA), or polyethylene glycol acrylate (PEGA). In embodiments, the amphiphilic copolymer includes polymerized units of 3-(trimethoxysilyl)propyl methacrylate (TMSPM), 3-(trimethoxysilyl)propyl methacrylate (TMSPA) and polymerized units of polyethylene glycol methacrylate (PEGMA), or polyethylene glycol acrylate (PEGA). In embodiments, the amphiphilic copolymer comprises polymerized units of 3-(trimethoxysilyl)propyl methacrylate (TMSPM) and polymerized units of polyethylene glycol methacrylate (PEGMA). In embodiments, the amphiphilic copolymer comprises polymerized units of 3-(trimethoxysilyl)propyl methacrylate (TMSPM), polymerized units of polyethylene glycol methacrylate (PEGMA) and polymerized units of hydroxyethylmethacrylate (HEMA). In embodiments, the amphiphilic copolymer comprises polymerized units of polyethylene glycol methacrylate (PEGMA) and polymerized units of hydroxyethylmethacrylate (HEMA).

In an aspect is provided a microfluidic device including a composition which includes a polymeric gel and/or plurality of particles as described herein. In embodiments, the microfluidic device includes a flow cell. In embodiments, the microfluidic device includes an imaging system or detection apparatus. Any of a variety of detection apparatus can be configured to detect the reaction vessel or solid support where reagents interact. Examples include luminescence detectors, surface plasmon resonance detectors and others known in the art. Exemplary systems having fluidic and detection components that can be readily modified for use in a system herein include, but are not limited to, those set forth in U.S. Pat. Nos. 8,241,573, 8,039,817; or US Pat. App. Pub. No. 2012/0270305 A1, each of which is incorporated herein by reference. In embodiments, the microfluidic device further includes one or more excitation lasers.

In embodiments, the microfluidic device is a nucleic acid sequencing device including: a stage configured to hold an array or solid support as described herein, including embodiments; an array or solid support as described herein, including embodiments; and a detector for obtaining sequencing data. In some embodiments, the detector is an imaging detector, such as a CCD, EMCCD, or s-CMOS detector. Nucleic acid sequencing devices utilize excitation beams to excite labeled nucleotides in the DNA containing sample to enable analysis of the base pairs present within the DNA. Many of the next-generation sequencing (NGS) technologies use a form of sequencing by synthesis (SBS), wherein modified nucleotides are used along with an enzyme to read the sequence of DNA templates in a controlled manner. In embodiments, sequencing includes a sequencing by synthesis event, where individual nucleotides are identified iteratively (e.g., incorporated and detected into a growing complementary strand), as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' reversible terminator may be removed to allow addition of the next successive nucleotide. In embodiments, the nucleic acid sequencing device utilizes the detection of four different nucleotides that comprise four different labels.

The term "nucleic acid sequencing device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, for the purpose of determining the nucleic acid sequence of a template polynucleotide. Nucleic acid sequencing devices may further include valves, pumps, and specialized functional coatings on interior walls. Nucleic acid sequencing devices may include a receiving unit, or platen, that orients the flow cell such that a maximal surface area of the flow cell is available to be exposed to an optical lens. Other nucleic acid sequencing devices include those provided by Singular Genomics™ such as the G4™ sequencing platform, Illumina™, Inc. (e.g., HiSeg™ MiSeg™, NextSeg™, or NovaSeg™ systems), Life Technologies™ (e.g., ABI PRISM™, or SOLiD™ systems), Pacific Biosciences (e.g., systems using SMRT™ Technology such as the Sequel™ or RS II™ systems), or Qiagen (e.g., Genereader™ system). Nucleic acid sequencing devices may further include fluidic reservoirs (e.g., bottles), valves, pressure sources, pumps, sensors, control systems, valves, pumps, and specialized functional coatings on interior walls. In embodiments, the device includes a plurality of a sequencing reagent reservoirs and a plurality of clustering reagent reservoirs. In embodiments, the clustering reagent reservoir includes amplification reagents (e.g., an aqueous buffer containing enzymes, salts, and nucleotides, denaturants, crowding agents, etc.) In embodiments, the reservoirs include sequencing reagents (such as an aqueous buffer containing enzymes, salts, and nucleotides); a wash solution (an aqueous buffer); a cleave solution (an aqueous buffer containing a cleaving agent, such as a reducing agent); or a cleaning solution (a dilute bleach solution, dilute NaOH solution, dilute HCl solution, dilute antibacterial solution, or water). The fluid of each of the reservoirs can vary. The fluid can be, for example, an aqueous solution which may contain buffers (e.g., saline-sodium citrate (SSC), ascorbic acid, tris(hydroxymethyl)aminomethane or "Tris"), aqueous salts (e.g., KCl or $(NH_4)_2SO_4$)), nucleotides, polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), chelating agents (e.g., EDTA), detergents, surfactants, crowding agents, or stabilizers (e.g., PEG, Tween, BSA). Non-limited examples of reservoirs include cartridges, pouches, vials, containers, and eppendorf tubes. In embodiments, the device is configured to perform fluorescent imaging. In embodiments, the device includes one or more light sources (e.g., one or more lasers). In embodiments, the illuminator or light source is a radiation source (i.e., an origin or generator of propagated electromagnetic energy) providing incident light to the sample. A radiation source can include an illumination source producing electromagnetic radiation in the ultraviolet (UV) range (about 200 to 390 nm), visible (VIS) range (about 390 to 770 nm), or infrared (IR) range (about 0.77 to 25 microns), or other range of the electromagnetic spectrum. In embodiments, the illuminator or light source is a lamp such as an arc lamp or quartz halogen lamp. In embodiments, the illuminator or light source is a coherent light source. In embodiments, the light source is a laser, LED (light emitting diode), a mercury or tungsten lamp, or a super-continuous diode. In embodiments, the light source provides excitation beams having a wavelength between 200 nm to 1500 nm. In embodiments, the laser provides excitation beams having a wavelength of 405 nm, 470 nm, 488 nm, 514 nm, 520 nm, 532 nm, 561 nm, 633 nm, 639 nm, 640 nm, 800 nm, 808 nm, 912 nm, 1024 nm, or 1500 nm. In embodiments, the illuminator or light source is a light-emitting diode (LED). The LED can be, for example, an Organic Light Emitting Diode (OLED), a Thin Film Electroluminescent Device (TFELD), or a Quantum dot based inorganic organic LED. The LED can include a phosphorescent OLED (PHOLED). In embodiments, the nucleic acid sequencing device includes an imaging system (e.g., an imaging system as described herein). The imaging system capable of exciting one or more of the identifiable labels (e.g., a fluorescent label) linked to a nucleotide and thereafter obtain image data for the identifiable labels. The image data (e.g., detection data) may be analyzed by another component within the device. The imaging system may include a system described herein and may include a fluorescence spectrophotometer including an objective lens and/or a solid-state imaging device. The solid-state imaging device may include a charge coupled device (CCD) and/or a complementary metal oxide semiconductor (CMOS). The system may also include circuitry and processors, including systems using microcontrollers, reduced instruction set computers (RISC), application specific integrated circuits (ASICs), field programmable gate array (FPGAs), logic circuits, and any other circuit or processor capable of executing functions described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. In embodiments, the device includes a thermal control assembly useful to control the temperature of the reagents.

The term "image" is used according to its ordinary meaning and refers to a representation of all or part of an object. The representation may be an optically detected reproduction. For example, an image can be obtained from fluorescent, luminescent, scatter, or absorption signals. The part of the object that is present in an image can be the surface or other xy plane of the object. Typically, an image is a 2 dimensional representation of a 3 dimensional object. An image may include signals at differing intensities (i.e., signal levels). An image can be provided in a computer readable format or medium. An image is derived from the collection of focus points of light rays coming from an object (e.g., the sample), which may be detected by any image sensor.

As used herein, the term "signal" is intended to include, for example, fluorescent, luminescent, scatter, or absorption impulse or electromagnetic wave transmitted or received. Signals can be detected in the ultraviolet (UV) range (about 200 to 390 nm), visible (VIS) range (about 391 to 770 nm), infrared (IR) range (about 0.771 to 25 microns), or other range of the electromagnetic spectrum. The term "signal level" refers to an amount or quantity of detected energy or coded information. For example, a signal may be quantified by its intensity, wavelength, energy, frequency, power, luminance, or a combination thereof. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

The term "xy coordinates" refers to information that specifies location, size, shape, and/or orientation in an xy plane. The information can be, for example, numerical coordinates in a Cartesian system. The coordinates can be provided relative to one or both of the x and y axes or can be provided relative to another location in the xy plane (e.g., a fiducial). The term "xy plane" refers to a 2 dimensional area defined by straight line axes x and y. When used in reference to a detecting apparatus and an object observed by the detector, the xy plane may be specified as being orthogonal to the direction of observation between the detector and object being detected.

In an aspect is a kit, wherein the kit includes the composition including the polymeric gel and/or plurality of particles as described herein. Generally, the kit includes one or more containers providing a composition and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, labeled nucleotides, and/or modified nucleotides), buffers, salts, and/or labels (e.g., fluorophores). In embodiments, the kit includes a solid support including any one of the compositions as described herein already attached to the solid support. In embodiments, the kit includes any one of the compositions as described herein with the plurality of particles already loaded into the layers. In embodiments, the kit includes any one of the compositions as described herein with the oligonucleotide moieties already attached to the layers.

In an aspect is provided a kit, wherein the kit includes the substrate as described herein. In embodiments, the kit includes components necessary to perform the methods as described herein. Generally, the kit includes one or more containers providing a composition and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, labeled nucleotides, and/or modified nucleotides), buffers, salts, and/or labels (e.g., fluorophores). In embodiments, the kit includes a substrate (e.g., a patterned substrate such as a flow cell), wherein the substrate includes a first plurality of immobilized oligonucleotides and a second plurality of immobilized oligonucleotides (e.g., the first plurality of immobilized oligonucleotides and the second plurality of immobilized oligonucleotides are each attached to the surface of the substrate). When the solid support includes an array of discrete sites of immobilized oligonucleotides, it may be referred to as an array. In embodiments, the substrate is in a container. The container may be a storage device or other readily usable vessel capable of storing and protecting the substrate. In embodiments the kit includes a substrate, at least 3 different sequencing primers, one or more polymerases, and one or more platform primers. In embodiments, the kit includes more than 3, more than 4, more than 5, more than 6, more than 7, more than 8, more than 9, or more than 10 different sequencing primers. In embodiments, the adapters are in separate reaction vessels or separate containers (e.g., individual buffered vials). In embodiments, the adapters are included in a single container (e.g., in a vial containing a buffered solution). In embodiments, the kit includes 3, 4, 5, 6, 7, 8, 9, 10 or more sequencing primers. In embodiments, all or a subset of sequencing primers are in separate containers. In embodiments, the sequencing primers are in a single container. In embodiments, a subset of the sequencing primers are in separate containers.

In embodiments, the kit includes a sequencing polymerase, and one or more amplification polymerases. In embodiments, the sequencing polymerase is capable of incorporating modified nucleotides. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol δ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g., Therminator γ, 9° N polymerase (exo-), Therminator II, Therminator III, or Therminator IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase or a thermostable phi29 mutant polymerase.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, bicine, tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid.

In embodiments, the kit includes one or more sequencing reaction mixtures. In embodiments, the kit includes one sequencing reaction mixture for each sequencing primer included in the kit (e.g., the kit includes 1, 2, 3, 4, 5, 6, 7, 8, 9, 10, 11, or 12 sequencing reaction mixtures). In embodiments, the kit includes a sequencing reaction mixture including a plurality of different sequencing primer species, wherein all but one of the sequencing primer species is terminated with one or more ddNTPs (e.g., ddCTP, ddATP, ddGTP, or ddTTP) at the 3' end. In embodiments, a cleavable site is present next to the one or more ddNTPs on the 3' end, wherein the cleavable site precedes the ddNTPs. In embodiments, the number of different sequencing primer species corresponds to the number of unique adapter sequences and sequencing primer regions present on the template polynucleotides on the surface. For example, if 4 unique sequencing primer binding sites are present on the template polynucleotides, then the sequencing reaction mixture would contain 1 sequencing primer with an extendable 3' end (e.g., a 3'-OH), and 3 sequencing primers with a cleavable site and one or more ddNTPs at the 3' end.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits. In embodiments, the kit includes, without limitation, nucleic acid primers, probes, adapters, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, digital storage medium, etc., on which the information has been recorded. Yet another means that may be present is a website address which may be used via the Internet to access the information at a removed site. Any convenient means may be present in the kits.

III. Methods

In an aspect is provided a method of amplifying a polynucleotide. In embodiments, the method includes contacting a composition or solid support as described herein with a polynucleotide, thereby hybridizing the polynucleotide to an oligonucleotide, and extending the oligonucleotide with a polymerase to generate an amplification product (e.g., an extended oligonucleotide including the complementary sequence of the polynucleotide, or a portion thereof).

In an aspect is provided a method of amplifying a template polynucleotide, the method including: (a) annealing a template polynucleotide to a first oligonucleotide of any one of the compositions described herein; (b) extending the first oligonucleotide with a polymerase to generate a complement template polynucleotide; (c) contacting the complement template polynucleotide and the template polynucleotide with a chemical denaturant thereby separating the complement template polynucleotide from the template polynucleotide; (d) removing the chemical denaturant and annealing the complement template polynucleotide to a second oligonucleotide on the composition; and (e) extending the second oligonucleotide with the polymerase to generate a template polynucleotide, thereby amplifying the template polynucleotide. In embodiments, the first oligonucleotide is complementary to a sequence of the template polynucleotide. In embodiments, the second oligonucleotide is complementary to a sequence of the complement template polynucleotide. In embodiments, the first oligonucleotide and the second oligonucleotide are attached (e.g., covalently or non-covalently attached) to the composition.

In an aspect is provided a method of amplifying a template polynucleotide, the method including: (a) hybridizing a template polynucleotide to a first oligonucleotide of any of the compositions or solid supports as described herein; (b) extending the first oligonucleotide with a polymerase to generate a complement template polynucleotide; (c) denaturing the complement template polynucleotide and the template polynucleotide, thereby separating the complement template polynucleotide from the template polynucleotide; (d) hybridizing the complement template polynucleotide to a second oligonucleotide on the composition; and (e) extending the second oligonucleotide with the polymerase to generate a template polynucleotide, thereby amplifying the template polynucleotide.

In an aspect is provided a method of amplifying a template polynucleotide, the method including: (i) contacting any one of the compositions described herein with an annealing solution, wherein one or more of the oligonucleotides is annealed to the template polynucleotide; (ii) contacting the composition with an extension solution; (iii) contacting the composition with a chemical denaturant; (iv) repeating steps (i)-(iii) to amplify the template polynucleotide. In embodiments, one or more of the oligonucleotides is attached (e.g., covalently or non-covalently attached) to the composition.

In embodiments, the polynucleotide is linear template polynucleotide. In embodiments, the linear template polynucleotide includes a genomic sequence of interest. In embodiments, the linear template polynucleotide includes one or more genomic sequences of interest. In embodiments, the linear template polynucleotide includes more than one genomic sequence of interest. In embodiments, the linear template polynucleotide includes cfDNA. In embodiments, the template polynucleotide includes one or more adapters. An adapter may include a platform primer sequence such as the P5 and P7 sequences, a sequencing primer binding sequence, and optionally one or two barcode/indexes. In embodiments, the template polynucleotide includes two adapters (e.g., an adapter at both the 5' and 3' end of the template polynucleotide.

In embodiments, prior to contacting the solid support the polynucleotides are circularized. In embodiments, circularizing the linear template polynucleotide includes joining the 5' end of the linear template polynucleotide directly to the 3' end of the linear template polynucleotide. In embodiments, circularizing the linear template polynucleotide includes extending the 3' end of the linear template polynucleotide and joining the extended 3' end to the 5' end of the linear template polynucleotide.

In embodiments, circularizing includes a ligation reaction. For example, linear polynucleotides are circularized in a non-template driven reaction with a circularizing ligase, such as CircLigase, Taq DNA Ligase, HiFi Taq DNA Ligase, T4 DNA ligase, or Ampligase® DNA Ligase. In embodiments, ligating includes enzymatic ligation including a ligation enzyme (e.g., Circligase enzyme, Taq DNA Ligase, HiFi Taq DNA Ligase, T4 ligase, PBCV-1 DNA Ligase (also known as SplintR ligase) or Ampligase DNA Ligase). Non-limiting examples of ligases include DNA ligases such as DNA Ligase I, DNA Ligase II, DNA Ligase III, DNA Ligase IV, T4 DNA ligase, T7 DNA ligase, T3 DNA Ligase, *E. coli* DNA Ligase, PBCV-1 DNA Ligase (also known as SplintR ligase) or a Taq DNA Ligase. In embodiments, the ligase enzyme includes a T4 DNA ligase, T4 RNA ligase 1, T4 RNA ligase 2, T3 DNA ligase or T7 DNA ligase. In embodiments, the enzymatic ligation is performed by a mixture of ligases. In embodiments, the ligation enzyme is selected from the group consisting of T4 DNA ligase, T4 RNA ligase 1, T4 RNA ligase 2, RtcB ligase, T3 DNA ligase, T7 DNA ligase, Taq DNA ligase, PBCV-1 DNA Ligase, a thermostable DNA ligase (e.g., 5'AppDNA/RNA ligase), an ATP dependent DNA ligase, an RNA-dependent DNA ligase (e.g., SplintR ligase), and combinations thereof. In embodiments, the two ends of the template polynucleotide are ligated together with the aid of a splint primer that is complementary with the two ends of the template polynucleotide. For example, a T4 ligation reaction may be carried out by combining a linear polynucleotide, ligation buffer, ATP, T4 DNA ligase, water, and incubating the mixture at between about 20° C. to about 45° C., for between about 5 minutes to about 30 minutes. In some embodiments, the T4 ligation reaction is incubated at 37° C. for 30 minutes. In some embodiments, the T4 ligation reaction is incubated at 45° C. for 30 minutes. In embodiments, the ligase reaction is stopped by adding Tris buffer with high EDTA and incubating for 1 minute. In embodiments, ligating includes chemical ligation (e.g., enzyme-free, click-mediated ligation). Reaction conditions and protocols for chemical ligation techniques that are compatible with nucleic acid amplification methods are known in the art, for example El-Sagheer, A. H., & Brown, T. (2012). *Accounts of chemical research,* 45(8), 1258-1267; Manuguerra I. et al. *Chem Commun* (Camb). 2018; 54(36):4529-4532; and Odeh, F., et al. (2019). *Molecules* (Basel, Switzerland), 25(1), 3, each of which is incorporated herein by reference in their entirety.

In embodiments, the polynucleotide is a circular polynucleotide. In embodiments, the circular template polynucleotide is about 100 to about 1000 nucleotides in length. In embodiments, the circular template polynucleotide is about 1000 to about 2000 nucleotides in length. In embodiments, the circular template polynucleotide is about 2000 to about 3000 nucleotides in length. In embodiments, the circular template polynucleotide is about 3000 to about 4000 nucleotides in length. In embodiments the circular template polynucleotide is about 4000 to about 5000 nucleotides in length. In embodiments, the circular template polynucleotide is about 100 to about 300 nucleotides in length. In embodiments, the circular template polynucleotide is about 300 to about 500 nucleotides in length. In embodiments, the circular template polynucleotide is about 500 to about 1000 nucleotides in length. In embodiments, the circular template polynucleotide is about 300 to about 600 nucleotides in length. The circular template polynucleotide molecules can vary length, such as about 100-300 nucleotides long, about 300-500 nucleotides long, or about 500-1000 nucleotides long. In embodiments, the circular template polynucleotide molecular is about 100-1000 nucleotides, about 1000-2000 nucleotides, about 2000-3000 nucleotides, about 3000-4000 nucleotides, about 4000-5000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides. In embodiments, the circular template polynucleotide molecule is about 150 nucleotides. In embodiments, the circular template polynucleotide is about 100-1000 nucleotides long. In embodiments, the circular template polynucleotide is about 1000-2000 nucleotides long. In embodiments, the circular template polynucleotide is about 2000-3000 nucleotides long. In embodiments, the circular template polynucleotide is about 3000-4000 nucleotides long. In embodiments, the circular template polynucleotide is about 4000-5000 nucleotides long. In embodiments, the circular template polynucleotide is about 100-300 nucleotides long. In embodiments, the circular template polynucleotide is about 300-500 nucleotides long. In embodiments, the circular template polynucleotide is about 500-1000 nucleotides long. In embodiments, the circular template polynucleotide molecule is about 100 nucleotides. In embodiments, the circular template polynucleotide molecule is about 300 nucleotides. In embodiments, the circular template polynucleotide molecule is about 500 nucleotides. In embodiments, the circular template polynucleotide molecule is about 1000 nucleotides. In embodiments, the circular template polynucleotide molecule is about 2000 nucleotides. In embodiments, the circular template polynucleotide molecule is about 3000 nucleotides. In embodiments, the circular template polynucleotide molecule is about 4000 nucleotides. In embodiments, the circular template polynucleotide molecule is about 5000 nucleotides.

In embodiments, the annealing is performed in the presence of an annealing solution. In embodiments, the annealing solution includes a buffered solution including salts (e.g., NaCl or KCl), a surfactant (e.g., Triton X-100 or Tween), and a chelator. In embodiments, the annealing solution has a pH of about 8.0, 8.2, 8.4, 8.6, 8.8, or 9.0. In embodiments, the annealing solution includes NaCl, Tris (e.g., pH 8.0), Triton X-100, and a chelator (e.g., EDTA). In embodiments, the annealing solution includes NaCl, Tris (e.g., pH 8.5), Triton X-100, and a chelator (e.g., EDTA). In embodiments, the annealing solution includes NaCl, Tris (e.g., pH 8.8), Triton X-100, and a chelator (e.g., EDTA).

In embodiments, the extending is performed in the presence of an extension solution. In embodiments, the extension solution includes a buffered solution including salts (e.g., NaCl or KCl), a surfactant (e.g., Triton X-100 or Tween-20), and a chelator. In embodiments, the extension solution includes nucleotides and a polymerase (e.g., a polymerase as described herein). In embodiments, the extension solution includes about 2, about 3, about 4, about 5, about 6, about 7, about 8, about 9, about 10, about 11, about 12, about 13, about 14, or about 15 mM $Mg^{2+}$. In embodiments, the extension solution includes a dNTP mixture including dATP, dCTP, dGTP and dTTP (for DNA amplification) or dATP, dCTP, dGTP and dUTP (for RNA amplification). In embodiments, the extension solution has a pH of about 8.0, 8.2, 8.4, 8.6, 8.8, or 9.0. In embodiments, the extension solution includes Tris-HCl (e.g., pH 8.0), salt (e.g., NaCl or KCl), MgSO4, a surfactant (e.g., Tween-20), dNTPs, BstLF, betaine, and/or DMSO. In embodiments, the extension solution includes bicine (e.g., pH 8.5), salt (e.g., NaCl or KCl), MgSO4, a surfactant (e.g., Tween-20), dNTPs, BstLF, betaine, and/or DMSO.

In embodiments, the method includes contacting the solid support with a chemical denaturant. In embodiments, the chemical denaturant includes formamide, ethylene glycol, or sodium hydroxide. In embodiments, the chemical denaturant includes formamide. In embodiments, the chemical denaturant is pure formamide. In embodiments, the chemical denaturant includes formamide, ethylene glycol, sodium hydroxide, or a mixture thereof. In embodiments, the denaturant is acetic acid, ethylene glycol, hydrochloric acid, nitric acid, formamide, guanidine, sodium salicylate, sodium hydroxide, dimethyl sulfoxide (DMSO), propylene glycol, urea, or a mixture thereof. In embodiments, the denaturant is an additive that lowers a DNA denaturation temperature. In embodiments, the denaturant is betaine, dimethyl sulfoxide (DMSO), ethylene glycol, formamide, glycerol, guanidine thiocyanate, 4-methylmorpholine 4-oxide (NMO), or a mixture thereof. In embodiments, the denaturant is betaine, dimethyl sulfoxide (DMSO), ethylene glycol, formamide, glycerol, guanidine thiocyanate, or 4-methylmorpholine 4-oxide (NMO). In embodiments, the chemical denaturant is sodium hydroxide.

In embodiments, the denaturant includes additives such as ethylene glycol, polyethylene glycol, 1,2-propanediol, dimethyl sulfoxide (DMSO), glycerol, formamide, 7-deaza-dGTP, acetamide, betaine, or tetramethylammonium chloride (TMAC). In embodiments, the denaturant is a buffered solution including about 0% to about 50% dimethyl sulfoxide (DMSO); about 0% to about 50% ethylene glycol; about 0% to about 20% formamide; or about 0 to about 3M betaine, or a mixture thereof. In embodiments, the denaturant is a buffered solution including about 50% to about 100% formamide. In embodiments, the denaturant is a buffered solution including about 100% formamide. In embodiments, the denaturant is a buffered solution including 100% formamide.

In embodiments, the denaturant, the extension solution, and/or the annealing solution includes one or more crowding agents. In embodiments, the crowding agent is poly(ethylene glycol) (e.g., PEG 200, PEG 600, PEG 800, PEG 2,050, PEG 4,600, PEG 6,000, PEG 8,000, PEG 10,000, PEG 20,000, or PEG 35,000). In embodiments, PEG is present in the denaturant at a concentration of 1% to 25%. In embodiments, PEG is present in the denaturant at a concentration of about 1%, about 5%, about 10%, about 15%, about 20%, or about 25%.

In embodiments of the methods provided herein, the contacting step is performed under non-hybridizing conditions. In embodiments of the methods provided herein, the contacting step is performed under non-hybridizing conditions initially, then the conditions are changed to hybridizing conditions. In embodiments of the methods provided herein, the contacting step is performed under hybridizing conditions initially, then the conditions are changed to non-hybridizing conditions. In general, contacting the sample under non-hybridizing conditions can facilitate distribution of target polynucleotides within a polymeric gel (e.g., a matrix of solid core particles) prior to subsequent steps (e.g. amplification). Examples of non-hybridizing conditions include but are not limited to low salt, high temperature, and/or presence of additives such as formamide. The precise nature of non-hybridizing conditions (e.g., the temperature, or the amounts of salt or formamide) will vary with factors such as the length, GC-content, or melting temperature (Tm) of primers (or the target-hybridizing portion thereof) present in the reaction. In embodiments, primers are designed to have Tm's within 15, 10, 5, 3 or fewer degrees of one another. In embodiments, non-hybridizing conditions comprises a temperature that is about or at least about 5, 10, 15, 20, or more degrees above the average Tm of primers in the reaction.

In embodiments, amplifying includes a plurality of cycles of strand denaturation, primer hybridization, and primer extension. In embodiments, amplifying includes thermally cycling between (i) about 80-95° C. for about 15-30 sec for denaturation, and (ii) about 50-75° C. for about 1 minute for annealing/extension of the primer. In embodiments, amplifying includes thermally cycling between about 72-80° C. for about 5 seconds to about 30 seconds for denaturation; and (ii) about 60-70° C. for about 30 to 90 seconds for annealing/extension of the primer. In embodiments, amplifying includes thermally cycling between (i) about 67-80° C. for about 5 seconds to about 30 seconds for denaturation; and (ii) about 60-70° C. for about 30 to 90 seconds for annealing/extension of the primer. In embodiments, amplifying includes thermally cycling between about 35° C. and about 65° C. In embodiments, amplifying includes thermally cycling between about 40° C. and about 60° C. In embodiments, amplifying includes thermally cycling between about 40° C. and about 58° C. In embodiments, amplifying includes thermally cycling between about 42° C. and about 62° C. In embodiments, amplifying includes thermally cycling between 35° C. and 65° C. In embodiments, amplifying includes thermally cycling between 40° C. and 60° C. In embodiments, amplifying includes thermally cycling between 40° C. and 58° C. In embodiments, amplifying includes thermally cycling between 42° C. and 62° C. In embodiments, amplifying includes thermally cycling about +/−45° C. In embodiments, amplifying includes thermally cycling about +/−40° C. In embodiments, amplifying includes thermally cycling about +/−35° C. In embodiments, amplifying includes thermally cycling about +/−30° C. In embodiments, amplifying includes thermally cycling about +/−25° C. In embodiments, amplifying includes thermally cycling about +/−20° C. In embodiments, amplifying includes thermally cycling about +/−15° C. In embodiments, amplifying includes thermally cycling about +/−10° C. In embodiments, amplifying includes thermally cycling about +/−5° C. In embodiments, amplifying includes thermally cycling about +/−2° C. In embodiments, the device as described herein is configured to perform amplifying of a target polynucleotide. Primer binding sequences usually have a length in the range of between 3 to 36 nucleotides, also 5 to 24 nucleotides, also from 12 to 36 nucleotides.

In embodiments, amplifying includes bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, emulsion PCR, or combinations thereof. In embodiments, amplifying includes bridge polymerase chain reaction (bPCR) amplification, solid-phase rolling circle amplification (RCA), or solid-phase exponential rolling circle amplification (eRCA).

In some embodiments, amplifying includes bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR on particles, or combinations thereof. In embodiments, amplifying includes a bridge polymerase chain reaction (bPCR) amplification. In embodiments, amplifying includes a thermal bridge polymerase chain reaction (t-bPCR) amplification. In embodiments, amplifying includes a chemical bridge polymerase chain reaction (c-bPCR) amplification. Chemical bridge polymerase chain reactions include fluidically cycling a denaturant (e.g., formamide) and maintaining the temperature within a narrow temperature range (e.g., +/−5° C.). In contrast, thermal bridge polymerase chain reactions include thermally cycling between high temperatures (e.g., 85° C.-95° C.) and low temperatures (e.g., 60° C.-70° C.). Thermal bridge polymerase chain reactions may also include a denaturant, typically at a much lower concentration than traditional chemical bridge polymerase chain reactions.

In embodiments, amplifying a template polynucleotide generates amplification products. In embodiments, amplifying includes a plurality of cycles of strand denaturation, primer hybridization, and primer extension. In embodiments, amplifying includes a plurality of cycles of strand denaturation, primer hybridization, and primer extension. Although each cycle will include each of these three events (denaturation, hybridization, and extension), events within a cycle may or may not be discrete. For example, each step may have different reagents and/or reaction conditions (e.g., temperatures). Alternatively, some steps may proceed without a change in reaction conditions. For example, extension may proceed under the same conditions (e.g., same temperature) as hybridization. After extension, the conditions are changed to start a new cycle with a new denaturation step, thereby amplifying the amplicons. Primer extension products from an earlier cycle may serve as templates for a later amplification cycle. In embodiments, the plurality of cycles is about 5 to about 50 cycles. In embodiments, the plurality of cycles is about 10 to about 45 cycles. In embodiments, the plurality of cycles is about 10 to about 20 cycles. In embodiments, the plurality of cycles is about 20 to about 30 cycles. In embodiments, the plurality of cycles is 10 to 45 cycles. In embodiments, the plurality of cycles is 10 to 20 cycles. In embodiments, the plurality of cycles is 20 to 30 cycles. In embodiments, the plurality of cycles is about 10 to about 45 cycles. In embodiments, the plurality of cycles is about 20 to about 30 cycles.

In embodiments, extending the amplification primer includes incubation with the strand-displacing polymerase in suitable conditions and for a suitable amount of time. In embodiments, the step of extending the amplification primer includes incubation with the strand-displacing polymerase (i) for about 10 seconds to about 30 minutes, and/or (ii) at a temperature of about 20° C. to about 50° C. In embodiments, incubation with the strand-displacing polymerase is for about 0.5 minutes to about 16 minutes. In embodiments, incubation with the strand-displacing polymerase is for about 0.5 minutes to about 10 minutes. In embodiments, incubation with the strand-displacing polymerase is for about 1 minutes to about 5 minutes. In embodiments, the method includes amplifying a template polynucleotide by extending an amplification primer with a strand-displacing polymerase for about 10 seconds to about 30 minutes. In embodiments, the method includes amplifying a template polynucleotide by extending an amplification primer with a strand-displacing polymerase for about 30 seconds to about 16 minutes. In embodiments, the method includes amplifying a template polynucleotide by extending an amplification primer with a strand-displacing polymerase for about 30 seconds to about 10 minutes. In embodiments, the method includes amplifying a template polynucleotide by extending an amplification primer with a strand-displacing polymerase for about 30 seconds to about 5 minutes. In embodiments, the method includes amplifying a template polynucleotide by extending an amplification primer with a strand-displacing polymerase for about 1 second to about 5 minutes. In embodiments, the method includes amplifying a template polynucleotide by extending an amplification primer with a strand-displacing polymerase for about 1 second to about 2 minutes. In embodiments, the strand-displacing polymerase is phi29 polymerase, phi29 mutant polymerase or a thermostable phi29 mutant polymerase. In embodiments, the strand-displacing polymerase is a thermostable strand-displacing (SD) DNA polymerase. In embodiments, the strand-displacing enzyme is an SD polymerase, Bst large fragment polymerase, or a phi29 polymerase or mutant thereof. In embodiments, the strand-displacing polymerase is phi29 polymerase, phi29 mutant polymerase or a thermostable phi29 mutant polymerase. A "phi polymerase" (or "Φ29 polymerase") is a DNA polymerase from the Φ29 phage or from one of the related phages that, like Φ29, contain a terminal protein used in the initiation of DNA replication.

In embodiments, incubation with the strand-displacing polymerase is at a temperature of about 35° C. to 42° C. In embodiments, incubation with the strand-displacing polymerase is at a temperature of about 37° C. to 40° C. In embodiments, incubation with the thermostable strand-displacing polymerase is at a temperature of about 40° C. to 80° C. In embodiments, the method includes amplifying a template polynucleotide by extending an amplification primer with a strand-displacing polymerase at a temperature of about 20° C. to about 50° C. In embodiments, the method includes amplifying a template polynucleotide by extending an amplification primer with a strand-displacing polymerase at a temperature of about 30° C. to about 50° C. In embodiments, the method includes amplifying a template polynucleotide by extending an amplification primer with a strand-displacing polymerase at a temperature of about 25° C. to about 45° C. In embodiments, the method includes amplifying a template polynucleotide by extending an amplification primer with a strand-displacing polymerase at a temperature of about 35° C. to about 45° C. In embodiments, the method includes amplifying a template polynucleotide by extending an amplification primer with a strand-displacing polymerase at a temperature of about 35° C. to about 42° C. In embodiments, the method includes amplifying a template polynucleotide by extending an amplification primer with a strand-displacing polymerase at a temperature of about 37° C. to about 40° C. An amplicon typically contains multiple, tandem copies of the circularized nucleic acid molecule of the corresponding sample nucleic acid. The number of copies can be varied by appropriate modification of the reaction conditions, such as varying the number of amplification cycles, using polymerases of varying processivity in the amplification reaction, or varying the length of time that the amplification reaction is run. In embodiments, the circular polynucleotide is copied about 5-50 times (i.e., the extension product includes about 5 to 50 complements of the circular polynucleotide). In embodiments, the circular polynucleotide is copied about 100-300 times (i.e., the extension product includes about 100 to 300 complements of the circular polynucleotide).

In embodiments, amplifying includes contacting the solid support (e.g., contacting the polymer layer(s)) with one or more reagents for amplifying the target polynucleotide. Examples of reagents include but are not limited to polymerase, buffer, and nucleotides (e.g., an amplification reaction mixture). In certain embodiments, the term "amplifying" refers to a method that includes a polymerase chain reaction (PCR). Conditions conducive to amplification (i.e., amplification conditions) are known and often comprise at least a suitable polymerase, a suitable template, a suitable primer or set of primers, suitable nucleotides (e.g., dNTPs), a suitable buffer, and application of suitable annealing, hybridization and/or extension times and temperatures. In embodiments, amplifying generates an amplicon. In embodiments, an amplicon contains multiple, tandem copies of the circularized nucleic acid molecule of the corresponding sample nucleic acid. The number of copies can be varied by appropriate modification of the amplification reaction including, for example, varying the number of amplification cycles run, using polymerases of varying processivity in the amplification reaction and/or varying the length of time that the amplification reaction is run, as well as modification of other conditions known in the art to influence amplification yield. Generally, the number of copies of a nucleic acid in an amplicon is at least 100, 200, 500, 1000, 2000, 3000, 4000, 5000, 6000, 7000, 8000, 9000 and 10,000 copies, and can be varied depending on the application. As disclosed herein, one form of an amplicon is as a nucleic acid "ball" localized to the particle and/or well of the array. The number of copies of the nucleic acid can therefore provide a desired size of a nucleic acid "ball" or a sufficient number of copies for subsequent analysis of the amplicon, e.g., sequencing.

In embodiments, the method further includes quantifying the target nucleic acid molecule or amplicons. Methods for quantifying a target polynucleotide or amplicon are known to one skilled in the art. For example, during amplification of the target nucleic acid, quantitative techniques such as real-time polymerase chain reaction (RT-PCR) can be used to quantify the copy number of target nucleic acid molecules present in the clonal object as discussed in Logan et al. Real-Time PCR: Current Technology and Applications, Caister Academic Press. (2009). RT-PCR follows the general principle of polymerase chain reaction, however inclusion of detection molecules, such as non-specific fluorescent dyes that intercalate with any double-stranded DNA, or sequence-specific DNA probes consisting of oligonucleotides that are labeled with a fluorescent reporter, which permits detection only after hybridization of the probe with its complementary DNA target, allows for the detection of nucleic acid formed during amplification. The rate of detectable molecules is proportional to the copy number of target nucleic acid molecules present in the clonal object. Furthermore, quantifying the target nucleic acid molecule or amplicons can be done following amplification using standard gel electrophoresis and/or Southern blot techniques, which are known in the art.

In embodiments, the method includes amplifying the circular polynucleotide by extending an amplification primer with a strand-displacing polymerase, wherein the primer extension generates an extension product including multiple complements of the circular polynucleotide. In embodiments, the method of amplifying includes an isothermal amplification method. In embodiments, the method of amplifying includes rolling circle amplification (RCA) or rolling circle transcription (RCT). In embodiments, the method of amplifying is rolling circle amplification (RCA). In embodiments, amplifying includes exponential rolling circle amplification (eRCA). Exponential RCA is similar to the linear process except that it uses a second primer (e.g., one or more immobilized oligonucleotide(s)) having a sequence that is identical to at least a portion of the circular template (Lizardi et al. Nat. Genet. 19:225 (1998)). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (Nilsson et al. Science 265(5181):208 5(1994)). Several suitable rolling circle amplification methods are known in the art. For example, RCA amplifies a circular polynucleotide (e.g., DNA) by polymerase extension of an amplification primer complementary to a portion of the template polynucleotide. This process generates copies of the circular polynucleotide template such that multiple complements of the template sequence arranged end to end in tandem are generated (i.e., a concatemer) locally preserved at the site of the circle formation. In embodiments, the amplifying occurs at isothermal conditions. In embodiments, the amplifying includes hybridization chain reaction (HCR). HCR uses a pair of complementary, kinetically trapped hairpin oligomers to propagate a chain reaction of hybridization events, as described in Dirks, R. M., & Pierce, N. A. (2004) PNAS USA, 101(43), 15275-15278, which is incorporated herein by reference for all purposes. In embodiments, the amplifying includes branched rolling circle amplification (BRCA); e.g., as described in Fan T, Mao Y, Sun Q, et al. Cancer Sci. 2018; 109:2897-2906, which is incorporated herein by reference in its entirety. In embodiments, the amplifying includes hyberbranched rolling circle amplification (HRCA). Hyperbranched RCA uses a second primer complementary to the first amplification product. This allows products to be replicated by a strand-displacement mechanism, which yields drastic amplification within an isothermal reaction (Lage et al., Genome Research 13:294-307 (2003), which is incorporated herein by reference in its entirety). In embodiments, amplifying includes polymerase extension of an amplification primer. In embodiments, the polymerase is T4, T7, Sequenase, Taq, Klenow, and Pol I DNA polymerases. SD polymerase, Bst large fragment polymerase, or a phi29 polymerase or mutant thereof.

In embodiments, amplifying the circular oligonucleotide includes incubation with a strand-displacing polymerase. In embodiments, amplifying includes incubation with a strand-displacing polymerase for about 10 seconds to about 30 minutes. In embodiments, amplifying includes incubation with a strand-displacing polymerase at a temperature of about 20° C. to about 50° C. In embodiments, incubation with the strand-displacing polymerase is at a temperature of about 35° C. to 42° C. In embodiments, the strand-displacing polymerase is phi29 polymerase, SD polymerase, Bst large fragment polymerase, phi29 mutant polymerase, or a thermostable phi29 mutant polymerase.

In embodiments, the extension product includes three or more copies of the target nucleic acid. In embodiments, the extension product includes at least three or more copies of the target nucleic acid. In embodiments, the extension product includes at least five or more copies of the target nucleic acid. In embodiments, the extension product includes at 5 to 10 copies of the target nucleic acid. In embodiments, the extension product includes 10 to 20 copies of the target nucleic acid. In embodiments, the extension product includes 20 to 50 copies of the target nucleic acid.

In embodiments, the method further includes sequencing the amplification products, and/or the complements thereof. In embodiments, sequencing includes hybridizing a sequencing primer to the sequencing primer binding sequence and generating a sequencing read. In embodiments, the method includes sequencing the first layer (e.g., determining the sequences of the target polynucleotides in the first layer), followed by sequencing the second layer. In embodiments, the target polynucleotides of the first layer include a first sequencing primer binding sequence, and the target polynucleotides in the third layer include a second sequencing primer binding sequence.

In an aspect is provided a method of sequencing a plurality of template polynucleotides, the method including: (a) hybridizing the plurality of template polynucleotides to the plurality of oligonucleotides of any one of the compositions described herein; (b) amplifying the template polynucleotides to produce discrete amplicon clusters, wherein (i) amplifying includes extension of the oligonucleotides along the template polynucleotides within each first layer and third layer, (ii) each amplicon cluster originates from amplification of a single template polynucleotide, and (iii) the amplicon clusters are arranged at a plurality of depths in each first layer and third layer; and (c) sequencing the amplicon clusters, wherein sequencing includes detecting sequences of signals within each first layer and third layer of the composition at a first depth and a second depth. In embodiments, the plurality of oligonucleotides is attached (e.g., covalently or non-covalently attached) to the composition. Sequencing includes, for example, detecting a sequence of signals within the particle. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the readout is accomplished by epifluorescence imaging. A variety of sequencing chemistries are available, non-limiting examples of which are described herein.

In embodiments, the first oligonucleotide is complementary to a sequence of a concatemer of complement template polynucleotides.

In embodiments, amplifying (and optionally sequencing) includes contacting compositions of the present disclosure with a polymerase. In embodiments of the methods provided herein, the polymeric gel and/or plurality of particles (e.g., MOF particles) are permeable to a polymerase for amplifying the target polynucleotide. In embodiments, the polymeric gel has a high permeability than the plurality of particles. In embodiments, the plurality of particles has a higher permeability than the polymeric gel. In embodiments, amplifying (and optionally sequencing) comprises contacting compositions of the present disclosure with a sequencing reaction mixture.

In embodiments of the methods provided herein, the sequencing step includes extending a sequencing primer to incorporate a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product of a target nucleic acid). In embodiments, the sequencing step may be accomplished by a sequencing-by-synthesis (SBS) process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. No. 8,178,360.

In embodiments of the methods provided herein, the detecting step includes imaging through each of the multiple polymeric gel layers at a resolution sufficient to distinguish one imaged plane from an adjacent imaged plane. In embodiments of the methods provided herein, the detecting step includes imaging through each of the multiple polymeric gel layers at a resolution sufficient to distinguish one particle from an adjacent particle. In embodiments of the methods provided herein, the detecting step includes imaging through each of the multiple polymeric gel layers at a resolution sufficient to distinguish one particle from another vertically adjacent particle. In embodiments, overlap of a signal of a cluster or particle in one layer appearing in adjacent layer, is computationally resolved, for example, by imaging software. In embodiments of the methods provided herein, the imaging is accomplished by confocal microscopy, multi-photon microscopy, or light sheet fluorescence microscopy (LSFM). In embodiments, the imaging is accomplished by confocal microscopy. In embodiments, the imaging is accomplished by multi-photon microscopy (e.g., two-photon excited fluorescence or two-photon-pumped microscopy). Unlike conventional single-photon emission, multi-photon microscopy can utilize much longer excitation wavelength up to the red or near-infrared spectral region. This lower energy excitation requirement enables the implementation of semiconductor diode lasers as pump sources to significantly enhance the photostability of materials. In embodiments, the imaging is accomplished by LSFM.

In embodiments of the methods provided herein, the amplifying step includes amplifying a target polynucleotide in two or more cores in the plurality of discrete particles, and the sequencing step includes sequencing an amplicon in two or more cores in the plurality of discrete particles. In embodiments, a plurality of different target polynucleotides are amplified and sequenced in a single collection of a plurality of cores. It will be appreciated that any of the amplification methodologies described herein or known in the art can be utilized with universal or target-specific primers to amplify the target polynucleotide. Suitable methods for amplification include, but are not limited to, the polymerase chain reaction (PCR), strand displacement amplification (SDA), transcription mediated amplification (TMA) and nucleic acid sequence based amplification (NASBA), for example, as described in U.S. Pat. No. 8,003,354, which is incorporated herein by reference in its entirety. The above amplification methods can be employed to amplify one or more nucleic acids of interest. Additional examples of amplification processes include, but are not limited to, bridge-PCR, recombinase polymerase amplification (RPA), loop-mediated isothermal amplification (LAMP), rolling circle amplification (RCA), strand displacement amplification, RCA with exponential strand displacement amplification. In embodiments, amplification comprises an isothermal amplification reaction. In embodiments, amplification comprises bridge amplification. In general, bridge amplification uses repeated steps of annealing of primers to templates, primer extension, and separation of extended primers from templates. Because primers are attached within the core, the extension products released upon separation from an initial template is also attached within the core. The 3' end of an amplification product is then permitted to anneal to a nearby reverse primer that is also attached within the core, forming a “bridge” structure. The reverse primer is then extended to produce a further template molecule that can form another bridge. In embodiments, forward and reverse primers hybridize to primer binding sites that are specific to a particular target nucleic acid. In embodiments, forward and reverse primers hybridize to primer binding sites that have been added to, and are common among, target polynucleotides. Adding a primer binding site to target nucleic acids can be accomplished by any suitable method, examples of which include the use of random primers having common 5' sequences and ligating adapter nucleotides that include the primer binding site.

In embodiments of the methods provided herein, each particle core further includes a silica, magnetic, or paramagnetic material, such as in the form of a bead or particle. For example, the core/shell layers may be formed around and encapsulating a supporting bead, for example, a silica, magnetic, or paramagnetic bead. In some embodiments, the composition includes a solid bead support (which itself may include a magnetic core and an encapsulating polymer layer), a functional core layer around the bead for primer attachment, and a shell polymer layer in which no amplification reactions take place. In embodiments, each core includes a silica particle. In embodiments, the core surrounds the silica particle.

In embodiments of the methods provided herein, sequencing includes extending a sequencing primer to incorporate a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product of a target nucleic acid). In embodiments, the sequencing step may be accomplished by a sequencing-by-synthesis (SBS) process.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. In embodiments, sequencing includes annealing and extending a sequencing primer to incorporate a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product produced by the amplification methods described herein). In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. No. 8,178,360.

In embodiments, the methods of sequencing a nucleic acid include a extending a polynucleotide by using a polymerase. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol δ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g., Therminator γ, 9° N polymerase (exo-), Therminator II, Therminator III, or Therminator IX). In embodiments, the DNA polymerase is a thermophilic nucleic acid polymerase. In embodiments, the DNA polymerase is a modified archaeal DNA polymerase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes). In embodiments, the polymerase is a bacterial DNA polymerase, eukaryotic DNA polymerase, archaeal DNA polymerase, viral DNA polymerase, or phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, €, η, ζ, λ, σ, μ, and k, as well as the Revl polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus* zilligi (Tzi) DNA polymerase, *Thermus thermophilus* (Tth) DNA polymerase, *Thermus flavus* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pemix* DNA polymerase; and the heterodimeric DNA polymerase DP1/DP2. In embodiments, the polymerase is 3PDX polymerase as disclosed in U.S. Pat. No. 8,703,461, the disclosure of which is incorporated herein by reference. In embodiments, the polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase.

In embodiments, sequencing is performed according to a "sequencing-by-binding" method (see, e.g., U.S. Pat. Pubs. US2017/0022553 and US2019/0048404, each of which is incorporated herein by reference in its entirety), which refers to a sequencing technique wherein specific binding of a polymerase and cognate nucleotide to a primed template nucleic acid molecule (e.g., blocked primed template nucleic acid molecule) is used for identifying the next correct nucleotide to be incorporated into the primer strand of the primed template nucleic acid molecule. The specific binding interaction need not result in chemical incorporation of the nucleotide into the primer. In some embodiments, the specific binding interaction can precede chemical incorporation of the nucleotide into the primer strand or can precede chemical incorporation of an analogous, next correct nucleotide into the primer. Thus, detection of the next correct nucleotide can take place without incorporation of the next correct nucleotide.

In embodiments, after sequencing a first polymer layer, the polynucleotides (e.g., the sequenced strand and/or amplification products) may be removed from the polymer layer prior to sequencing of another polymer layer. In embodiments, the first sequencing primer and the second sequencing primer are hybridized simultaneously to the first template polynucleotide and the second template polynucleotide, wherein one of the first sequencing primer or the second sequencing primer further includes a blocking element (e.g., a blocking element that prevents nucleotide incorporation with a polymerase). In embodiments, the blocking element is reversible. In embodiments, the blocking element is a ddNTP, a uracil, or a combination thereof (e.g., a ddNTP and a uracil). In embodiments the blocking element is a reversible terminator. In embodiments, once the sequencing read for the first template polynucleotide is generated, the blocking element of the second sequencing primer is removed and the sequencing read for the second template polynucleotide is generated (e.g., a uracil 5' of a ddNTP in the second sequencing primer is cleaved, the free 3' end is dephosphorylated with calf intestinal alkaline phosphatase (CIP) or T4 polynucleotide kinase (PNK), and a second sequencing process is initiated). In embodiments, once the sequencing read for the second template polynucleotide is generated, the blocking element of the first sequencing primer is removed and the sequencing read for the first template polynucleotide is generated (e.g., a uracil 5' of a ddNTP in the first sequencing primer is cleaved, the free 3' end is dephosphorylated with calf intestinal alkaline phosphatase (CIP) or T4 polynucleotide kinase (PNK), and a second sequencing process is initiated).

In embodiments, the sequencing primer is a sequence selected from the group consisting of SEQ ID NO:1 to SEQ ID NO:96, or a complement thereof.

TABLE 1

Multiplex Seeding Adapter Primer Sequences

| Internal Ref Name | Sequence (5'->3') | SEQ ID Num. |
|---|---|---|
| M1A | AACGCCAAACCTACGGCTTTACTTCCTGTGGCT | SEQ ID NO: 1 |
| M2A | TCTTGAGTCATTCGCAGGGCATGTGCCAGACCT | SEQ ID NO: 2 |
| M3A | TCGGCGTTGTCTGCTATCGTTCTTGGCACTCCT | SEQ ID NO: 3 |
| M4A | GGAGCAATAACCATAAGGCCGTTGACAAGCCCT | SEQ ID NO: 4 |
| M5A | GGCGTATTGCCTTGGTTCTGGCAGCCTCATTGT | SEQ ID NO: 5 |
| M1B | CAGCAGAGGGAACGATTTCAACTTCCTGTGGCT | SEQ ID NO: 6 |
| M2B | CTACTGCAAGGGTGTCTAGAATGTGCCAGACCT | SEQ ID NO: 7 |
| M3B | GACCGACTCGTGAAACGTAATCTTGGCACTCCT | SEQ ID NO: 8 |
| M4B | ACACATTCTTTGCGCCCAGAGTTGACAAGCCCT | SEQ ID NO: 9 |
| M5B | ATTTCATTCGACACCCGGTCGCAGCCTCATTGT | SEQ ID NO: 10 |
| M1A_R | TCGGTGTCCTTCATTTCGGCATCCAAACCGCAA | SEQ ID NO: 11 |
| M2A_R | TCCAGACCGTGTACGGGACGCTTACTGAGTTCT | SEQ ID NO: 12 |
| M3A_R | TCCTCACGGTTCTTGCTATCGTCTGTTGCGGCT | SEQ ID NO: 13 |
| M4A_R | TCCCGAACAGTTGCCGGAATACCAATAACGAGG | SEQ ID NO: 14 |
| M5A_R | TGTTACTCCGACGGTCTTGGTTCCGTTATGCGG | SEQ ID NO: 15 |
| M1B_R | TCGGTGTCCTTCAACTTTAGCAAGGGAGACGAC | SEQ ID NO: 16 |
| M2B_R | TCCAGACCGTGTAAGATCTGTGGGAACGTCATC | SEQ ID NO: 17 |
| M3B_R | TCCTCACGGTTCTAATGCAAAGTGCTCAGCCAG | SEQ ID NO: 18 |
| M4B_R | TCCCGAACAGTTGAGACCCGCGTTTCTTACACA | SEQ ID NO: 19 |
| M5B_R | TGTTACTCCGACGCTGGCCCACAGCTTACTTTA | SEQ ID NO: 20 |
| M1A_C | TTGCGGTTTGGATGCCGAAATGAAGGACACCGA | SEQ ID NO: 21 |
| M2A_C | AGAACTCAGTAAGCGTCCCGTACACGGTCTGGA | SEQ ID NO: 22 |
| M3A_C | AGCCGCAACAGACGATAGCAAGAACCGTGAGGA | SEQ ID NO: 23 |

TABLE 1-continued

Multiplex Seeding Adapter Primer Sequences

| Internal Ref Name | Sequence (5'->3') | SEQ ID Num. |
|---|---|---|
| M4A_C | CCTCGTTATTGGTATTCCGGCAACTGTTCGGGA | SEQ ID NO: 24 |
| M5A_C | CCGCATAACGGAACCAAGACCGTCGGAGTAACA | SEQ ID NO: 25 |
| M1B_C | GTCGTCTCCCTTGCTAAAGTTGAAGGACACCGA | SEQ ID NO: 26 |
| M2B_C | GATGACGTTCCCACAGATCTTACACGGTCTGGA | SEQ ID NO: 27 |
| M3B_C | CTGGCTGAGCACTTTGCATTAGAACCGTGAGGA | SEQ ID NO: 28 |
| M4B_C | TGTGTAAGAAACGCGGGTCTCAACTGTTCGGGA | SEQ ID NO: 29 |
| M5B_C | TAAAGTAAGCTGTGGGCCAGCGTCGGAGTAACA | SEQ ID NO: 30 |
| M1A_RC | AGCCACAGGAAGTAAAGCCGTAGGTTTGGCGTT | SEQ ID NO: 31 |
| M2A_RC | AGGTCTGGCACATGCCCTGCGAATGACTCAAGA | SEQ ID NO: 32 |
| M3A_RC | AGGAGTGCCAAGAACGATAGCAGACAACGCCGA | SEQ ID NO: 33 |
| M4A_RC | AGGGCTTGTCAACGGCCTTATGGTTATTGCTCC | SEQ ID NO: 34 |
| M5A_RC | ACAATGAGGCTGCCAGAACCAAGGCAATACGCC | SEQ ID NO: 35 |
| M1B_RC | AGCCACAGGAAGTTGAAATCGTTCCCTCTGCTG | SEQ ID NO: 36 |
| M2B_RC | AGGTCTGGCACATTCTAGACACCCTTGCAGTAG | SEQ ID NO: 37 |
| M3B_RC | AGGAGTGCCAAGATTACGTTTCACGAGTCGGTC | SEQ ID NO: 38 |
| M4B_RC | AGGGCTTGTCAACTCTGGGCGCAAAGAATGTGT | SEQ ID NO: 39 |
| M5B_RC | ACAATGAGGCTGCGACCGGGTGTCGAATGAAAT | SEQ ID NO: 40 |
| M6A | TGTTGCATCTCCACCCGGATTGAGCCTTCAGCT | SEQ ID NO: 41 |
| M7A | CACAACGGGAGCTGTGGAATTGGTTCACCTGGT | SEQ ID NO: 42 |
| M8A | TGGACTAAGACTCGTCCTCCAGCGGACCTAAGT | SEQ ID NO: 43 |
| M9A | GTATGATGGTGTTGCGGCTTCTCGCTTAACGCT | SEQ ID NO: 44 |
| M10A | TCTGAGTGCCAGTGACTTCACGCATTCGCTTGT | SEQ ID NO: 45 |
| M11A | TACGACACACTCGGGCTCTATGGGCTTCATGGT | SEQ ID NO: 46 |
| M12A | GTTTGAGTGAAGGCGGTCCAACCCTTAGTGCGT | SEQ ID NO: 47 |
| M6B | CTATAAGTTTGTCGTGCCCGTGAGCCTTCAGCT | SEQ ID NO: 48 |
| M7B | GGAGTGACACTGACTACGTTTGGTTCACCTGGT | SEQ ID NO: 49 |
| M8B | GTCAACGCCCTAGCAGACATAGCGGACCTAAGT | SEQ ID NO: 50 |
| M9B | CCAGAACCTATTGAGCCTGACTCGCTTAACGCT | SEQ ID NO: 51 |
| M10B | AGGTGTTCGTACAATGAGGCCGCATTCGCTTGT | SEQ ID NO: 52 |
| M11B | TGGTCAAGGGCAACTAATCCTGGGCTTCATGGT | SEQ ID NO: 53 |
| M12B | ACAATTACCCGTTTACCGGCACCCTTAGTGCGT | SEQ ID NO: 54 |
| M6A_R | TCGACTTCCGAGTTAGGCCCACCTCTACGTTGT | SEQ ID NO: 55 |
| M7A_R | TGGTCCACTTGGTTAAGGTGTCGAGGGCAACAC | SEQ ID NO: 56 |
| M8A_R | TGAATCCAGGCGACCTCCTGCTCAGAATCAGGT | SEQ ID NO: 57 |
| M9A_R | TCGCAATTCGCTCTTCGGCGTTGTGGTAGTATG | SEQ ID NO: 58 |
| M10A_R | TGTTCGCTTACGCACTTCAGTGACCGTGAGTCT | SEQ ID NO: 59 |
| M11A_R | TGGTACTTCGGGTATCTCGGGCTCACACAGCAT | SEQ ID NO: 60 |

TABLE 1-continued

| Multiplex Seeding Adapter Primer Sequences | | |
|---|---|---|
| Internal Ref Name | Sequence (5'->3') | SEQ ID Num. |
| M12A_R | TGCGTGATTCCCAACCTGGCGGAAGTGAGTTTG | SEQ ID NO: 61 |
| M6B_R | TCGACTTCCGAGTGCCCGTGCTGTTTGAATATC | SEQ ID NO: 62 |
| M7B_R | TGGTCCACTTGGTTTGCATCAGTCACAGTGAGG | SEQ ID NO: 63 |
| M8B_R | TGAATCCAGGCGATACAGACGATCCCGCAACTG | SEQ ID NO: 64 |
| M9B_R | TCGCAATTCGCTCAGTCCGAGTTATCCAAGACC | SEQ ID NO: 65 |
| M10B_R | TGTTCGCTTACGCCGGAGTAACATGCTTGTGGA | SEQ ID NO: 66 |
| M11B_R | TGGTACTTCGGGTCCTAATCAACGGGAACTGGT | SEQ ID NO: 67 |
| M12B_R | TGCGTGATTCCCACGGCCATTTGCCCATTAACA | SEQ ID NO: 68 |
| M6A_C | ACAACGTAGAGGTGGGCCTAACTCGGAAGTCGA | SEQ ID NO: 69 |
| M7A_C | GTGTTGCCCTCGACACCTTAACCAAGTGGACCA | SEQ ID NO: 70 |
| M8A_C | ACCTGATTCTGAGCAGGAGGTCGCCTGGATTCA | SEQ ID NO: 71 |
| M9A_C | CATACTACCACAACGCCGAAGAGCGAATTGCGA | SEQ ID NO: 72 |
| M10A_C | AGACTCACGGTCACTGAAGTGCGTAAGCGAACA | SEQ ID NO: 73 |
| M11A_C | ATGCTGTGTGAGCCCGAGATACCCGAAGTACCA | SEQ ID NO: 74 |
| M12A_C | CAAACTCACTTCCGCCAGGTTGGGAATCACGCA | SEQ ID NO: 75 |
| M6B_C | GATATTCAAACAGCACGGGCACTCGGAAGTCGA | SEQ ID NO: 76 |
| M7B_C | CCTCACTGTGACTGATGCAAACCAAGTGGACCA | SEQ ID NO: 77 |
| M8B_C | CAGTTGCGGGATCGTCTGTATCGCCTGGATTCA | SEQ ID NO: 78 |
| M9B_C | GGTCTTGGATAACTCGGACTGAGCGAATTGCGA | SEQ ID NO: 79 |
| M10B_C | TCCACAAGCATGTTACTCCGGCGTAAGCGAACA | SEQ ID NO: 80 |
| M11B_C | ACCAGTTCCCGTTGATTAGGACCCGAAGTACCA | SEQ ID NO: 81 |
| M12B_C | TGTTAATGGGCAAATGGCCGTGGGAATCACGCA | SEQ ID NO: 82 |
| M6A_RC | AGCTGAAGGCTCAATCCGGGTGGAGATGCAACA | SEQ ID NO: 83 |
| M7A_RC | ACCAGGTGAACCAATTCCACAGCTCCCGTTGTG | SEQ ID NO: 84 |
| M8A_RC | ACTTAGGTCCGCTGGAGGACGAGTCTTAGTCCA | SEQ ID NO: 85 |
| M9A_RC | AGCGTTAAGCGAGAAGCCGCAACACCATCATAC | SEQ ID NO: 86 |
| M10A_RC | ACAAGCGAATGCGTGAAGTCACTGGCACTCAGA | SEQ ID NO: 87 |
| M11A_RC | ACCATGAAGCCCATAGAGCCCGAGTGTGTCGTA | SEQ ID NO: 88 |
| M12A_RC | ACGCACTAAGGGTTGGACCGCCTTCACTCAAAC | SEQ ID NO: 89 |
| M6B_RC | AGCTGAAGGCTCACGGGCACGACAAACTTATAG | SEQ ID NO: 90 |
| M7B_RC | ACCAGGTGAACCAAACGTAGTCAGTGTCACTCC | SEQ ID NO: 91 |
| M8B_RC | ACTTAGGTCCGCTATGTCTGCTAGGGCGTTGAC | SEQ ID NO: 92 |
| M9B_RC | AGCGTTAAGCGAGTCAGGCTCAATAGGTTCTGG | SEQ ID NO: 93 |
| M10B_RC | ACAAGCGAATGCGGCCTCATTGTACGAACACCT | SEQ ID NO: 94 |
| M11B_RC | ACCATGAAGCCCAGGATTAGTTGCCCTTGACCA | SEQ ID NO: 95 |
| M12B_RC | ACGCACTAAGGGTGCCGGTAAACGGGTAATTGT | SEQ ID NO: 96 |

In embodiments of the methods provided herein, the detecting step includes imaging through each of the multiple polymeric gel layers at a resolution sufficient to distinguish one imaged plane from an adjacent imaged plane. In embodiments of the methods provided herein, the detecting step includes imaging through each of the multiple polymeric gel layers at a resolution sufficient to distinguish one particle from an adjacent particle. In embodiments of the methods provided herein, the detecting step includes imaging through each of the multiple polymeric gel layers at a resolution sufficient to distinguish one particle from another vertically adjacent particle. In embodiments, overlap of a signal of a cluster or particle in one layer appearing in adjacent layer, is computationally resolved, for example, by imaging software. In embodiments of the methods provided herein, the imaging is accomplished by confocal microscopy, multi-photon microscopy, or light sheet fluorescence microscopy (LSFM). In embodiments, the imaging is accomplished by confocal microscopy. In embodiments, the imaging is accomplished by multi-photon microscopy (e.g., two-photon excited fluorescence or two-photon-pumped microscopy). Unlike conventional single-photon emission, multi-photon microscopy can utilize much longer excitation wavelength up to the red or near-infrared spectral region. This lower energy excitation requirement enables the implementation of semiconductor diode lasers as pump sources to significantly enhance the photostability of materials. In embodiments, the imaging is accomplished by LSFM.

In embodiments, generating a sequencing read includes determining the identity of the nucleotides in the template polynucleotide (or complement thereof). In embodiments, a sequencing read includes determining the identity of a portion (e.g., 1, 2, 5, 10, 20, 50 nucleotides) of the total template polynucleotide.

In embodiments, the method includes generating about 500 million (M) to about $3\times10^{11}$ sequencing reads. In embodiments, the method includes generating about 500 million, about 750 million, about $1\times10^{9}$, about $2\times10^{9}$, about $3\times10^{9}$, about $4\times10^{9}$, about $5\times10^{9}$, about $6\times10^{9}$, about $7\times10^{9}$, about $8\times10^{9}$, about $9\times10^{9}$, about $1\times10^{10}$, about $2\times10^{10}$, about $3\times10^{10}$, about $4\times10^{10}$, about $5\times10^{10}$, about $6\times10^{10}$, about $7\times10^{10}$, about $8\times10^{10}$, about $9\times10^{10}$, about $1\times10^{11}$, about $2\times10^{11}$, or about $3\times10^{11}$ sequencing reads.

In embodiments, the method produces about 300 million sequencing reads, with greater than 99.9% accuracy. In embodiments, the method produces about 450 million sequencing reads, with greater than 99.9% accuracy. In embodiments, the method produces about 500 million sequencing reads, with greater than 99.9% accuracy. In embodiments, the method produces about 600 million sequencing reads, with greater than 99.9% accuracy. In embodiments the method produces about 750 million sequencing reads, with greater than 99.9% accuracy. In embodiments, the method produces about 1 billion sequencing reads, with greater than 99.9% accuracy. In embodiments, the method produces about 1, with greater than 99.9% accuracy. 2 billion sequencing reads, with greater than 99.9% accuracy. In embodiments, the method produces between about 300 million and 600 million sequencing reads, with greater than 99.9% accuracy. In embodiments, the method produces between about 600 million and 1 billion sequencing reads, with greater than 99.9% accuracy. In embodiments the method produces between about 1 billion and 1, with greater than 99.9% accuracy. 2 billion sequencing reads, with greater than 99.9% accuracy. In embodiments, the method produces more than 1, with greater than 99.9% accuracy. 2 billion sequencing reads, with greater than 99.9% accuracy. Base calling accuracy, measured by the Phred quality score (Q score), is the most common metric used to assess the accuracy of a sequencing platform. It indicates the probability that a given base is called incorrectly by the sequencer. For example, if the base calling algorithm assigns a Q score of 30 (Q30) to a base, this is equivalent to the probability of an incorrect base call 1 in 1000 times. This means that the base call accuracy (i.e., the probability of a correct base call) is 99.9%. In embodiments, the accuracy is 99.99%. In embodiments, the accuracy is 99.999%. In embodiments, the accuracy is 99.9999%. In embodiments, the accuracy is between about 99.9999% to 100%. In embodiments, the accuracy is between about 99.999% to 100%. In embodiments, the accuracy is between about 99.99% to 100%.

In embodiments, the method produces about 500 million sequencing reads. In embodiments, the method produces about 600 million sequencing reads. In embodiments, the method produces about 750 million sequencing reads. In embodiments, the method produces about 900 million sequencing reads. In embodiments, the method produces about 1 billion sequencing reads. In embodiments, the method produces about 1.2 billion sequencing reads. In embodiments, the method produces about 1.5 billion sequencing reads. In embodiments, the method produces about 1.8 billion sequencing reads. In embodiments, the method produces about 2 billion sequencing reads. In embodiments, the method produces about 2.2 billion sequencing reads. In embodiments, the method produces about 2.4 billion sequencing reads. In embodiments, the method produces between about 500 million and 750 million sequencing reads. In embodiments, the method produces between about 750 million and 1.2 billion sequencing reads. In embodiments, the method produces between about 1.2 billion and 2.4 billion sequencing reads. In embodiments, the method produces more than about 2.4 billion sequencing reads.

In embodiments of the methods provided herein, the target polynucleotides are at a concentration in the sample selected to produce amplicon clusters having a desired density. For example, the concentration of target polynucleotides is selected based on a calculation of (a) the average size of a cluster of amplicons that will result from amplification under selected conditions (e.g. a selected duration and number of extension steps), and (b) a desired separation between adjacent amplicon clusters in any one of the compositions described herein.

In embodiments of the methods provided herein, the amplicon clusters have a mean or median separation from one another of about 0.5-5 μm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 μm or a number or a range between any two of these values. The mean or median separation may be measured center-to-center (i.e., the center of one amplicon cluster to the center of a second amplicon cluster). In embodiments of the methods provided herein, the amplicon clusters have a mean or median separation (measured center-to-center) from one another of about 0.5-5 μm. The mean or median separation may be measured edge-to-edge (i.e., the edge of one amplicon cluster to the edge of a second amplicon cluster). In embodiments of the methods provided herein, the amplicon clusters have a mean or median separation (measured edge-to-edge) from one another of about 0.2-5 μm.

In embodiments of the methods provided herein, the amplicon clusters have a mean or median diameter of about 100-2000 nm, or about 200-1000 nm. In embodiments, the mean or median diameter is about 100-3000 nanometers, about 500-2500 nanometers, about 1000-2000 nanometers, or a number or a range between any two of these values. In embodiments, the mean or median diameter is about or at most about 100, 200, 300, 400, 500, 600, 700, 800, 900, 1000, 1100, 1200, 1300, 1400, 1500, 1600, 1700, 1800, 1900, 2000 nanometers or a number or a range between any two of these values.

In embodiments, the template polynucleotide includes genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA). In embodiments, the template polynucleotide includes double-stranded DNA. In embodiments, the method of forming the template polynucleotide includes ligating a hairpin adapter to an end of a linear polynucleotide. In embodiments, the method of forming the template polynucleotide includes ligating hairpin adapters to both ends of the linear polynucleotide. In embodiments, the method of forming the template polynucleotide includes ligating a Y-shaped adapter to an end of a linear polynucleotide. In embodiments, the method of forming the template polynucleotide includes ligating a Y-shaped adapter to both ends of a linear polynucleotide.

In some embodiments, a double stranded nucleic acid (i.e., a duplex) includes two complementary nucleic acid strands. In embodiments, a double stranded nucleic acid includes a first strand and a second strand which are complementary or substantially complementary to each other. A first strand of a double stranded nucleic acid is sometimes referred to herein as a forward strand and a second strand of the double stranded nucleic acid is sometime referred to herein as a reverse strand. In some embodiments, a double stranded nucleic acid includes two opposing ends. Accordingly, a double stranded nucleic acid often includes a first end and a second end. An end of a double stranded nucleic acid may include a 5'-overhang, a 3'-overhang or a blunt end. In some embodiments, one or both ends of a double stranded nucleic acid are blunt ends. In certain embodiments, one or both ends of a double stranded nucleic acid are manipulated to include a 5'-overhang, a 3'-overhang or a blunt end using a suitable method. In some embodiments, one or both ends of a double stranded nucleic acid are manipulated during library preparation such that one or both ends of the double stranded nucleic acid are configured for ligation to an adapter using a suitable method. For example, one or both ends of a double stranded nucleic acid may be digested by a restriction enzyme, polished, end-repaired, filled in, phosphorylated (e.g., by adding a 5'-phosphate), dT-tailed, dA-tailed, the like or a combination thereof.

In embodiments, the template polynucleotide is about 100 to 1,000 nucleotides in length. In embodiments, the template polynucleotide is about 350 nucleotides in length. In embodiments, the template polynucleotide is about 10, 20, 50, 100, 150, 200, 300, or 500 nucleotides in length. The template polynucleotide molecules can vary length, such as about 100-300 nucleotides long, about 300-500 nucleotides long, or about 500-1,000 nucleotides long. In embodiments, the template polynucleotide molecular is about 100-1,000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides. In embodiments, the template polynucleotide molecule is about 150 nucleotides. In embodiments, the template polynucleotide is about 100-1,000 nucleotides long. In embodiments, the template polynucleotide is about 100-300 nucleotides long. In embodiments, the template polynucleotide is about 300-500 nucleotides long. In embodiments, the template polynucleotide is about 500-1,000 nucleotides long. In embodiments, the template polynucleotide molecule is about 100 nucleotides. In embodiments, the template polynucleotide molecule is about 300 nucleotides. In embodiments, the template polynucleotide molecule is about 500 nucleotides. In embodiments, the template polynucleotide molecule is about 1,000 nucleotides.

In embodiments the template polynucleotide (e.g., genomic template DNA) is first treated to form single-stranded linear fragments (e.g., ranging in length from about 50 to about 600 nucleotides). Treatment typically entails fragmentation, such as by chemical fragmentation, enzymatic fragmentation, or mechanical fragmentation, followed by denaturation to produce single-stranded DNA fragments. In embodiments, the template polynucleotide includes an adapter. The adapter may have other functional elements including tagging sequences (i.e., a barcode), attachment sequences, palindromic sequences, restriction sites, sequencing primer binding sites, functionalization sequences, and the like. Barcodes can be of any of a variety of lengths. In embodiments, the primer includes a barcode that is 10-50, 20-30, or 4-12 nucleotides in length. In embodiments, the adapter includes a primer binding sequence that is complementary to at least a portion of a primer (e.g., a sequencing primer). Primer binding sites can be of any suitable length. In embodiments, a primer binding site is about or at least about 10, 15, 20, 25, 30, or more nucleotides in length. In embodiments, a primer binding site is 10-50, 15-30, or 20-25 nucleotides in length.

In embodiments of the methods provided herein, the contacting step is performed under non-hybridizing conditions. Examples of non-hybridizing conditions are described above, and include but are not limited to low salt, high temperature, or presence of additives such as formamide.

In embodiments of the methods provided herein, the polymeric gel includes water. In embodiments, the polymeric gel has a refractive index of about 1.2-1.6, 1.25-1.5, or 1.3-1.4 when hydrated. In embodiments, the polymeric gel has a refractive index of about 1.3 when hydrated. In embodiments, the polymeric gel, plurality of particles, or both have a refractive index of 1.2, 1.25, 1.3, 1.35, 1.4, 1.45, 1.5, 1.55, or 1.6 when hydrated.

The polymeric gel may include any of a variety of suitable polymers, and may be formed by the polymerization of any of a variety of suitable monomers or mixtures thereof. Examples of monomers (including functionalized monomers), mixtures of monomers (including mixtures of functionalized and non-functionalized monomers for spaced primer attachment), and polymers suitable for forming the polymer scaffold include, without limitation, any of the monomers, mixtures of monomers, and polymers described herein, such as with regard to the various compositions described herein. In embodiments of the methods provided herein, the polymeric gel is a hydrogel, non-limiting examples of which are described above. In embodiments, the polymeric gel is formed as in the plurality of cores described in connection with various core-shell compositions described herein, but lacks a shell polymer forming discrete cores. In embodiments, rather than utilizing a shell polymer to create a space between cores, spacing between amplicon clusters in a polymeric gel is controlled by factors such as the concentration of target polynucleotides in a sample applied to the scaffold polymer, and the size of the amplicon clusters produced under selected amplification conditions. By selecting conditions in which amplicon clusters have a desired spacing, clusters within the scaffold can be resolved during sequencing.

In embodiments of the methods provided herein, the amplifying step further includes contacting the polymeric gel with one or more reagents for amplifying the target polynucleotides. Examples of reagents include but are not limited to polymerase, buffer, and nucleotides.

In another aspect is provided a method of sequencing template polynucleotides, the method including: (a) hybridizing a first template polynucleotide to the first oligonucleotide of the solid support as described herein; and hybridizing a second template polynucleotide to the second oligonucleotide of the solid support; (b) amplifying the template polynucleotides to produce discrete amplicon clusters, and (c) sequencing the amplicon clusters, wherein sequencing includes detecting sequences of signals within each polymer layer. In embodiments, the method includes amplifying includes (i) extension of the oligonucleotides along the template polynucleotides within each polymer layer, (ii) each amplicon cluster originates from amplification of a single template polynucleotide, and (iii) the amplicon clusters are arranged at a plurality of depths in each polymer layer.

In embodiments of the methods provided herein, the sequencing step includes extending a sequencing primer to incorporate a detectable label that indicates the identity of a nucleotide in the target polynucleotide, detecting the detectable label, and repeating the extending and detecting of steps. In embodiments, the sequencing step may be accomplished by a sequencing-by-synthesis (SBS) process, non-limiting examples of which are described above.

In embodiments of the methods provided herein, detecting includes imaging through each of the multiple two-dimensional planes at a resolution sufficient to distinguish one imaged plane from an adjacent imaged plane. In embodiments, overlap of a signal of an amplicon cluster in one layer appearing in an adjacent layer is computationally resolved, for example, by imaging software. In embodiments of the methods provided herein, the imaging is accomplished by confocal microscopy, multi-photon microscopy, or light sheet fluorescence microscopy (LSFM). In embodiments, the imaging is accomplished by confocal microscopy. In embodiments, the imaging is accomplished by multi-photon microscopy. In embodiments, the imaging is accomplished by LSFM.

In embodiments of the methods provided herein, the polymeric gel is formed by a process that includes forming an emulsion of oil droplets in a hydrophilic continuous phase, polymerizing a plurality of monomers to form the polymeric gel, and removing the oil to form a plurality of interconnected pores in the polymeric gel. In embodiments, the hydrophilic continuous phase includes a plurality of monomers, non-limiting examples of which are described above.

In embodiments of the method provided herein, the polymeric gel is formed by a process that includes: reacting a plurality of monomers in a water/alcohol solution and maintaining the reaction temperature to less than 60° C.; increasing the reaction temperature to greater than or equal to 60° C.; mixing a plurality of crosslinkers (e.g., Bis-AAM) into the water/alcohol solution; and polymerizing the plurality of monomers and the plurality of crosslinkers to form the polymeric gel. In embodiments, the plurality of monomers include two types of monomers, including monomers with functional groups that react with polynucleotide primers, and monomers that do not contain functional groups.

In embodiments of the methods provided herein, the polymeric gel is formed by a process that includes functionalizing the polymeric gel with a plurality of first reactive groups, and contacting the functionalized polymeric gel with polynucleotide primers including a second reactive group. The first reactive group and second reactive group react to form a covalent bond. Examples of such covalent bond reactions include, but are not limited to, amine-modified polynucleotides reacting with epoxy or isothiocyanate groups on the polymeric gel, succinylated polynucleotides reacting with aminophenyl or aminopropyl functional groups on the polymer scaffold, dibenzocycloctyne-modified polynucleotides reacting with azide functional groups on the polymer scaffold (or vice versa), trans-cyclooctyne-modified polynucleotides reacting with tetrazine or methyl tetrazine groups on the polymeric gel (or vice versa), disulfide modified polynucleotides reacting with mercapto-functional groups on the polymer scaffold, amine-functionalized polynucleotides reacting with carboxylic acid groups on the polymeric gel via 1-ethyl-3-(3-dimethylaminopropyl)-carbodiimide hydrochloride (EDC) chemistry, thiol-modified polynucleotides attaching to a polymeric gel via a disulphide bond or maleimide linkage, alkyne-modified polynucleotides attaching to the polymeric gel via copper-catalyzed click reactions to azide functional groups on the polymeric gel, and acrydite-modified polynucleotides polymerizing with free acrylic acid monomers on the core to form polyacrylamide or reacting with thiol groups on the polymeric gel.

In embodiments, the sequencing method relies on the use of modified nucleotides that can act as reversible reaction terminators. Once the modified nucleotide has been incorporated into the growing polynucleotide chain complementary to the region of the template being sequenced there is no free 3'-OH group available to direct further sequence extension and therefore the polymerase cannot add further nucleotides. Once the identity of the base incorporated into the growing chain has been determined, the 3' reversible terminator may be removed to allow addition of the next successive nucleotide. These such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

The modified nucleotides may carry a label (e.g., a fluorescent label) to facilitate their detection. Each nucleotide type may carry a different fluorescent label. However, the detectable label need not be a fluorescent label. Any label can be used which allows the detection of an incorporated nucleotide. One method for detecting fluorescently labeled nucleotides includes using laser light of a wavelength specific for the labeled nucleotides, or the use of other suitable sources of illumination. The fluorescence from the label on the nucleotide may be detected (e.g., by a CCD camera or other suitable detection means).

In embodiments, detecting includes two-dimensional (2D) or three-dimensional (3D) fluorescent microscopy. Suitable imaging technologies are known in the art, as exemplified by Larsson et al., Nat. Methods (2010) 7:395-397 and associated supplemental materials, the entire content of which is incorporated by reference herein in its entirety. In embodiments of the methods provided herein, the imaging is accomplished by confocal microscopy. Confocal fluorescence microscopy involves scanning a focused laser beam across the sample and imaging the emission from the focal point through an appropriately-sized pinhole. This suppresses the unwanted fluorescence from sections at other depths in the sample. In embodiments, the imaging is accomplished by multi-photon microscopy (e.g., two-photon excited fluorescence or two-photon-pumped microscopy). Unlike conventional single-photon emission, multi-photon microscopy can utilize much longer excitation wavelength up to the red or near-infrared spectral region. This lower energy excitation requirement enables the implementation of semiconductor diode lasers as pump sources to significantly enhance the photostability of materials. Scanning a single focal point across the field of view is likely to be too slow for many sequencing applications. To speed up the image acquisition, an array of multiple focal points can be used. The emission from each of these focal points can be imaged onto a detector, and the time information from the scanning mirrors can be translated into image coordinates. Alternatively, the multiple focal points can be used just for the purpose of confining the fluorescence to a narrow axial section, and the emission can be imaged onto an imaging detector, such as a CCD, EMCCD, or s-CMOS detector. A scientific grade CMOS detector offers an optimal combination of sensitivity, readout speed, and low cost. One configuration used for confocal microscopy is spinning disk confocal microscopy. In 2-photon microscopy, the technique of using multiple focal points simultaneously to parallelize the readout has been called Multifocal Two-Photon Microscopy (MTPM). Several techniques for MTPM are available, with applications typically involving imaging in biological tissue. In embodiments of the methods provided herein, the imaging is accomplished by light sheet fluorescence microscopy (LSFM). In embodiments, detecting includes 3D structured illumination (3DSIM). In 3DSIM, patterned light is used for excitation, and fringes in the Moiré pattern generated by interference of the illumination pattern and the sample, are used to reconstruct the source of light in three dimensions. In order to illuminate the entire field, multiple spatial patterns are used to excite the same physical area, which are then digitally processed to reconstruct the final image. See York, Andrew G., et al. "Instant super-resolution imaging in live cells and embryos via analog image processing." Nature methods 10.11 (2013): 1122-1126 which is incorporated herein by reference. In embodiments, detecting includes selective planar illumination microscopy, light sheet microscopy, emission manipulation, pinhole confocal microscopy, aperture correlation confocal microscopy, volumetric reconstruction from slices, deconvolution microscopy, or aberration-corrected multifocus microscopy. In embodiments, detecting includes digital holographic microscopy (see for example Manoharan, V. N. Frontiers of Engineering: Reports on Leading-edge Engineering from the 2009 Symposium, 2010, 5-12, which is incorporated herein by reference). In embodiments, detecting includes confocal microscopy, light sheet microscopy, structured illumination microscopy, oblique plane microscopy, or multi-photon microscopy. Implementations of oblique plane microscopy are known, for example in Sapznik et al. eLife 2020; 9:e57681. Implementations of oblique plane microscopy are known, for example as described in Heintzmann and Huser, Chem. Rev. 2017, 117, 23, 13890-13908.

In embodiments, sequencing includes encoding the sequencing read into a codeword. Useful encoding schemes include those developed for telecommunications, coding theory and information theory such as those set forth in Hamming, Coding and Information Theory, 2nd Ed. Prentice Hall, Englewood Cliffs, N.J. (1986) and Moon TK. Error Correction Coding: Mathematical Methods and Algorithms. ed. 1st Wiley: 2005, each of which are incorporated herein by reference. A useful encoding scheme uses a Hamming code. A Hamming code can provide for signal (and therefore sequencing and barcode) distinction. In this scheme, signal states detected from a series of nucleotide incorporation and detection events (i.e., while sequencing the oligonucleotide barcode) can be represented as a series of the digits to form a codeword, the codeword having a length equivalent to the number incorporation/detection events. The digits can be binary (e.g. having a value of 1 for presence of signal and a value of 0 for absence of the signal) or digits can have a higher radix (e.g., a ternary digit having a value of 1 for fluorescence at a first wavelength, a value of 2 for fluorescence at a second wavelength, and a value of 0 for no fluorescence at those wavelengths, etc.). Barcode discrimination capabilities are provided when codewords can be quantified via Hamming distances between two codewords (i.e., barcode 1 having codeword 1, and barcode 2 having codeword 2, etc.).

In embodiments, the targets are detected within an optically resolved volume of a sample. In embodiments, the optically resolved volume has an axial resolution (i.e., depth, or z) that is greater than the lateral resolution (i.e., xy plane). In embodiments, the optically resolved volume has an axial resolution that is greater than twice the lateral resolution. In embodiments, the dimensions (i.e., the x, y, and z dimensions) of the optically resolved volume are about 0.5 μm×0.5 μm×0.5 μm; 1 μm×1 μm×1 μm; 2 μm×2 μm×2 μm; 0.5 μm×0.5 μm×1 μm; 0.5 μm×0.5 μm×2 μm; 2 μm×2 μm×1 μm; or 1 μm×1 μm×2 μm. In embodiments, the dimensions (i.e., the x, y, and z dimensions) of the optically resolved volume are about 1 μm×1 μm×2 μm; 1 μm×1 μm×3 μm; 1 μm×1 μm×4 μm; or about 1 μm×1 μm×5 μm. In embodiments, the dimensions (i.e., the x, y, and z dimensions) of the optically resolved volume are about 1 μm×1 μm×5 μm. In embodiments, the dimensions (i.e., the x, y, and z dimensions) of the optically resolved volume are about 1 μm×1 μm×6 μm. In embodiments, the dimensions (i.e., the x, y, and z dimensions) of the optically resolved volume are about 1 μm×1 μm×7 μm. In embodiments, the optically resolved volume is a cubic micron. In embodiments, the optically resolved volume has a lateral resolution from about 100 to 200 nanometers, from 200 to 300 nanometers, from 300 to 400 nanometers, from 400 to 500 nanometers, from 500 to 600 nanometers, or from 600 to 1000 nanometers. In embodiments, the optically resolved volume has a axial resolution from about 100 to 200 nanometers, from 200 to 300 nanometers, from 300 to 400 nanometers, from 400 to 500 nanometers, from 500 to 600 nanometers, or from 600 to 1000 nanometers. In embodiments, the optically resolved volume has a axial resolution from about 1 to 2 μm, from 2 to 3 μm, from 3 to 4 μm, from 4 to 5 μm, from 5 to 6 μm, or from 6 to 10 μm.

In embodiments, the methods of sequencing a nucleic acid include extending a complementary polynucleotide (e.g., a primer) that is hybridized to the nucleic acid by incorporating a first nucleotide. In embodiments, the method includes a buffer exchange or wash step. In embodiments, the methods of sequencing a nucleic acid include a sequencing solution. The sequencing solution includes (a) an adenine nucleotide, or analog thereof (b) (i) a thymine nucleotide, or analog thereof, or (ii) a uracil nucleotide, or analog thereof; (c) a cytosine nucleotide, or analog thereof and (d) a guanine nucleotide, or analog thereof.

EXAMPLES

Example 1. Multi-Layered 3D Scaffolds for Sequencing

Described herein are three-dimensional (3D) structures and scaffolds suitable for DNA sequencing. Maximizing the throughput of a standard flow cell remains a challenge. Adding an extra dimension (i.e., expanding in the z axis, or depth) to typical two-dimensional analyses represents a dramatic increase in the number of sequencing reactions that can be imaged in the same flow cell. For example, a flow cell containing a plurality of features (i.e., sites of target polynucleotides) separated at a spacing of 1 μm (on a square grid), a 1 cm×1 cm area would contain about $10^8$ features (or clusters of target polynucleotides). By comparison, if the same spacing was used in a 3D volume of only 0.1 mm depth, a 1 cm×1 cm×0.1 mm volume would contain 100 "layers" or $10^{10}$ features. The compositions described herein include 3D scaffolds of alternating layers of active polymer (i.e., polymer networks including reactive functional groups for covalently attaching oligonucleotide primers) and layers of inactive polymer (e.g., polymer networks lacking oligonucleotide primers) (see, e.g., FIG. 1). By providing multiple spatially and optically separated layers for amplification and sequencing reactions to occur, an enormous improvement in sequencing throughput may be obtained compared to traditional single-plane sequencing platforms and devices.

Figure 2:
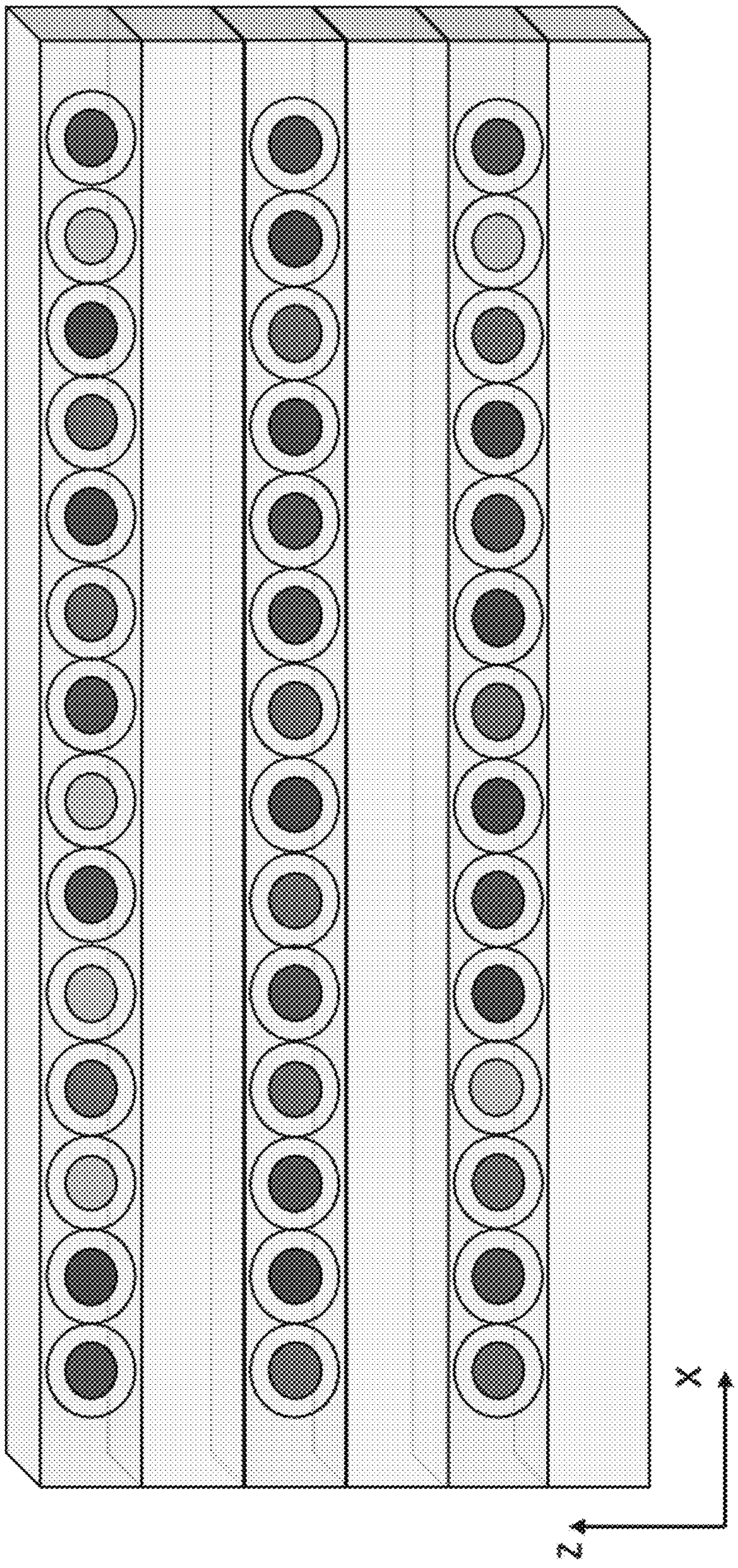
FIG. 2 illustrates one embodiment of a spatially heterogeneous polymer scaffold as described herein. In this embodiment, the polymer scaffold includes active layers that include a plurality of particles that include one or more bioconjugate reactive moieties (e.g., azido groups) and/or immobilized primers. For particles having one or more bioconjugate reactive moieties, oligonucleotides including a complementary bioconjugate reactive moiety (e.g., a 5'-DBCO or a 5'-alkyne oligonucleotide) react and become immobilized on the particles. The immobilized oligonucleotides include nucleic acid sequences complementary to template nucleic acids (e.g., a universal adapter sequence-containing library). Alternatively, the particles can include immobilized oligonucleotides capable of hybridizing to template nucleic acids (e.g., a universal adapter sequence-containing library). Following template hybridization, under suitable amplification conditions, colonies of template nucleic acids are localized on the particles. Separating the active particle layers are passive layers (e.g., inactive layers that do not include particles containing immobilized primers and/or bioconjugate reactive moieties capable of immobilizing an oligonucleotide). As illustrated, the uniform active layers are separated from one another by a passive layer. The active particle layers may facilitate amplification reactions at each immobilized oligonucleotide primer to form spatially separated amplicon clusters, located at or around each particle.

The active layer may include a plurality of particles, wherein the particles include immobilized oligonucleotides. As illustrated in FIG. 2, uniform active layers may include, in embodiments, particles that include bioconjugate reactive moieties (e.g., azido groups) and/or immobilized primers. For example, in embodiments, the plurality of particles include a plurality of cores surrounded by a shell polymer. In embodiments, each core of the plurality of cores is surrounded by a shell polymer, and the core is a solid core or a metal organic framework (MOF). In embodiments, a passive layer (i.e., a layer that does not include oligonucleotide moieties) includes a plurality of shell polymers. In embodiments, the plurality of shell polymers in the passive layer separates two polymeric gel layers, each polymeric gel layer including a plurality of cores surround by a shell polymer including attached oligonucleotide moieties. In embodiments, one or more core polynucleotide primer(s) is attached to the core and a target nucleic acid is hybridized to the core primer. In embodiments, at least two different primers are attached to the core (e.g., a forward and a reverse primer). In embodiments, the shell polymer is formed by polymerized units of shell monomers, and the shell polymer is not attached to a polynucleotide primer. The core itself may be a solid support particle, such as a glass, ceramic, metal, silica, magnetic, or paramagnetic particle (e.g., a 500 nm silica nanoparticle). Solid support particles may be composed of any appropriate material. In embodiments, the support particle is an amorphous solid. In embodiments, the support particle is a crystalline solid. For example, solid support particles may include appropriate metals and metal oxides thereof (a metal particle core), carbon (an organic particle core) silica and oxides thereof (a silica particle core), boron and oxides thereof (a boron particle core), or a metal organic framework (MOF).

In embodiments, the multi-layered scaffolds include multiple distinct layers/planes of clusters, separated by blank layers. For example, in embodiments, a layer of particles is deposited within a hydrogel. The thickness of the layer is controlled to be about 1 particle diameter, or possibly a little greater. The density of the particles would be near close-packed. Next, the particle layer is fixed by cross-linking (e.g., crosslinking via UV, heat, or chemical crosslinking agents). Next, a "blank" layer of hydrogel (i.e., does not contain immobilized oligonucleotides or functional groups capable of immobilizing oligonucleotides) is deposited on top of the particles. In embodiments, the thickness of the blank layer could be about 1-2× of the particle diameter. Next, the blank layer is fixed by cross-linking (e.g., cross-linking via UV, heat, or chemical crosslinking agents). This process may be repeated to produce multiple layers, e.g., 5-10 layers, thereby forming contiguous layered units, wherein each contiguous layered unit includes a first layer and a second layer including attached oligonucleotide primers (i.e., the active layers), and a second layer that does not include attached oligonucleotide primers (i.e., a passive layer).

The use of particles, even without a shell, also offers the possibility for clustering amplification reactions to be carried out "offline," in other words, before they are arranged into the 3D or 2D structures. The clustering reactions may be carried out in a micro-emulsion, digitally formed droplets, or in a bulk solution under conditions that favor localized amplification.

In embodiments, the active layer does not include particles. In embodiments, the active layer includes immobilized oligonucleotides covalently attached to the polymer scaffold. For example, in embodiments, the active layer includes a random distribution of bioconjugate reactive moieties (e.g., azido groups) or immobilized reactive polymers confined to an active layer and separated from other active layers by a passive layer (e.g., an inactive layer). The active layers include covalently attached primers (e.g., primers attached via bioconjugate reactive moieties), while the passive layers would not have any primers available for template capture and amplification.

In embodiments, the regions (i.e., the one or more inactive layers and the one or more active layers) have a thickness of between about 0.50 μm to about 2.5 μm. The thickness of a combined active layer and inactive layer "sandwich" is up to about 1.5 μm to about 5 μm. In embodiments, the thickness of each active layer is about 2.25 μm and the thickness of each inactive layer is about 3 μm. In embodiments, the thickness of each active layer is about 1.5 μm and the thickness of each inactive layer is about 2 μm. In embodiments, the thickness of each active layer is about 1.05 μm and the thickness of each inactive layer is about 1.5 μm. The choice of the relative thickness of the active layer to the inactive layer is based on suitable parameters for fluorescent intensity (which increases with the size of the active layer), and acceptable cross-talk between adjacent active layers (cross-talk is reduced with a thicker inactive layer). In some examples, the thickness of the inactive layer is approximately the same as the thickness of the active layer. In some examples, the thickness of the inactive layer(s) is about 50% to about 95% of the thickness of the active layer(s). The inactive layer may be engineered (e.g., by altering the ratio of starting materials or duration of the reaction) to have a specific thickness. Thickness of a layer, in embodiments, is defined as the distance from the lowest Z-coordinate of the layer, which contacts (interfaces) with either a solid support or another layer, to the highest Z-coordinate of the layer (the surface of the layer that interfaces the next layer and/or the environment), which interfaces with the external environment (e.g., external medium). In embodiments, the thickness of a layer may be directly correlated to the thickness (e.g., the diameter) of the particles included in the layer. Layer thickness may be approximately uniform (e.g., no more than 25% variation, 20% variation, 15% variation, 10% variation, 5% variation, 4% variation, 3% variation, 2% variation or 1% variation) across the entirety of the active layer(s) and/or the inactive layer(s). Alternatively, the layer thickness may be non-uniform. In embodiments, the layer thickness is determined by transmission electron microscopy (TEM) or scanning electron microscopy (SEM).

In embodiments, the active layers are not immediately adjacent to each other (i.e., the segment containing amplicon clusters do not physically touch). Each active layer is separated from the nearest active layer by an inactive layer, which prevents cross-interaction among active layers, and makes it easier to create conditions under which unique monoclonal clusters are formed throughout each active layer, resulting in a high signal to noise ratio, for example, during sequencing processes. For example, the free volume and permeability of the 3D matrix permits carrying out amplification reactions with techniques such as bridge-PCR, RPA, LAMP, RCA with exponential strand displacement amplification, and other isothermal amplification reactions. The primers for these reactions are immobilized in the active layer(s), and the amplification products remain confined to the active layer(s) and physically separated from other active layer(s). The clustering amplification reactions may be carried out simultaneously across all active layers, wherein each active layer is separated from every other active layer in the scaffold by an inactive layer (see, FIG. 1). In embodiments, clustering amplification reactions may be carried out in individual active layers prior to assembly into a multi-layered scaffold, wherein each active layer is separated from every other active layer in the multi-layered scaffold by an inactive layer.

The three-dimensional (3D) structures described herein form a polymeric network and have a refractive index similar to water when hydrated. The mesh size of the network is tunable and suitable for reagent diffusion to allow amplification and sequencing controlled by amplification kinetics. One type of scaffold structure has multiple distinct layers or sections of polynucleotide clusters, including oligonucleotide primers for generating DNA clusters. The regions containing polynucleotides are separated by a passive polymer that acts as a spacer between neighboring active layer(s). The passive polymer may be the same polymer composition, or the passive polymer layer may be a different polymer composition than the regions containing polynucleotides. Notably, the passive polymer layer does not contain functional groups for binding to DNA primers (e.g., azide moieties) nor does the passive polymer layer contain immobilized polynucleotides. In embodiments, both the active and inactive polymer layers are permeable and facilitate the diffusion of reagents, including enzymes and template polynucleotides, while the active polymer layers allow for the immobilization of the template polynucleotides to the DNA primers by contacting and amplifying the template polynucleotides. The choice of functional group concentration in the active layer(s) is selected based on parameters of a given cluster amplification reaction and fluorescence intensity to be detected. Having a non-fluorescent inactive layer allows for better resolution and less cross-talk between neighboring layers, or features within the active layer.

To facilitate imaging through many layers of the scaffold, the layers themselves have very low light scattering. For example, in embodiments, the layers have an index of refraction that is close to water (about 1.33). The scaffold material may include hydrogels, and other polymers that hold a high degree of water content. Alternatively, the scaffold material may include denser polymers with interconnected pores, for example, hydrogels prepared by inverse high internal phase emulsion polymerization (i-HIPE) copolymerization of glycerol monomethacrylate (GMMA), 2-hydroxy ethyl methacrylate (HEMA), and glycerol dimethacrylate, as described in Nalawade A C et al. J. Mater. Chem. B. 2016; 4: 450-460, which is incorporated herein by reference in its entirety. The scaffold material can be functionalized with reactive groups that can be used for coupling polynucleotide primers. Hydrogels also allow for efficient movement of small molecules, including nucleotides, through the scaffold. Depending on the design of the polymer network (including degree of cross-linking), it can be made permeable to large molecules such as enzymes and DNA.

In embodiments, the multi-layered scaffolds are prepared by spin-coating each active layer and inactive layer composition onto a solid support in an alternating fashion until the target number of layers have been deposited.

In embodiments, the scaffold includes 1 active layer and 1 inactive layer. In embodiments, the scaffold includes 2 active layers and 1 inactive layer. In other embodiments, the scaffold includes between 2 and 5 active layers and between 2 and 5 inactive layers. In embodiments, the scaffold includes between 1 to 10 active layers and between 1 to 10 inactive layers. In embodiments, the scaffold includes 1, 2, 3, 4, 5, 6, 7, 8, 9, 10, or more active layers and 1, 2, 3, 4, 5, 6, 7, 8, 9, 10, or more inactive layers. An example of a multi-layer 3D scaffold is shown in FIG. 3. The active layer composition can be a homo- or copolymer of monomers including monomers with active functional end groups. The inactive layer composition can be the same homo- or copolymer of monomers as the active layer, but without monomers with active functional end groups. In other examples, the inactive layer is a different material than the active layer, e.g., plastic, silica, a different homo- or copolymer of monomers, etc. Both the active layer and inactive layer composition should result in minimal autofluorescence and background signal. As described herein, each set of two active layers separated by an inactive polymer layer may be referred to as a contiguous layered unit, as denoted by the brackets on the right-hand side of the scaffold illustrated in FIG. 3. In this illustration, the multi-layered, spatially heterogeneous polymer scaffold has five contiguous layered units, each separated by at least one inactive polymer layer.

Monomers for preparation of layers can be hydrophilic or a combination of hydrophilic and hydrophobic acrylate or methacrylate monomers but not limited to these types of monomers. The layer thickness can be controlled by solvent composition, monomer and stabilizer concentrations, and deposition rates. For close packing of active layers, the thickness and uniformity of the inactive layers is very important. The permeability of reactants such as the ones mentioned above through the layers can be tuned by the ratio between monomers and cross-linker. The first layer deposited on a solid support (e.g., a flow cell, a slide, or a multiwell plate) can be decorated with active functional groups that can be reacted with the surface of the substrate to immobilize the layer to the support.

It may be advantageous to first flow in the DNA templates under conditions that are non-hybridizing (e.g., low salt, high temperature, or presence of additives such as formamide), to facilitate a uniform distribution of the templates throughout the 3D volume. A desirable characteristic of the 3D matrix is minimal non-specific binding of DNA template molecules to the matrix, either via electrostatic, van der Waals or hydrophobic interactions. The concentration of the templates is selected to give the desired density of clusters in the 3D volume. Then, clustering reactions start from each of the templates present in the 3D volume. Clustering reactions proceed for a period of time sufficient to reach the desired cluster size, e.g., a diameter of about 0.2 μm to about 1 μm. Due to the lack of covalently attached DNA primers in the inactive layer(s), any template polynucleotides that are present in the inactive layer(s) during the clustering reaction will not be amplified, and may be washed away during intervening steps.

Example 2. Imaging

During sequencing by synthesis (SBS), reversibly-terminated nucleotides carrying fluorescent dyes are incorporated into a growing strand, complementary to the target strand being sequenced. The nucleotides are labeled with up to four (4) unique fluorescent dyes.

In embodiments, sequencing is performed according to a "sequencing-by-binding" method (see, e.g., U.S. Pat. Pubs. US2017/0022553 and US2019/0048404, each of which is incorporated herein by reference in its entirety), which refers to a sequencing technique wherein specific binding of a polymerase and cognate nucleotide to a primed template nucleic acid molecule (e.g., blocked primed template nucleic acid molecule) is used for identifying the next correct nucleotide to be incorporated into the primer strand of the primed template nucleic acid molecule. The specific binding interaction need not result in chemical incorporation of the nucleotide into the primer. In some embodiments, the specific binding interaction can precede chemical incorporation of the nucleotide into the primer strand or can precede chemical incorporation of an analogous, next correct nucleotide into the primer. Thus, detection of the next correct nucleotide can take place without incorporation of the next correct nucleotide.

The readout of, for example an SBS process, is typically accomplished by epifluorescence imaging. In 3D flow cells, standard epifluorescence as applied in 2D imaging applications would be problematic, as there would be poor resolution along the axial direction. Two approaches can be used to improve the axial resolution: confocal microscopy and multi-photon microscopy.

Confocal fluorescence microscopy involves scanning a focused laser beam across the sample, and imaging the emission from the focal point through an appropriately-sized pinhole. This suppresses the unwanted fluorescence from sections at other depths in the sample. Confocal microscopy is a technique where one or more pinholes are positioned at the confocal plane of the lens, blocking out-of-focus light from reaching the detector. The focal plane of the lens is systematically shifted through the third dimension, enabling volumetric imaging. See Wilson, Tony. "Confocal microscopy." Academic Press: London, etc. 426 (1990): 1-64 hereby incorporated by reference in its entirety.

While confocal microscopy provides much better axial resolution than standard epifluorescence, it still encounters the issue of excessive photo-bleaching and photo-damage, as all axial sections are illuminated at all times. One solution to these issues is to use multi-photon excitation, where the optical excitation is limited to the region of high intensity in the focal volume. Multi-photon microscopy solves both of the challenges involved in imaging a 3D flow cell: axial resolution and reduced photo-damage. The excitation only occurs in the focal plane, where the intensity is high enough for 2 photons to be absorbed simultaneously. Additional methods for volumetric imaging that may be applied to the polymer scaffolds described herein may be found in, e.g., U.S. Pat. Pub. 2021/0363579, which is incorporated herein by reference in its entirety.

Figure 4:
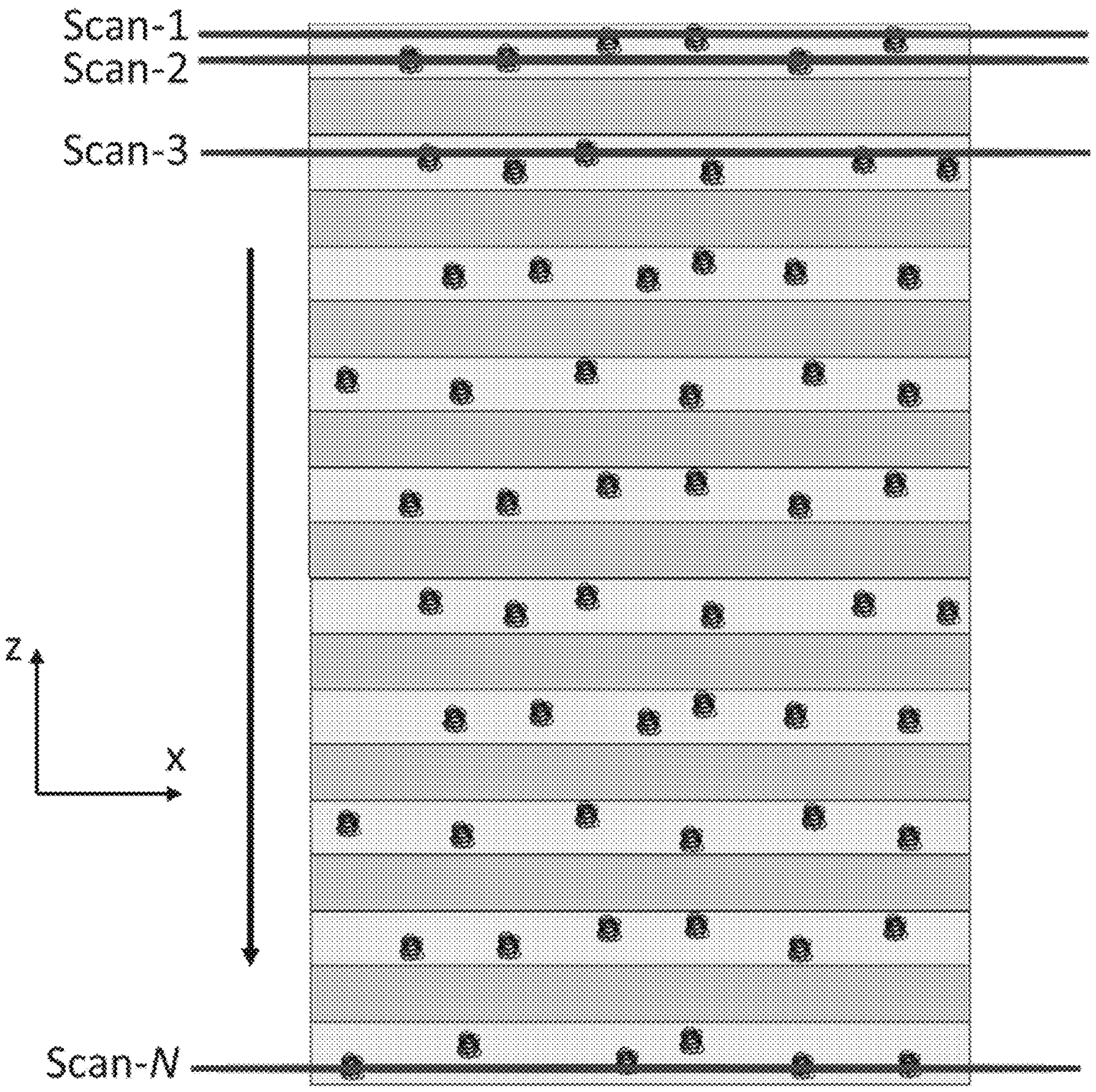
FIG. 4 illustrates multi-dimensional detection for polymer scaffolds including multiple active layers and inactive layers. Detection of the illustrated amplicon clusters in the active layers can be performed according to the methods described herein. During a sequencing process (e.g., SBS), optical sectioning using, for example, confocal microscopy or multi-photo excitation microscopy, is used to image a first active layer at a first depth (i.e., Scan-1) and detect one or more incorporated labeled nucleotides representative of one or more sequenced bases, independent of the labeled nucleotides present in all other active layers. Once the first layer has been imaged, the detection process is repeated for each subsequent active layer (e.g., Scan-2) while bypassing the adjacent inactive layer(s) by scanning along one axis (e.g., the z direction). Note, multiple two-dimensional planes may be acquired for the same amplicon clusters in the xy plane (e.g., Scan-1 and Scan-2) whereby detection events may be occurring on different z-planes within those amplicon clusters, or two-dimensional planes may be acquired for the different amplicon clusters in the xy plane (e.g., Scan-1 and Scan-3).

Imaging a multi-layer 3D scaffold including multiple active layers and inactive layers can be performed according to the methods described herein. During a sequencing process (e.g., SBS), optical sectioning using, for example, confocal microscopy or multi-photon excitation microscopy, is used to image a first active layer and detect one or more incorporated labeled nucleotides representative of one or more sequenced bases, independent of the labeled nucleotides present in all other active layers. Once the first layer has been imaged, the detection process is repeated for each subsequent active layer while bypassing the adjacent inactive layer(s), as illustrated in FIG. 4 by scanning along one axis (e.g., the z direction). In some embodiments, imaging of more than one active layer may occur simultaneously. For example, multiple imaging planes may be utilized to image and detect sequenced bases at one or more clusters of two or more active layers in the multi-layered scaffold. The presence of inactive layers between the plurality of active layers allows for spatial and optical separation of the imaged planes.

Figure 5A:
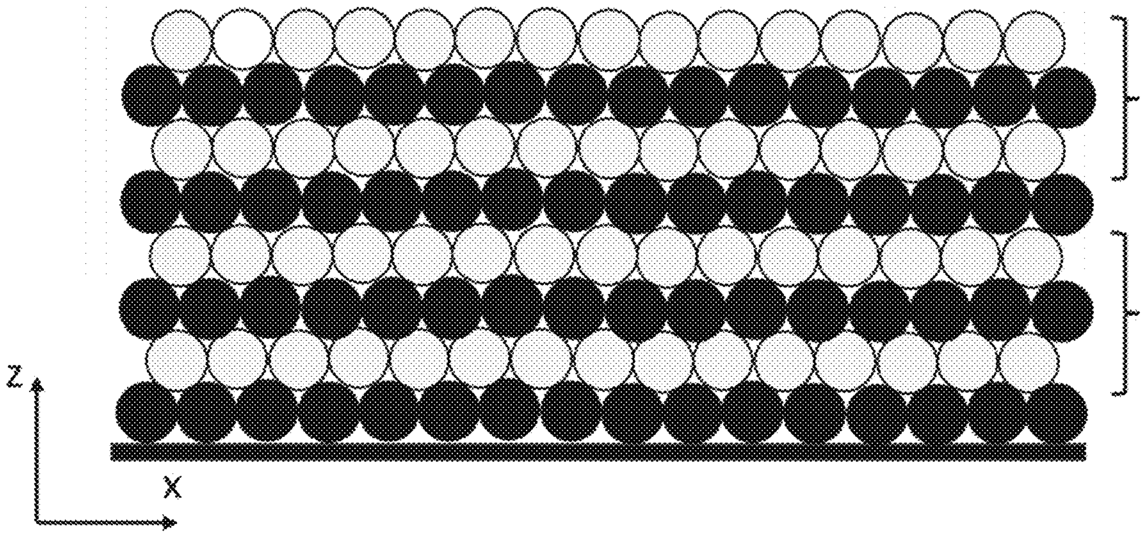
FIGS. 5A-5D illustrate multi-dimensional detection for polymer scaffolds including layers of active particles (e.g., particles including immobilized (i.e., attached) primers, shown as light-colored spheres) and passive layers (e.g., particles lacking attached primers referred to as "blanks", or an inactive polymer layer, shown as dark-colored spheres). Though depicted as dark-colored spheres, this is merely illustrative and not indicative that the particles in the passive layer are opaque or non-transparent.
Figure 5B:
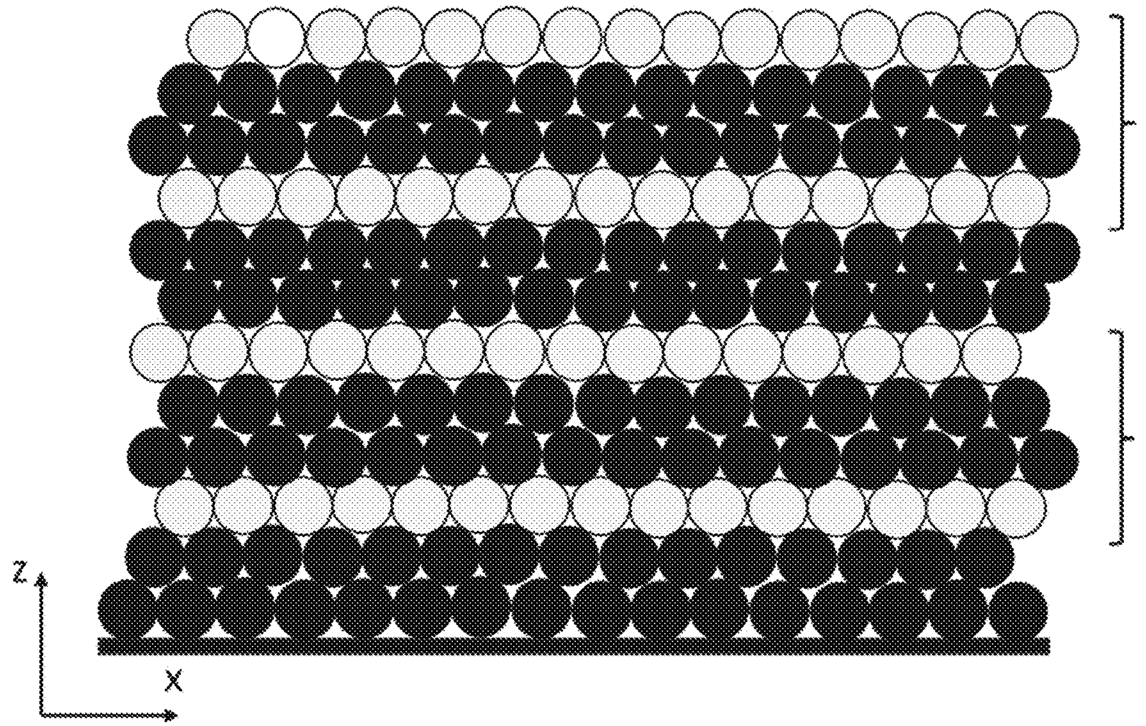

Multi-dimensional detection for polymer scaffolds including layers of active particles (e.g., particles including immobilized primers, shown as light-colored spheres) and passive layers (e.g., particles lacking covalently-attached primers, or an inactive polymer layer, shown as dark-colored spheres) is illustrated in FIGS. 5A-5D. FIGS. 5A-5B shows a polymer scaffold of particles (e.g., solid core or MOF core particles) arranged in an array. Not shown are the internal cores, which contain oligonucleotides, nor the multiple fluorescent events upon nucleotide incorporation within the particles. FIG. 5A shows a polymer scaffold of particles (e.g., core-shell particles) arranged in an array, wherein the inactive polymer layer includes a single layer of particles. FIG. 5B shows a polymer scaffold of particles (e.g., core-shell particles) arranged in an array, wherein the inactive polymer layer includes two layers of particles. As described herein, each set of two active layers separated by an inactive polymer layer may be referred to as a contiguous layered unit, as denoted by the brackets on the right-hand side of the particle scaffolds in FIGS. 5A-5B. In this illustration, each particle scaffold has two contiguous layered units, each separated by at least one inactive polymer layer.

Figure 5C:
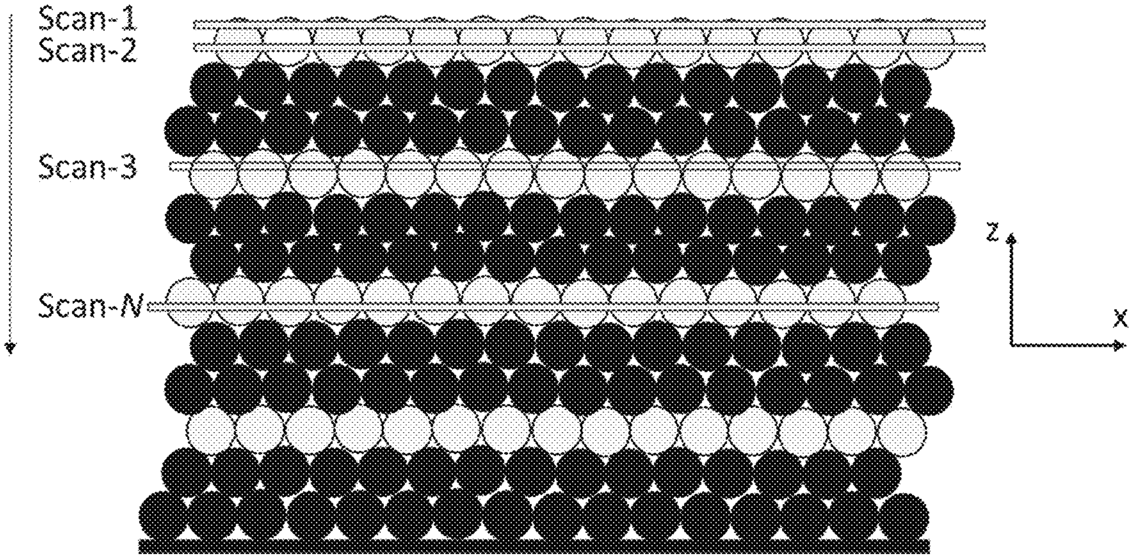
Figure 5D:
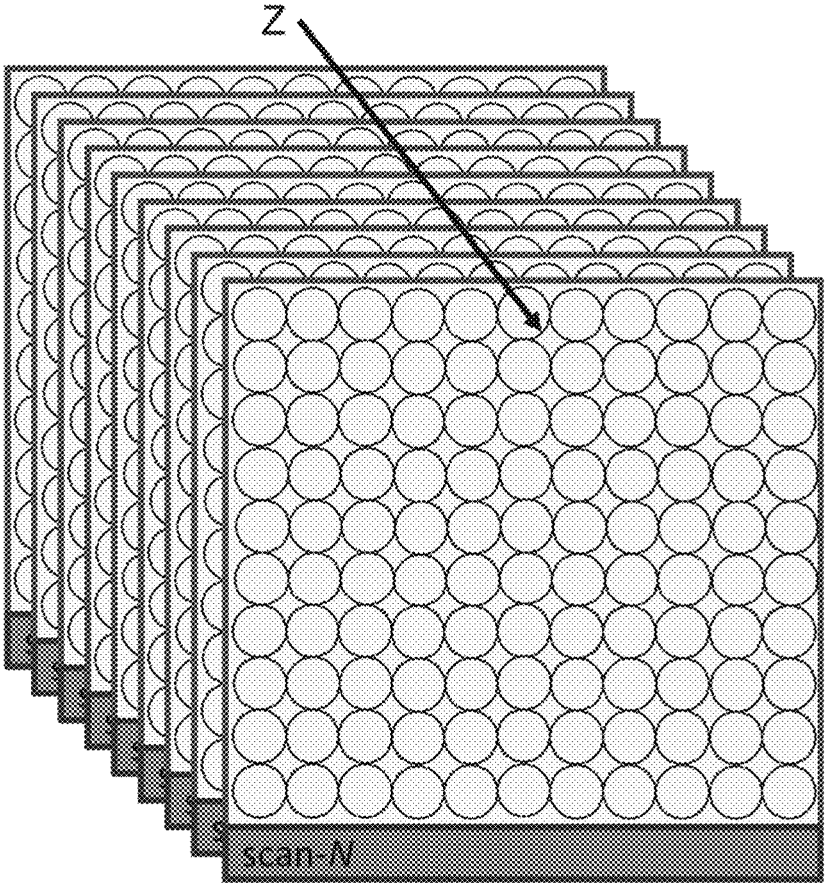

Using, e.g., confocal microscopy or multi-photon microscopy, two-dimensional planes of images are collected by scanning along one axis (e.g., the z direction), as illustrated in FIG. 5C. Note, multiple two-dimensional planes may be acquired for the same particles in the xy plane (e.g., Scan-1 and Scan-2) whereby detection events may be occurring on different z-planes within those particles, or two-dimensional planes may be acquired for the different particles in the xy plane (e.g., Scan-1 and Scan-3). These images, shown in FIG. 5D, may then be further processed to determine the fluorescent event, and thus the sequence of the target polynucleotide.

Scanning a single focal point across the field of view is likely to be too slow for many sequencing applications. To speed up the image acquisition, an array of multiple focal points can be used. The emission from each of these focal points can be imaged onto a detector, and the time information from the scanning mirrors can be translated into image coordinates. Alternatively, the multiple focal points can be used just for the purpose of confining the fluorescence to a narrow axial section, and the emission can be imaged onto an imaging detector, such as a CCD, EMCCD, or s-CMOS detector. A scientific grade CMOS detector offers an optimal combination of sensitivity, readout speed, and low cost. One configuration used for confocal microscopy is spinning disk confocal microscopy. In 2-photon microscopy, the technique of using multiple focal points simultaneously to parallelize the readout has been called Multifocal Two-Photon Microscopy (MTPM). Several techniques for MTPM are available, with applications typically involving imaging in biological tissue.

Additional imaging modalities include 3D Structured Illumination (3DSIM). In 3DSIM, spatially patterned light is used for excitation, and fringes in the Moiré pattern generated by interference of the illumination pattern and the sample, are used to reconstruct the source of light in three dimensions. Multiple spatial patterns are used to excite the same physical region in order to illuminate the whole field. Digital processing or analog methods are used to reconstruct the final image. See York, Andrew G., et al. "Instant super-resolution imaging in live cells and embryos via analog image processing." Nature methods 10.11 (2013): 1122-1126 and Gustafsson, Mats G L, et al. "Three-dimensional resolution doubling in wide-field fluorescence microscopy by structured illumination." Biophysical journal 94.12 (2008): 4957-4970 each of which are hereby incorporated by reference in their entireties. Two-photon, or multi-photon, microscopic modalities are useful structured illumination microscopy methods. See Denk W., Strickler J., Webb W. (1990). "Two-photon laser scanning fluorescence microscopy". Science 248 (4951): 73-6 hereby incorporated by reference in its entirety. Two-photon microscopy is a type of microscopy that enables imaging deep within a sample by using two photons per excitation event. These systems typically use long-wavelength light for excitation, which penetrates more effectively into tissue due to reduced scattering. The use of two-photon excitation also reduces background signal as single-photon absorption provides insufficient energy to excite emission by the fluorophore. Two-photon microscopy can also utilize larger or more efficient optical and sensor configurations to detect the emission, as the localization of excitation over time is known to the imaging system during scanning. Other benefits to this modality include reduced photodamage to the sample.

P-Embodiments

The present disclosure provides the following illustrative embodiments.

Embodiment P1. A composition comprising: (i) a first layer comprising a polymeric gel comprising a plurality of oligonucleotides attached to said polymeric gel; (ii) a second layer comprising a polymeric gel, wherein said polymeric gel does not comprise a plurality of oligonucleotides attached to said polymeric gel; and (iii) a third layer comprising a polymeric gel comprising a plurality of oligonucleotides attached to said polymeric gel.

Embodiment P2. A composition comprising: (i) a first layer comprising a polymeric gel comprising a plurality of particles, each particle comprising a plurality of oligonucleotide moieties covalently attached to said particle via a polymeric bioconjugate linker; (ii) a second layer comprising a polymeric gel comprising a plurality of particles, wherein each particle does not comprise a plurality of oligonucleotide moieties; and (iii) a third layer comprising a polymeric gel comprising a plurality of particles, each particle comprising a plurality of oligonucleotide moieties covalently attached to said particle via a polymeric bioconjugate linker.

Embodiment P3. A composition comprising: (i) a first layer comprising a plurality of particles, each particle comprising a plurality of oligonucleotide moieties covalently attached to said particle via a polymeric bioconjugate linker; (ii) a second layer comprising a plurality of particles, wherein each particle does not comprise a plurality of oligonucleotide moieties; and (iii) a third layer comprising a plurality of particles, each particle comprising a plurality of oligonucleotide moieties covalently attached to said particle via a polymeric bioconjugate linker.

Embodiment P4. The composition of Embodiment P1, wherein said first layer and third layer each comprise a polymeric gel comprising said plurality of oligonucleotides covalently attached to said polymeric gel.

Embodiment P5. The composition of Embodiment P1 or Embodiment P2, wherein the polymeric gel is permeable to a sequencing reaction mixture.

Embodiment P6. The composition of Embodiment P2 or Embodiment P3, wherein each particle is permeable to a sequencing reaction mixture.

Embodiment P7. The composition of any one of Embodiment P1 to Embodiment P6, wherein the first layer is immediately adjacent to the second layer, wherein the third layer is immediately adjacent to the second layer, and wherein the first layer and third layer are not immediately adjacent.

Embodiment P8. The composition of any one of Embodiment P1 to Embodiment P7, wherein the first layer, second layer, and third layer are in fluidic contact.

Embodiment P9. The composition of any one of Embodiment P1 to Embodiment P8, wherein the first, second, and third layers form a contiguous layered unit.

Embodiment P10. The composition of Embodiment P9, further comprising two or more contiguous layered units.

Embodiment P11. The composition of any one of Embodiment P1 to Embodiment P10, wherein each layer is substantially planar.

Embodiment P12. The composition of any one of Embodiment P1 to Embodiment P11, wherein the composition is attached to a solid support.

Embodiment P13. The composition of any one of Embodiment P1 to Embodiment P12, wherein each layer has a width of about 1-20 mm, a length of about 1-20 cm, and a depth of about 0.5-15 μm.

Embodiment P14. The composition of any one of Embodiment P1 to Embodiment P13, wherein the first layer, the third layer, or both the first layer and the third layer are attached to a solid support.

Embodiment P15. The composition of any one of Embodiment P9 to Embodiment P14, wherein at least one contiguous layered unit is attached to a solid support.

Embodiment P16. The composition of any one of Embodiment P2 to Embodiment P15, wherein the plurality of particles are uniformly arranged.

Embodiment P17. The composition of any one of Embodiment P2 to Embodiment P15, wherein the plurality of particles are not uniformly arranged.

Embodiment P18. The composition of any one of Embodiment P1 to Embodiment P17, wherein the polymeric gel, plurality of particles, or both, comprise water.

Embodiment P19. The composition of any one of Embodiment P1 to Embodiment P18, wherein the polymeric gel, plurality of particles, or both, have a refractive index of about 1.3 when hydrated.

Embodiment P20. A method of amplifying a template polynucleotide, the method comprising: (a) annealing a template polynucleotide to a first oligonucleotide of the composition of any one of Embodiment P1 to Embodiment P19; (b) extending the first oligonucleotide with a polymerase to generate a complement template polynucleotide; (c) contacting the complement template polynucleotide and the template polynucleotide with a chemical denaturant thereby separating the complement template polynucleotide from the template polynucleotide; (d) removing the chemical denaturant and annealing the complement template polynucleotide to a second oligonucleotide on said composition; and (e) extending the second oligonucleotide with the polymerase to generate a template polynucleotide, thereby amplifying the template polynucleotide.

Embodiment P21. A method of amplifying a template polynucleotide, the method comprising: (i) contacting the composition of any one of Embodiment P1 to Embodiment P19 with an annealing solution, wherein one or more of the oligonucleotides anneals to the template polynucleotide; (ii) contacting the composition with an extension solution; (iii) contacting the composition with a chemical denaturant; (iv)repeating steps (i)-(iii) to amplify the template polynucleotide.

Embodiment P22. A method of sequencing a plurality of template polynucleotides, the method comprising: (a) hybridizing the plurality of template polynucleotides to the plurality of oligonucleotides of the composition of any one of Embodiment P1 to Embodiment P19; (b) amplifying the template polynucleotides to produce discrete amplicon clusters, wherein (i) amplifying comprises extension of the oligonucleotides along the template polynucleotides within each first layer and third layer, (ii) each amplicon cluster originates from amplification of a single template polynucleotide, and (iii) the amplicon clusters are arranged at a plurality of depths in each first layer and third layer; and (c) sequencing the amplicon clusters, wherein sequencing comprises detecting sequences of signals within each first layer and third layer of the composition at a first depth and a second depth.

Embodiment P23. The method of any one of Embodiment P20 to Embodiment P22, wherein the first oligonucleotide is complementary to a sequence of a concatemer of complement template polynucleotides.

Embodiment P24. A composition comprising two or more contiguous layered units, wherein each of the two or more contiguous layered units comprises a first layer and a third layer, wherein each first and third layer comprises a polymeric gel comprising a plurality of oligonucleotides attached to said polymeric gel, wherein every first and third layer of the two or more contiguous layered units is separated by a second layer comprising a passive polymeric gel, wherein said passive polymeric gel does not comprise a plurality of oligonucleotides attached to said passive polymeric gel.

Embodiment P25. The composition of Embodiment P24, wherein the plurality of oligonucleotides of each of the two or more contiguous layered units is covalently attached to said polymeric gel.

Embodiment P26. A solid support comprising a multi-layer polymer, wherein said multi-layer polymer comprises: a first layer attached to said solid support, wherein said first layer comprises a first oligonucleotide within a first polymer layer, and a second layer, wherein said second layer does not comprise an amplification primer binding sequence within a second polymer layer, wherein said first polymer layer is attached to said second polymer layer, and wherein said first oligonucleotide comprises a first amplification primer binding sequence and a first sequencing primer binding sequence.

Embodiment P27. The solid support of Embodiment P26, further comprising a third layer attached to said second layer, wherein said third layer comprises a second oligonucleotide within a third polymer layer, wherein and said second oligonucleotide comprises a second amplification primer binding sequence and a second sequencing primer binding sequence.

Embodiment P28. The solid support of Embodiment P26, wherein the first layer further comprises a third oligonucleotide within said first polymer layer.

Embodiment P29. The solid support of Embodiment P27 or Embodiment P28, wherein the third layer further comprises a fourth oligonucleotide within said third polymer layer.

Embodiment P30. The solid support of any one of Embodiment P26 to Embodiment P29, wherein each layer is substantially planar.

Embodiment P31. The solid support of any one of Embodiment P26 to Embodiment P30, wherein the solid support is substantially planar.

Embodiment P32. The solid support of any one of Embodiment P26 to Embodiment P31, wherein each layer has a width of about 1-20 mm, a length of about 1-20 cm, and a depth of about 0.5-15 μm.

Embodiment P33. The solid support of any one of Embodiment P27 to Embodiment P32, wherein the first layer, the third layer, or both the first layer and the third layer are attached to a solid support.

Embodiment P34. The solid support of any one of Embodiment P27 to Embodiment P32, wherein the first amplification primer binding sequence and the second amplification primer binding sequence are the same.

Embodiment P35. A method of amplifying a polynucleotide, said method comprising: contacting a solid support comprising a multi-layer polymer with a polynucleotide, and amplifying the polynucleotide with a polymerase and a plurality of nucleotides to generate amplification products, wherein said multi-layer polymer comprises: a first layer attached to said solid support, wherein said first layer comprises a first oligonucleotide within a first polymer layer, wherein said first oligonucleotide comprises a first amplification primer binding sequence and a first sequencing primer binding sequence, a second layer, wherein said second layer does not comprise an amplification primer binding sequence within a second polymer layer, and a third layer attached to said second layer, wherein said third layer comprises a second oligonucleotide within a third polymer layer, wherein and said second oligonucleotide comprises a second amplification primer binding sequence and a second sequencing primer binding sequence, wherein said second polymer layer is attached to said first and third polymer layer.

Embodiment P36. The method of Embodiment P35, wherein the first amplification primer binding sequence and the second amplification primer binding sequence are the same.

Embodiment P37. The method of Embodiment P35 or Embodiment P36, wherein amplifying comprises bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, emulsion PCR, or combinations thereof. In embodiments, amplifying includes bridge polymerase chain reaction (bPCR) amplification, solid-phase rolling circle amplification (RCA), or solid-phase exponential rolling circle amplification (eRCA).

Embodiment P38. The method of any one of Embodiment P35 to Embodiment P37, further comprising detecting the amplification products.

Embodiment P39. The method of Embodiment P38, wherein detecting comprises sequencing.

Embodiment 1. A method of amplifying a polynucleotide, said method comprising: contacting a solid support comprising a multi-layer polymer with a polynucleotide, and amplifying the polynucleotide with a polymerase and a plurality of nucleotides to generate amplification products, wherein said multi-layer polymer comprises: first layer attached to said solid support, wherein said first layer comprises a first oligonucleotide within a first polymer layer, wherein said first oligonucleotide comprises a first amplification primer binding sequence and a first sequencing primer binding sequence; a second layer, wherein said second layer does not comprise an amplification primer binding sequence within a second polymer layer; and a third layer attached to said second layer, wherein said third layer comprises a second oligonucleotide within a third polymer layer, wherein and said second oligonucleotide comprises a second amplification primer binding sequence and a second sequencing primer binding sequence, wherein said second polymer layer is attached to said first and third polymer layer.

Embodiment 2. The method of Embodiment 1, wherein the first amplification primer binding sequence and the second amplification primer binding sequence comprise the same sequence.

Embodiment 3. The method of Embodiment 1 or Embodiment 2, wherein amplifying comprises bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, emulsion PCR, or combinations thereof. In embodiments, amplifying includes bridge polymerase chain reaction (bPCR) amplification, solid-phase rolling circle amplification (RCA), or solid-phase exponential rolling circle amplification (eRCA).

Embodiment 4. The method of any one of Embodiments 1 to 3, further comprising detecting the amplification products.

Embodiment 5. The method of Embodiment 4, wherein detecting comprises sequencing.

Embodiment 6. The method of Embodiment 5, wherein sequencing the target polynucleotides comprises sequencing-by-synthesis, sequencing-by-binding, sequencing by ligation, or pyrosequencing, and generates a sequencing read.

Embodiment 7. The method of Embodiment 5, wherein sequencing comprises contacting the amplification products with a first sequencing primer, extending the first sequencing primer to incorporate a detectable label that indicates the identity of a nucleotide in the amplification products, detecting the detectable label, and repeating the extending and detecting steps, wherein said first sequencing primer is complementary to said first sequencing primer binding sequence of said first oligonucleotide.

Embodiment 8. The method of Embodiment 7, wherein sequencing further comprises contacting the amplification products with a second sequencing primer, extending the second sequencing primer to incorporate a detectable label that indicates the identity of a nucleotide in the amplification products, detecting the detectable label, and repeating the extending and detecting steps, wherein said second sequencing primer is complementary to said second sequencing primer binding sequence of said second oligonucleotide.

Embodiment 9. A composition comprising: (i) a first layer comprising a polymeric gel comprising a plurality of oligonucleotides attached to said polymeric gel; (ii) a second layer comprising a polymeric gel, wherein said polymeric gel does not comprise a plurality of oligonucleotides attached to said polymeric gel; and (iii) a third layer comprising a polymeric gel comprising a plurality of oligonucleotides attached to said polymeric gel.

Embodiment 10. A composition comprising: (i) a first layer comprising a polymeric gel comprising a plurality of particles, each particle comprising a plurality of oligonucleotide moieties covalently attached to said particle via a polymeric bioconjugate linker; (ii) a second layer comprising a polymeric gel comprising a plurality of particles, wherein each particle does not comprise a plurality of oligonucleotide moieties; and (iii) a third layer comprising a polymeric gel comprising a plurality of particles, each particle comprising a plurality of oligonucleotide moieties covalently attached to said particle via a polymeric bioconjugate linker.

Embodiment 11. A composition comprising: (i) a first layer comprising a plurality of particles, each particle comprising a plurality of oligonucleotide moieties covalently attached to said particle via a polymeric bioconjugate linker; (ii) a second layer comprising a plurality of particles, wherein each particle does not comprise a plurality of oligonucleotide moieties; and (iii) a third layer comprising a plurality of particles, each particle comprising a plurality of oligonucleotide moieties covalently attached to said particle via a polymeric bioconjugate linker.

Embodiment 12. The composition of Embodiment 9, wherein said first layer and third layer each comprise a polymeric gel comprising said plurality of oligonucleotides covalently attached to said polymeric gel.

Embodiment 13. The composition of Embodiment 9, wherein the polymeric gel is permeable to a sequencing reaction mixture.

Embodiment 14. The composition of Embodiment 11, wherein each particle is permeable to a sequencing reaction mixture.

Embodiment 15. The composition of Embodiment 9, wherein the first layer is immediately adjacent to the second layer, wherein the third layer is immediately adjacent to the second layer, and wherein the first layer and third layer are not immediately adjacent.

Embodiment 16. The composition of Embodiment 9, wherein the first layer, second layer, and third layer are in fluidic contact.

Embodiment 17. The composition of Embodiment 9, wherein the first, second, and third layers form a contiguous layered unit.

Embodiment 18. The composition of Embodiment 17, further comprising two or more contiguous layered units.

Embodiment 19. The composition of Embodiment 9, wherein each layer is substantially planar.

Embodiment 20. The composition of Embodiment 9, wherein the composition is attached to a solid support.

Embodiment 21. The composition of Embodiment 9, wherein each layer has a width of about 1-20 mm, a length of about 1-20 cm, and a depth of about 0.5-15 μm.

Embodiment 22. The composition of Embodiment 9, wherein the first layer, the third layer, or both the first layer and the third layer are attached to a solid support.

Embodiment 23. The composition of Embodiment 17, wherein at least one contiguous layered unit is attached to a solid support.

Embodiment 24. The composition of Embodiment 10, wherein the plurality of particles are uniformly arranged.

Embodiment 25. The composition of Embodiment 9, wherein the plurality of particles are not uniformly arranged.

Embodiment 26. The composition of Embodiment 9, wherein the polymeric gel, plurality of particles, or both, comprise water.

Embodiment 27. The composition of Embodiment 9, wherein the polymeric gel, plurality of particles, or both, have a refractive index of about 1.3 when hydrated.

Embodiment 28. A method of amplifying a template polynucleotide, the method comprising: (a) annealing a template polynucleotide to a first oligonucleotide of the composition of Embodiment 9; (b) extending the first oligonucleotide with a polymerase to generate a complement template polynucleotide; (c) contacting the complement template polynucleotide and the template polynucleotide with a chemical denaturant thereby separating the complement template polynucleotide from the template polynucleotide; (d) removing the chemical denaturant and annealing the complement template polynucleotide to a second oligonucleotide on said composition; and (e) extending the second oligonucleotide with the polymerase to generate a template polynucleotide, thereby amplifying the template polynucleotide.

Embodiment 29. A method of amplifying a template polynucleotide, the method comprising: (i) contacting the composition of Embodiment 9 with an annealing solution, wherein one or more of the oligonucleotides anneals to the template polynucleotide; (ii) contacting the composition with an extension solution; (iii) contacting the composition with a chemical denaturant; (iv) repeating steps (i)-(iii) to amplify the template polynucleotide.

Embodiment 30. A method of sequencing a plurality of template polynucleotides, the method comprising: (a) hybridizing the plurality of template polynucleotides to the plurality of oligonucleotides of the composition of Embodiment 9; (b) amplifying the template polynucleotides to produce discrete amplicon clusters, wherein (i) amplifying comprises extension of the oligonucleotides along the template polynucleotides within each first layer and third layer, (ii) each amplicon cluster originates from amplification of a single template polynucleotide, and (iii) the amplicon clusters are arranged at a plurality of depths in each first layer and third layer; and (c) sequencing the amplicon clusters, wherein sequencing comprises detecting sequences of signals within each first layer and third layer of the composition at a first depth and a second depth.

Embodiment 31. The method of Embodiment 28, wherein the first oligonucleotide is complementary to a sequence of a concatemer of complement template polynucleotides.

Embodiment 32. A composition comprising two or more contiguous layered units, wherein each of the two or more contiguous layered units comprises a first layer and a third layer, wherein each first and third layer comprises a polymeric gel comprising a plurality of oligonucleotides attached to said polymeric gel, wherein every first and third layer of the two or more contiguous layered units is separated by a second layer comprising a passive polymeric gel, wherein said passive polymeric gel does not comprise a plurality of oligonucleotides attached to said passive polymeric gel.

Embodiment 33. The composition of Embodiment 32, wherein the plurality of oligonucleotides of each of the two or more contiguous layered units is covalently attached to said polymeric gel.

Embodiment 34. A solid support comprising a multi-layer polymer, wherein said multi-layer polymer comprises: a first layer attached to said solid support, wherein said first layer comprises a first oligonucleotide within a first polymer layer, and a second layer, wherein said second layer does not comprise an amplification primer binding sequence within a second polymer layer, wherein said first polymer layer is attached to said second polymer layer, and wherein said first oligonucleotide comprises a first amplification primer binding sequence and a first sequencing primer binding sequence.

Embodiment 35. The solid support of Embodiment 34, further comprising a third layer attached to said second layer, wherein said third layer comprises a second oligonucleotide within a third polymer layer, wherein and said second oligonucleotide comprises a second amplification primer binding sequence and a second sequencing primer binding sequence.

Embodiment 36. The solid support of Embodiment 34, wherein the first layer further comprises a third oligonucleotide within said first polymer layer.

Embodiment 37. The solid support of Embodiment 35, wherein the third layer further comprises a fourth oligonucleotide within said third polymer layer.

Embodiment 38. The solid support of Embodiment 34, wherein each layer is substantially planar.

Embodiment 39. The solid support of Embodiment 34, wherein the solid support is substantially planar.

Embodiment 40. The solid support of Embodiment 34, wherein each layer has a width of about 1-20 mm, a length of about 1-20 cm, and a depth of about 0.5-15 μm.

Embodiment 41. The solid support of Embodiment 35, wherein the first layer, the third layer, or both the first layer and the third layer are attached to a solid support.

Embodiment 42. The solid support of Embodiment 35, wherein the first amplification primer binding sequence and the second amplification primer binding sequence are the same.

What is claimed is:

1. A method of amplifying a polynucleotide, said method comprising:

contacting a solid support comprising a multi-layer polymer with a polynucleotide, and amplifying the polynucleotide with a polymerase and a plurality of nucleotides to generate amplification products, wherein said multi-layer polymer comprises:

a first layer attached to said solid support, wherein said first layer comprises a first oligonucleotide within a first polymer layer, wherein said first oligonucleotide comprises a first amplification primer binding sequence and a first sequencing primer binding sequence;

a second layer, wherein said second layer does not comprise an amplification primer binding sequence within a second polymer layer; and a third layer attached to said second layer, wherein said third layer comprises a second oligonucleotide within a third polymer layer, wherein said second oligonucleotide comprises a second amplification primer binding sequence and a second sequencing primer binding sequence, wherein said second polymer layer is attached to said first and third polymer layer.

2. The method of claim 1, wherein the first amplification primer binding sequence and the second amplification primer binding sequence comprise the same sequence.

3. The method of claim 1, wherein amplifying comprises bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, emulsion PCR, or combinations thereof.

4. The method of claim 1, further comprising detecting the amplification products, wherein detecting comprises sequencing.

5. The method of claim 4, wherein sequencing comprises sequencing-by-synthesis, sequencing-by-binding, sequencing by ligation, or pyrosequencing, and generates a sequencing read.

6. The method of claim 4, wherein sequencing comprises contacting the amplification products with a first sequencing primer, extending the first sequencing primer to incorporate a detectable label that indicates the identity of a nucleotide in the amplification products, detecting the detectable label, and repeating the extending and detecting steps, wherein said first sequencing primer is complementary to said first sequencing primer binding sequence of said first oligonucleotide.

7. The method of claim 6, wherein sequencing further comprises contacting the amplification products with a second sequencing primer, extending the second sequencing primer to incorporate a detectable label that indicates the identity of a nucleotide in the amplification products, detecting the detectable label, and repeating the extending and detecting steps, wherein said second sequencing primer is complementary to said second sequencing primer binding sequence of said second oligonucleotide.

8. A composition comprising:

(i) a first layer comprising a polymeric gel comprising a plurality of oligonucleotides attached to said polymeric gel;

(ii) a second layer comprising a polymeric gel, wherein said polymeric gel does not comprise a plurality of oligonucleotides attached to said polymeric gel; and (iii) a third layer comprising a polymeric gel comprising a plurality of oligonucleotides attached to said polymeric gel.

9. The composition of claim 8, wherein said first layer and third layer each comprise a polymeric gel comprising said plurality of oligonucleotides covalently attached to said polymeric gel.

10. The composition of claim 8, wherein the first layer is immediately adjacent to the second layer, wherein the third layer is immediately adjacent to the second layer, and wherein the first layer and third layer are not immediately adjacent.

11. The composition of claim 8, wherein the first layer, second layer, and third layer are in fluidic contact.

12. The composition of claim 8, wherein the first, second, and third layers form a contiguous layered unit.

13. The composition of claim 12, further comprising two or more contiguous layered units.

14. The composition of claim 8, wherein each layer has a width of about 1-20 mm, a length of about 1-20 cm, and a depth of about 0.5-15 μm.

15. The composition of claim 8, wherein the first layer, the third layer, or both the first layer and the third layer are attached to a solid support.

16. The composition of claim 8, wherein the polymeric gel comprises a refractive index of about 1.3 when hydrated.

17. A method of amplifying a template polynucleotide, the method comprising:

(a) annealing a template polynucleotide to a first oligonucleotide of the composition of claim 8;

(b) extending the first oligonucleotide with a polymerase to generate a complement template polynucleotide;

(c) contacting the complement template polynucleotide and the template polynucleotide with a chemical denaturant thereby separating the complement template polynucleotide from the template polynucleotide;

(d) removing the chemical denaturant and annealing the complement template polynucleotide to a second oligonucleotide on said composition; and (e) extending the second oligonucleotide with the polymerase to generate a template polynucleotide, thereby amplifying the template polynucleotide.

18. A method of amplifying a template polynucleotide, the method comprising:

(i) contacting the composition of claim 8 with an annealing solution, wherein one or more of the oligonucleotides anneals to the template polynucleotide;

(ii) contacting the composition with an extension solution;

(iii) contacting the composition with a chemical denaturant;

(iv) repeating steps (i)-(iii) to amplify the template polynucleotide.

19. A method of sequencing a plurality of template polynucleotides, the method comprising:

(a) hybridizing the plurality of template polynucleotides to the plurality of oligonucleotides of the composition of claim 8;

(b) amplifying the template polynucleotides to produce discrete amplicon clusters, wherein (i) amplifying comprises extension of the oligonucleotides along the template polynucleotides within each first layer and third layer, (ii) each amplicon cluster originates from amplification of a single template polynucleotide, and (iii) the amplicon clusters are arranged at a plurality of depths in each first layer and third layer; and (c) sequencing the amplicon clusters, wherein sequencing comprises detecting sequences of signals within each first layer and third layer of the composition at a first depth and a second depth.

20. A solid support comprising a multi-layer polymer, wherein said multi-layer polymer comprises:

a first layer attached to said solid support, wherein said first layer comprises a first oligonucleotide within a first polymer layer, and said first oligonucleotide comprises a first amplification primer binding sequence and a first sequencing primer binding sequence;

a second layer, wherein said second layer does not comprise an amplification primer binding sequence within a second polymer layer, wherein said first polymer layer is attached to said second polymer layer; and a third layer attached to said second layer, wherein said third layer comprises a second oligonucleotide within a third polymer layer, wherein said second oligonucleotide comprises a second amplification primer binding sequence and a second sequencing primer binding sequence.

* * * * *

SEQUENCE LISTING

```
Sequence total quantity: 96
SEQ ID NO: 1            moltype = DNA  length = 33
FEATURE                 Location/Qualifiers
source                  1..33
                        mol_type = other DNA
                        organism = synthetic construct
SEQUENCE: 1
```

```
aacgccaaac ctacggcttt acttcctgtg gct                              33

SEQ ID NO: 2            moltype = DNA  length = 33
FEATURE                 Location/Qualifiers
source                  1..33
                        mol_type = other DNA
                        organism = synthetic construct
SEQUENCE: 2
tcttgagtca ttcgcagggc atgtgccaga cct                              33

SEQ ID NO: 3            moltype = DNA  length = 33
FEATURE                 Location/Qualifiers
source                  1..33
                        mol_type = other DNA
                        organism = synthetic construct
SEQUENCE: 3
tcggcgttgt ctgctatcgt tcttggcact cct                              33

SEQ ID NO: 4            moltype = DNA  length = 33
FEATURE                 Location/Qualifiers
source                  1..33
                        mol_type = other DNA
                        organism = synthetic construct
SEQUENCE: 4
ggagcaataa ccataaggcc gttgacaagc cct                              33

SEQ ID NO: 5            moltype = DNA  length = 33
FEATURE                 Location/Qualifiers
source                  1..33
                        mol_type = other DNA
                        organism = synthetic construct
SEQUENCE: 5
ggcgtattgc cttggttctg gcagcctcat tgt                              33

SEQ ID NO: 6            moltype = DNA  length = 33
FEATURE                 Location/Qualifiers
source                  1..33
                        mol_type = other DNA
                        organism = synthetic construct
SEQUENCE: 6
cagcagaggg aacgatttca acttcctgtg gct                              33

SEQ ID NO: 7            moltype = DNA  length = 33
FEATURE                 Location/Qualifiers
source                  1..33
                        mol_type = other DNA
                        organism = synthetic construct
SEQUENCE: 7
ctactgcaag ggtgtctaga atgtgccaga cct                              33

SEQ ID NO: 8            moltype = DNA  length = 33
FEATURE                 Location/Qualifiers
source                  1..33
                        mol_type = other DNA
                        organism = synthetic construct
SEQUENCE: 8
gaccgactcg tgaaacgtaa tcttggcact cct                              33

SEQ ID NO: 9            moltype = DNA  length = 33
FEATURE                 Location/Qualifiers
source                  1..33
                        mol_type = other DNA
                        organism = synthetic construct
SEQUENCE: 9
acacattctt tgcgcccaga gttgacaagc cct                              33

SEQ ID NO: 10           moltype = DNA  length = 33
FEATURE                 Location/Qualifiers
source                  1..33
                        mol_type = other DNA
                        organism = synthetic construct
SEQUENCE: 10
atttcattcg acacccggtc gcagcctcat tgt                              33

SEQ ID NO: 11           moltype = DNA  length = 33
FEATURE                 Location/Qualifiers
source                  1..33
                        mol_type = other DNA
                        organism = synthetic construct
```

```
SEQUENCE: 11
tcggtgtcct tcatttcggc atccaaaccg caa                          33

SEQ ID NO: 12          moltype = DNA  length = 33
FEATURE                Location/Qualifiers
source                 1..33
                       mol_type = other DNA
                       organism = synthetic construct
SEQUENCE: 12
tccagaccgt gtacgggacg cttactgagt tct                          33

SEQ ID NO: 13          moltype = DNA  length = 33
FEATURE                Location/Qualifiers
source                 1..33
                       mol_type = other DNA
                       organism = synthetic construct
SEQUENCE: 13
tcctcacggt tcttgctatc gtctgttgcg gct                          33

SEQ ID NO: 14          moltype = DNA  length = 33
FEATURE                Location/Qualifiers
source                 1..33
                       mol_type = other DNA
                       organism = synthetic construct
SEQUENCE: 14
tcccgaacag ttgccggaat accaataacg agg                          33

SEQ ID NO: 15          moltype = DNA  length = 33
FEATURE                Location/Qualifiers
source                 1..33
                       mol_type = other DNA
                       organism = synthetic construct
SEQUENCE: 15
tgttactccg acggtcttgg ttccgttatg cgg                          33

SEQ ID NO: 16          moltype = DNA  length = 33
FEATURE                Location/Qualifiers
source                 1..33
                       mol_type = other DNA
                       organism = synthetic construct
SEQUENCE: 16
tcggtgtcct tcaactttag caagggagac gac                          33

SEQ ID NO: 17          moltype = DNA  length = 33
FEATURE                Location/Qualifiers
source                 1..33
                       mol_type = other DNA
                       organism = synthetic construct
SEQUENCE: 17
tccagaccgt gtaagatctg tgggaacgtc atc                          33

SEQ ID NO: 18          moltype = DNA  length = 33
FEATURE                Location/Qualifiers
source                 1..33
                       mol_type = other DNA
                       organism = synthetic construct
SEQUENCE: 18
tcctcacggt tctaatgcaa agtgctcagc cag                          33

SEQ ID NO: 19          moltype = DNA  length = 33
FEATURE                Location/Qualifiers
source                 1..33
                       mol_type = other DNA
                       organism = synthetic construct
SEQUENCE: 19
tcccgaacag ttgagacccg cgtttcttac aca                          33

SEQ ID NO: 20          moltype = DNA  length = 33
FEATURE                Location/Qualifiers
source                 1..33
                       mol_type = other DNA
                       organism = synthetic construct
SEQUENCE: 20
tgttactccg acgctggccc acagcttact tta                          33

SEQ ID NO: 21          moltype = DNA  length = 33
FEATURE                Location/Qualifiers
source                 1..33
                       mol_type = other DNA
```

```
                       organism = synthetic construct
SEQUENCE: 21
ttgcggtttg gatgccgaaa tgaaggacac cga                              33

SEQ ID NO: 22          moltype = DNA  length = 33
FEATURE                Location/Qualifiers
source                 1..33
                       mol_type = other DNA
                       organism = synthetic construct
SEQUENCE: 22
agaactcagt aagcgtcccg tacacggtct gga                              33

SEQ ID NO: 23          moltype = DNA  length = 33
FEATURE                Location/Qualifiers
source                 1..33
                       mol_type = other DNA
                       organism = synthetic construct
SEQUENCE: 23
agccgcaaca gacgatagca agaaccgtga gga                              33

SEQ ID NO: 24          moltype = DNA  length = 33
FEATURE                Location/Qualifiers
source                 1..33
                       mol_type = other DNA
                       organism = synthetic construct
SEQUENCE: 24
cctcgttatt ggtattccgg caactgttcg gga                              33

SEQ ID NO: 25          moltype = DNA  length = 33
FEATURE                Location/Qualifiers
source                 1..33
                       mol_type = other DNA
                       organism = synthetic construct
SEQUENCE: 25
ccgcataacg gaaccaagac cgtcggagta aca                              33

SEQ ID NO: 26          moltype = DNA  length = 33
FEATURE                Location/Qualifiers
source                 1..33
                       mol_type = other DNA
                       organism = synthetic construct
SEQUENCE: 26
gtcgtctccc ttgctaaagt tgaaggacac cga                              33

SEQ ID NO: 27          moltype = DNA  length = 33
FEATURE                Location/Qualifiers
source                 1..33
                       mol_type = other DNA
                       organism = synthetic construct
SEQUENCE: 27
gatgacgttc ccacagatct tacacggtct gga                              33

SEQ ID NO: 28          moltype = DNA  length = 33
FEATURE                Location/Qualifiers
source                 1..33
                       mol_type = other DNA
                       organism = synthetic construct
SEQUENCE: 28
ctggctgagc actttgcatt agaaccgtga gga                              33

SEQ ID NO: 29          moltype = DNA  length = 33
FEATURE                Location/Qualifiers
source                 1..33
                       mol_type = other DNA
                       organism = synthetic construct
SEQUENCE: 29
tgtgtaagaa acgcgggtct caactgttcg gga                              33

SEQ ID NO: 30          moltype = DNA  length = 33
FEATURE                Location/Qualifiers
source                 1..33
                       mol_type = other DNA
                       organism = synthetic construct
SEQUENCE: 30
taaagtaagc tgtgggccag cgtcggagta aca                              33

SEQ ID NO: 31          moltype = DNA  length = 33
FEATURE                Location/Qualifiers
source                 1..33
```

-continued

```
                         mol_type = other DNA
                         organism = synthetic construct
SEQUENCE: 31
agccacagga agtaaagccg taggtttggc gtt                              33

SEQ ID NO: 32            moltype = DNA  length = 33
FEATURE                  Location/Qualifiers
source                   1..33
                         mol_type = other DNA
                         organism = synthetic construct
SEQUENCE: 32
aggtctggca catgccctgc gaatgactca aga                              33

SEQ ID NO: 33            moltype = DNA  length = 33
FEATURE                  Location/Qualifiers
source                   1..33
                         mol_type = other DNA
                         organism = synthetic construct
SEQUENCE: 33
aggagtgcca agaacgatag cagacaacgc cga                              33

SEQ ID NO: 34            moltype = DNA  length = 33
FEATURE                  Location/Qualifiers
source                   1..33
                         mol_type = other DNA
                         organism = synthetic construct
SEQUENCE: 34
agggcttgtc aacggcctta tggttattgc tcc                              33

SEQ ID NO: 35            moltype = DNA  length = 33
FEATURE                  Location/Qualifiers
source                   1..33
                         mol_type = other DNA
                         organism = synthetic construct
SEQUENCE: 35
acaatgaggc tgccagaacc aaggcaatac gcc                              33

SEQ ID NO: 36            moltype = DNA  length = 33
FEATURE                  Location/Qualifiers
source                   1..33
                         mol_type = other DNA
                         organism = synthetic construct
SEQUENCE: 36
agccacagga agttgaaatc gttccctctg ctg                              33

SEQ ID NO: 37            moltype = DNA  length = 33
FEATURE                  Location/Qualifiers
source                   1..33
                         mol_type = other DNA
                         organism = synthetic construct
SEQUENCE: 37
aggtctggca cattctagac acccttgcag tag                              33

SEQ ID NO: 38            moltype = DNA  length = 33
FEATURE                  Location/Qualifiers
source                   1..33
                         mol_type = other DNA
                         organism = synthetic construct
SEQUENCE: 38
aggagtgcca agattacgtt tcacgagtcg gtc                              33

SEQ ID NO: 39            moltype = DNA  length = 33
FEATURE                  Location/Qualifiers
source                   1..33
                         mol_type = other DNA
                         organism = synthetic construct
SEQUENCE: 39
agggcttgtc aactctgggc gcaaagaatg tgt                              33

SEQ ID NO: 40            moltype = DNA  length = 33
FEATURE                  Location/Qualifiers
source                   1..33
                         mol_type = other DNA
                         organism = synthetic construct
SEQUENCE: 40
acaatgaggc tgcgaccggg tgtcgaatga aat                              33

SEQ ID NO: 41            moltype = DNA  length = 33
FEATURE                  Location/Qualifiers
```

-continued

```
source                 1..33
                       mol_type = other DNA
                       organism = synthetic construct
SEQUENCE: 41
tgttgcatct ccacccggat tgagccttca gct                             33

SEQ ID NO: 42          moltype = DNA  length = 33
FEATURE                Location/Qualifiers
source                 1..33
                       mol_type = other DNA
                       organism = synthetic construct
SEQUENCE: 42
cacaacggga gctgtggaat tggttcacct ggt                             33

SEQ ID NO: 43          moltype = DNA  length = 33
FEATURE                Location/Qualifiers
source                 1..33
                       mol_type = other DNA
                       organism = synthetic construct
SEQUENCE: 43
tggactaaga ctcgtcctcc agcggaccta agt                             33

SEQ ID NO: 44          moltype = DNA  length = 33
FEATURE                Location/Qualifiers
source                 1..33
                       mol_type = other DNA
                       organism = synthetic construct
SEQUENCE: 44
gtatgatggt gttgcggctt ctcgcttaac gct                             33

SEQ ID NO: 45          moltype = DNA  length = 33
FEATURE                Location/Qualifiers
source                 1..33
                       mol_type = other DNA
                       organism = synthetic construct
SEQUENCE: 45
tctgagtgcc agtgacttca cgcattcgct tgt                             33

SEQ ID NO: 46          moltype = DNA  length = 33
FEATURE                Location/Qualifiers
source                 1..33
                       mol_type = other DNA
                       organism = synthetic construct
SEQUENCE: 46
tacgacacac tcgggctcta tgggcttcat ggt                             33

SEQ ID NO: 47          moltype = DNA  length = 33
FEATURE                Location/Qualifiers
source                 1..33
                       mol_type = other DNA
                       organism = synthetic construct
SEQUENCE: 47
gtttgagtga aggcggtcca acccttagtg cgt                             33

SEQ ID NO: 48          moltype = DNA  length = 33
FEATURE                Location/Qualifiers
source                 1..33
                       mol_type = other DNA
                       organism = synthetic construct
SEQUENCE: 48
ctataagttt gtcgtgcccg tgagccttca gct                             33

SEQ ID NO: 49          moltype = DNA  length = 33
FEATURE                Location/Qualifiers
source                 1..33
                       mol_type = other DNA
                       organism = synthetic construct
SEQUENCE: 49
ggagtgacac tgactacgtt tggttcacct ggt                             33

SEQ ID NO: 50          moltype = DNA  length = 33
FEATURE                Location/Qualifiers
source                 1..33
                       mol_type = other DNA
                       organism = synthetic construct
SEQUENCE: 50
gtcaacgccc tagcagacat agcggaccta agt                             33

SEQ ID NO: 51          moltype = DNA  length = 33
```

```
FEATURE                 Location/Qualifiers
source                  1..33
                        mol_type = other DNA
                        organism = synthetic construct
SEQUENCE: 51
ccagaaccta ttgagcctga ctcgcttaac gct                              33

SEQ ID NO: 52           moltype = DNA  length = 33
FEATURE                 Location/Qualifiers
source                  1..33
                        mol_type = other DNA
                        organism = synthetic construct
SEQUENCE: 52
aggtgttcgt acaatgaggc cgcattcgct tgt                              33

SEQ ID NO: 53           moltype = DNA  length = 33
FEATURE                 Location/Qualifiers
source                  1..33
                        mol_type = other DNA
                        organism = synthetic construct
SEQUENCE: 53
tggtcaaggg caactaatcc tgggcttcat ggt                              33

SEQ ID NO: 54           moltype = DNA  length = 33
FEATURE                 Location/Qualifiers
source                  1..33
                        mol_type = other DNA
                        organism = synthetic construct
SEQUENCE: 54
acaattaccc gtttaccggc acccttagtg cgt                              33

SEQ ID NO: 55           moltype = DNA  length = 33
FEATURE                 Location/Qualifiers
source                  1..33
                        mol_type = other DNA
                        organism = synthetic construct
SEQUENCE: 55
tcgacttccg agttaggccc acctctacgt tgt                              33

SEQ ID NO: 56           moltype = DNA  length = 33
FEATURE                 Location/Qualifiers
source                  1..33
                        mol_type = other DNA
                        organism = synthetic construct
SEQUENCE: 56
tggtccactt ggttaaggtg tcgagggcaa cac                              33

SEQ ID NO: 57           moltype = DNA  length = 33
FEATURE                 Location/Qualifiers
source                  1..33
                        mol_type = other DNA
                        organism = synthetic construct
SEQUENCE: 57
tgaatccagg cgacctcctg ctcagaatca ggt                              33

SEQ ID NO: 58           moltype = DNA  length = 33
FEATURE                 Location/Qualifiers
source                  1..33
                        mol_type = other DNA
                        organism = synthetic construct
SEQUENCE: 58
tcgcaattcg ctcttcggcg ttgtggtagt atg                              33

SEQ ID NO: 59           moltype = DNA  length = 33
FEATURE                 Location/Qualifiers
source                  1..33
                        mol_type = other DNA
                        organism = synthetic construct
SEQUENCE: 59
tgttcgctta cgcacttcag tgaccgtgag tct                              33

SEQ ID NO: 60           moltype = DNA  length = 33
FEATURE                 Location/Qualifiers
source                  1..33
                        mol_type = other DNA
                        organism = synthetic construct
SEQUENCE: 60
tggtacttcg ggtatctcgg gctcacacag cat                              33
```

-continued

```
SEQ ID NO: 61           moltype = DNA  length = 33
FEATURE                 Location/Qualifiers
source                  1..33
                        mol_type = other DNA
                        organism = synthetic construct
SEQUENCE: 61
tgcgtgattc ccaacctggc ggaagtgagt ttg                              33

SEQ ID NO: 62           moltype = DNA  length = 33
FEATURE                 Location/Qualifiers
source                  1..33
                        mol_type = other DNA
                        organism = synthetic construct
SEQUENCE: 62
tcgacttccg agtgcccgtg ctgtttgaat atc                              33

SEQ ID NO: 63           moltype = DNA  length = 33
FEATURE                 Location/Qualifiers
source                  1..33
                        mol_type = other DNA
                        organism = synthetic construct
SEQUENCE: 63
tggtccactt ggtttgcatc agtcacagtg agg                              33

SEQ ID NO: 64           moltype = DNA  length = 33
FEATURE                 Location/Qualifiers
source                  1..33
                        mol_type = other DNA
                        organism = synthetic construct
SEQUENCE: 64
tgaatccagg cgatacagac gatcccgcaa ctg                              33

SEQ ID NO: 65           moltype = DNA  length = 33
FEATURE                 Location/Qualifiers
source                  1..33
                        mol_type = other DNA
                        organism = synthetic construct
SEQUENCE: 65
tcgcaattcg ctcagtccga gttatccaag acc                              33

SEQ ID NO: 66           moltype = DNA  length = 33
FEATURE                 Location/Qualifiers
source                  1..33
                        mol_type = other DNA
                        organism = synthetic construct
SEQUENCE: 66
tgttcgctta cgccggagta acatgcttgt gga                              33

SEQ ID NO: 67           moltype = DNA  length = 33
FEATURE                 Location/Qualifiers
source                  1..33
                        mol_type = other DNA
                        organism = synthetic construct
SEQUENCE: 67
tggtacttcg ggtcctaatc aacgggaact ggt                              33

SEQ ID NO: 68           moltype = DNA  length = 33
FEATURE                 Location/Qualifiers
source                  1..33
                        mol_type = other DNA
                        organism = synthetic construct
SEQUENCE: 68
tgcgtgattc ccacggccat ttgcccatta aca                              33

SEQ ID NO: 69           moltype = DNA  length = 33
FEATURE                 Location/Qualifiers
source                  1..33
                        mol_type = other DNA
                        organism = synthetic construct
SEQUENCE: 69
acaacgtaga ggtgggccta actcggaagt cga                              33

SEQ ID NO: 70           moltype = DNA  length = 33
FEATURE                 Location/Qualifiers
source                  1..33
                        mol_type = other DNA
                        organism = synthetic construct
SEQUENCE: 70
gtgttgccct cgacacctta accaagtgga cca                              33
```

```
SEQ ID NO: 71          moltype = DNA  length = 33
FEATURE                Location/Qualifiers
source                 1..33
                       mol_type = other DNA
                       organism = synthetic construct
SEQUENCE: 71
acctgattct gagcaggagg tcgcctggat tca                              33

SEQ ID NO: 72          moltype = DNA  length = 33
FEATURE                Location/Qualifiers
source                 1..33
                       mol_type = other DNA
                       organism = synthetic construct
SEQUENCE: 72
catactacca caacgccgaa gagcgaattg cga                              33

SEQ ID NO: 73          moltype = DNA  length = 33
FEATURE                Location/Qualifiers
source                 1..33
                       mol_type = other DNA
                       organism = synthetic construct
SEQUENCE: 73
agactcacgg tcactgaagt gcgtaagcga aca                              33

SEQ ID NO: 74          moltype = DNA  length = 33
FEATURE                Location/Qualifiers
source                 1..33
                       mol_type = other DNA
                       organism = synthetic construct
SEQUENCE: 74
atgctgtgtg agcccgagat acccgaagta cca                              33

SEQ ID NO: 75          moltype = DNA  length = 33
FEATURE                Location/Qualifiers
source                 1..33
                       mol_type = other DNA
                       organism = synthetic construct
SEQUENCE: 75
caaactcact tccgccaggt tgggaatcac gca                              33

SEQ ID NO: 76          moltype = DNA  length = 33
FEATURE                Location/Qualifiers
source                 1..33
                       mol_type = other DNA
                       organism = synthetic construct
SEQUENCE: 76
gatattcaaa cagcacgggc actcggaagt cga                              33

SEQ ID NO: 77          moltype = DNA  length = 33
FEATURE                Location/Qualifiers
source                 1..33
                       mol_type = other DNA
                       organism = synthetic construct
SEQUENCE: 77
cctcactgtg actgatgcaa accaagtgga cca                              33

SEQ ID NO: 78          moltype = DNA  length = 33
FEATURE                Location/Qualifiers
source                 1..33
                       mol_type = other DNA
                       organism = synthetic construct
SEQUENCE: 78
cagttgcggg atcgtctgta tcgcctggat tca                              33

SEQ ID NO: 79          moltype = DNA  length = 33
FEATURE                Location/Qualifiers
source                 1..33
                       mol_type = other DNA
                       organism = synthetic construct
SEQUENCE: 79
ggtcttggat aactcggact gagcgaattg cga                              33

SEQ ID NO: 80          moltype = DNA  length = 33
FEATURE                Location/Qualifiers
source                 1..33
                       mol_type = other DNA
                       organism = synthetic construct
SEQUENCE: 80
```

```
tccacaagca tgttactccg gcgtaagcga aca                              33

SEQ ID NO: 81          moltype = DNA  length = 33
FEATURE                Location/Qualifiers
source                 1..33
                       mol_type = other DNA
                       organism = synthetic construct
SEQUENCE: 81
accagttccc gttgattagg acccgaagta cca                              33

SEQ ID NO: 82          moltype = DNA  length = 33
FEATURE                Location/Qualifiers
source                 1..33
                       mol_type = other DNA
                       organism = synthetic construct
SEQUENCE: 82
tgttaatggg caaatggccg tgggaatcac gca                              33

SEQ ID NO: 83          moltype = DNA  length = 33
FEATURE                Location/Qualifiers
source                 1..33
                       mol_type = other DNA
                       organism = synthetic construct
SEQUENCE: 83
agctgaaggc tcaatccggg tggagatgca aca                              33

SEQ ID NO: 84          moltype = DNA  length = 33
FEATURE                Location/Qualifiers
source                 1..33
                       mol_type = other DNA
                       organism = synthetic construct
SEQUENCE: 84
accaggtgaa ccaattccac agctcccgtt gtg                              33

SEQ ID NO: 85          moltype = DNA  length = 33
FEATURE                Location/Qualifiers
source                 1..33
                       mol_type = other DNA
                       organism = synthetic construct
SEQUENCE: 85
acttaggtcc gctggaggac gagtcttagt cca                              33

SEQ ID NO: 86          moltype = DNA  length = 33
FEATURE                Location/Qualifiers
source                 1..33
                       mol_type = other DNA
                       organism = synthetic construct
SEQUENCE: 86
agcgttaagc gagaagccgc aacaccatca tac                              33

SEQ ID NO: 87          moltype = DNA  length = 33
FEATURE                Location/Qualifiers
source                 1..33
                       mol_type = other DNA
                       organism = synthetic construct
SEQUENCE: 87
acaagcgaat gcgtgaagtc actggcactc aga                              33

SEQ ID NO: 88          moltype = DNA  length = 33
FEATURE                Location/Qualifiers
source                 1..33
                       mol_type = other DNA
                       organism = synthetic construct
SEQUENCE: 88
accatgaagc ccatagagcc cgagtgtgtc gta                              33

SEQ ID NO: 89          moltype = DNA  length = 33
FEATURE                Location/Qualifiers
source                 1..33
                       mol_type = other DNA
                       organism = synthetic construct
SEQUENCE: 89
acgcactaag ggttggaccg ccttcactca aac                              33

SEQ ID NO: 90          moltype = DNA  length = 33
FEATURE                Location/Qualifiers
source                 1..33
                       mol_type = other DNA
                       organism = synthetic construct
```

-continued

```
SEQUENCE: 90
agctgaaggc tcacgggcac gacaaactta tag                               33

SEQ ID NO: 91           moltype = DNA  length = 33
FEATURE                 Location/Qualifiers
source                  1..33
                        mol_type = other DNA
                        organism = synthetic construct
SEQUENCE: 91
accaggtgaa ccaaacgtag tcagtgtcac tcc                               33

SEQ ID NO: 92           moltype = DNA  length = 33
FEATURE                 Location/Qualifiers
source                  1..33
                        mol_type = other DNA
                        organism = synthetic construct
SEQUENCE: 92
acttaggtcc gctatgtctg ctagggcgtt gac                               33

SEQ ID NO: 93           moltype = DNA  length = 33
FEATURE                 Location/Qualifiers
source                  1..33
                        mol_type = other DNA
                        organism = synthetic construct
SEQUENCE: 93
agcgttaagc gagtcaggct caataggttc tgg                               33

SEQ ID NO: 94           moltype = DNA  length = 33
FEATURE                 Location/Qualifiers
source                  1..33
                        mol_type = other DNA
                        organism = synthetic construct
SEQUENCE: 94
acaagcgaat gcggcctcat tgtacgaaca cct                               33

SEQ ID NO: 95           moltype = DNA  length = 33
FEATURE                 Location/Qualifiers
source                  1..33
                        mol_type = other DNA
                        organism = synthetic construct
SEQUENCE: 95
accatgaagc ccaggattag ttgcccttga cca                               33

SEQ ID NO: 96           moltype = DNA  length = 33
FEATURE                 Location/Qualifiers
source                  1..33
                        mol_type = other DNA
                        organism = synthetic construct
SEQUENCE: 96
acgcactaag ggtgccggta aacgggtaat tgt                               33
```